United States Patent
Han et al.

(10) Patent No.: US 10,053,461 B2
(45) Date of Patent: Aug. 21, 2018

(54) TETRACYCLIC 4-OXO-PYRIDINE-3-CARBOXYLIC ACID DERIVATIVES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Xingchun Han, Shanghai (CN); Min Jiang, Shanghai (CN); Yongguang Wang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/867,010

(22) Filed: Jan. 10, 2018

(65) Prior Publication Data

US 2018/0127416 A1    May 10, 2018

Related U.S. Application Data

(63) Continuation of application No. PCT/EP2016/067607, filed on Jul. 25, 2016.

(30) Foreign Application Priority Data

Jul. 27, 2015  (WO) ................ PCT/CN2015/085191

(51) Int. Cl.
| | |
|---|---|
| *C07D 471/06* | (2006.01) |
| *A61K 31/4745* | (2006.01) |
| *C07D 471/14* | (2006.01) |
| *C07D 455/06* | (2006.01) |
| *C07D 491/147* | (2006.01) |
| *C07D 495/14* | (2006.01) |
| *A61P 31/20* | (2006.01) |

(52) U.S. Cl.
CPC ............ *C07D 471/14* (2013.01); *A61P 31/20* (2018.01); *C07D 455/06* (2013.01); *C07D 491/147* (2013.01); *C07D 495/14* (2013.01)

(58) Field of Classification Search
CPC .. C07D 471/06; C07D 471/16; C07D 491/16; A61K 31/4745; A61K 31/473

USPC ................. 546/71, 70, 62; 514/284, 285
See application file for complete search history.

(56) References Cited

U.S. PATENT DOCUMENTS 9,845,325 B2 * 12/2017 Fu .................. C07D 471/14

FOREIGN PATENT DOCUMENTS

| JP | S60197684 A | 7/1985 |
|---|---|---|
| WO | 2015/113990 A1 | 8/2015 |
| WO | 2015/173164 A1 | 11/2015 |
| WO | 2016/017215 A1 | 5/2016 |

OTHER PUBLICATIONS

Fecik et al., "Chiral DNA gyrase inhibitors. 3. Probing the chiral preference of the active site of DNA gyrase. Synthesis of 10-fluoro-6-methyl-6,7-dihydro-9-piperazinyl-2H-benzo[a]quinolizin-20-one-3-carboxylic acid analogues" J Med Chem 48(4):1229-1236 ( 2005).

Geng et al., "Small-molecule inhibitors for the treatment of hepatitis B virus documented in patents" Mini Reviews in Medicinal Chemistry 13(5):749-776 (Apr. 1, 2013).

ISR for PCT/EP2016/067607 (dated Aug. 29, 2016).

* cited by examiner

*Primary Examiner* — Charanjit Aulakh
(74) *Attorney, Agent, or Firm* — Brian L. Buckwalter

(57) ABSTRACT

The invention provides novel compounds having the general formula:

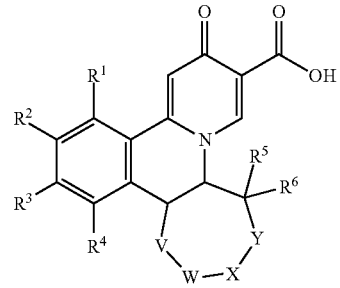

wherein $R^1$ to $R^6$, V, W, X and Y are as described herein, compositions including the compounds and methods of using the compounds.

21 Claims, 1 Drawing Sheet

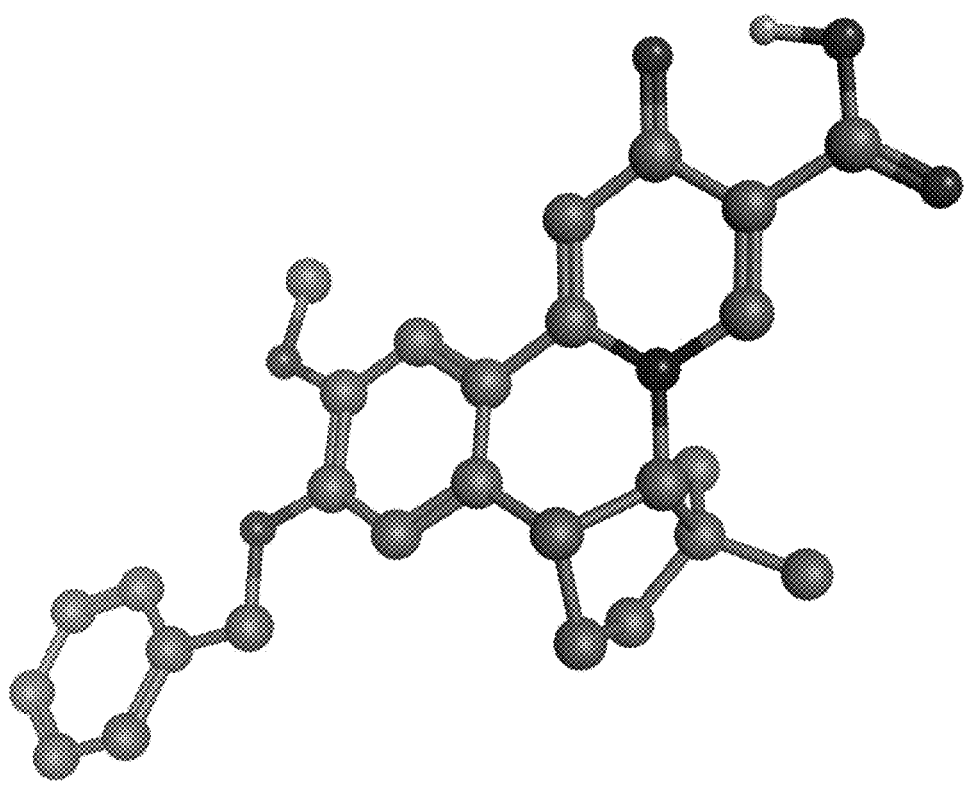

TETRACYCLIC 4-OXO-PYRIDINE-3-CARBOXYLIC ACID DERIVATIVES FOR THE TREATMENT AND PROPHYLAXIS OF HEPATITIS B VIRUS INFECTION

CROSS REFERENCE TO RELATED APPLICATIONS

This application is a continuation of International Application No. PCT/EP2016/067607 having an international filing date Jul. 25, 2016 and which claims benefit under 35 U.S.C. § 119 to International Application No. PCT/CN2015/085191 having an international filing date of Jul. 27, 2015. The entire contents of both are incorporated herein by reference.

FIELD OF THE INVENTION

The present invention relates to organic compounds useful for therapy and/or prophylaxis in a mammal, and in particular to HBsAg (HBV Surface antigen) inhibitors and HBV DNA production inhibitors useful for treating HBV infection.

In particular the present invention relates to novel tetracyclic 4-oxo-pyridine-3-carboxylic acid derivatives of formula (I) having pharmaceutical activity, their manufacture, pharmaceutical compositions containing them and their potential use as medicaments.

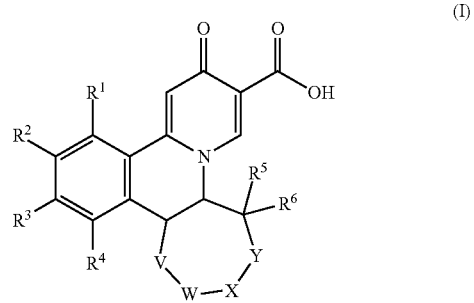

wherein $R^1$ to $R^6$, V, W, X and Y are as described below, or pharmaceutically acceptable salts, or enantiomers, or diastereomer thereof.

BACKGROUND OF THE INVENTION

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, targeting HBsAg together with HBV DNA levels in CHB patients may significantly improve CHB patient immune reactivation and remission (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

The present invention relates to compounds of formula I,

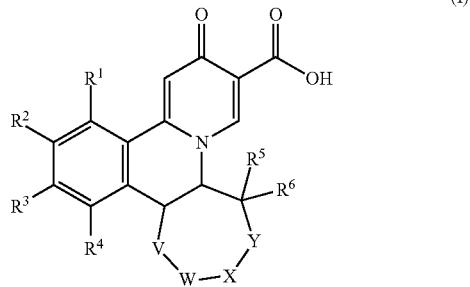

(I)

wherein $R^1$, $R^2$, $R^3$ and $R^4$ are independently selected from hydrogen, $C_{1-6}$alkyl, haloC$_{1-6}$alkyl, halogen, cyano, amino, $C_{1-6}$alkylamino, diC$_{1-6}$alkylamino, pyrrolidinyl and OR$^7$;
$R^5$ is hydrogen or $C_{1-6}$alkyl;
$R^6$ is hydrogen or $C_{1-6}$alkyl;
$R^7$ is hydrogen; $C_{1-6}$alkyl; haloC$_{1-6}$alkyl; $C_{3-7}$cycloalkyl-$C_{1-6}$alkyl; phenylC$_{1-6}$alkyl; cyanoC$_{1-6}$alkyl; hydroxyC$_{1-6}$alkyl; $C_{1-6}$alkoxyC$_{1-6}$alkyl; carboxyC$_{1-6}$alkyl; $C_{1-6}$alkoxycarbonylC$_{1-6}$alkyl; $C_{1-6}$alkylsulfanylC$_{1-6}$alkyl; $C_{1-6}$alkylsulfonylC$_{1-6}$alkyl; aminoC$_{1-6}$alkyl; $C_{1-6}$alkylaminoC$_{1-6}$alkyl; diC$_{1-6}$alkylaminoC$_{1-6}$alkyl; $C_{1-6}$alkylcarbonylaminoC$_{1-6}$alkyl; $C_{1-6}$alkylsulfonylaminoC$_{1-6}$alkyl; $C_{1-6}$alkoxycarbonylaminoC$_{1-6}$alkyl; or heterocycloalkylC$_{1-6}$alkyl, wherein heterocycloalkyl is N-containing monocyclic heterocycloalkyl;
One of V, W, X and Y is selected from CR$^8$R$^9$, O, S, SO$_2$ and NR$^{10}$, the others of V, W, X and Y are independently selected from a bond and CR$^8$R$^9$, wherein
$R^8$ is hydrogen or $C_{1-6}$alkyl;
$R^9$ is hydrogen or $C_{1-6}$alkyl;
$R^{10}$ is phenylC$_{1-6}$alkoxycarbonyl, phenylC$_{1-6}$alkylcarbonyl, phenylC$_{1-6}$alkylsulfonyl, $C_{1-6}$alkoxycarbonyl, $C_{1-6}$alkylcarbonyl, or $C_{1-6}$alkylsulfonyl;
or pharmaceutically acceptable salts, or enantiomers, or diastereomer thereof.

BRIEF DESCRIPTION OF THE FIGURE

FIG. 1: FIG. 1 depicts X-ray structure of (3aS,12bR)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; examples for $C_{1-6}$alkoxy are methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "halogen" means fluorine, chlorine, bromine or iodine.

The term "haloC$_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of "haloC$_{1-6}$alkyl" include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "haloC$_{1-6}$alkyl" group is difluoromethyl or trifluoromethyl.

The term "monocyclic heterocycloalkyl" is a monovalent saturated or partly unsaturated monocyclic ring system of 4 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, 2-oxo-pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Particular "monocyclic heterocycloalkyl" groups are piperidinyl, morpholinyl, 2-oxo-pyrrolidinyl, and pyrrolidinyl.

The term "N-containing monocyclic heterocycloalkyl" is a "monocyclic heterocycloalkyl" as defined above wherein at least one of the heteroatoms is N. Examples for "N-containing monocyclic heterocycloalkyl" are aziridinyl, azetidinyl, pyrrolidinyl, 2-oxo-pyrrolidinyl, pyrazolidinyl, imidazolidinyl, oxazolidinyl, isoxazolidinyl, thiazolidinyl, piperidinyl, piperazinyl, morpholinyl, thiomorpholinyl, 1,1-dioxo-thiomorpholin-4-yl, azepanyl, diazepanyl, homopiperazinyl, or oxazepanyl. Particular "N-containing monocyclic heterocycloalkyl" groups are piperidinyl, morpholinyl, 2-oxo-pyrrolidinyl and pyrrolidinyl.

The term "amino" denotes a group of the formula —NR'R" wherein R' and R" are independently hydrogen, $C_{1-6}$alkyl, $C_{1-6}$alkoxy, $C_{3-7}$cycloalkyl, hetero$C_{3-7}$cycloalkyl, aryl or heteroaryl. Alternatively, R' and R", together with the nitrogen to which they are attached, can form a hetero-$C_{3-7}$cycloalkyl.

The term "carbonyl" alone or in combination refers to the group —C(O)—.

The term "cyano" alone or in combination refers to the group —CN.

The term "$C_{1-6}$alkylsulfanyl" denotes the group —S—R', wherein R' is a $C_{1-6}$alkyl group as defined above.

The term "$C_{1-6}$alkylsulfonyl" denotes a group —$SO_2$—R', wherein R' is a $C_{1-6}$alkyl group as defined above. Examples of $C_{1-6}$alkylsulfonyl include methylsulfonyl and ethylsulfonyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBsAg

The present invention provides (i) novel compounds having the general formula I,

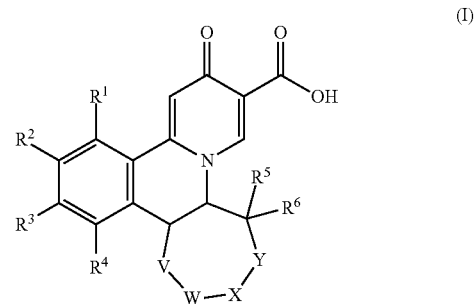

(I)

wherein
$R^1$, $R^2$, $R^3$ and $R^4$ are independently selected from hydrogen, $C_{1-6}$alkyl, halo$C_{1-6}$alkyl, halogen, cyano, amino, $C_{1-6}$alkylamino, di$C_{1-6}$alkylamino, pyrrolidinyl and $OR^7$;
$R^5$ is hydrogen or $C_{1-6}$alkyl;
$R^6$ is hydrogen or $C_{1-6}$alkyl;
$R^7$ is hydrogen; $C_{1-6}$alkyl; halo$C_{1-6}$alkyl; $C_{3-7}$cycloalkyl-$C_{1-6}$alkyl; phenyl$C_{1-6}$alkyl; cyano$C_{1-6}$alkyl; hydroxy$C_{1-6}$alkyl; $C_{1-6}$alkoxy$C_{1-6}$alkyl; carboxy$C_{1-6}$alkyl; $C_{1-6}$alkoxycarbonyl$C_{1-6}$alkyl; $C_{1-6}$alkylsulfanyl$C_{1-6}$alkyl; $C_{1-6}$alkylsulfonyl$C_{1-6}$alkyl; amino$C_{1-6}$alkyl; $C_{1-6}$alkylamino$C_{1-6}$alkyl; di$C_{1-6}$alkylamino$C_{1-6}$alkyl; $C_{1-6}$alkylcarbonylamino$C_{1-6}$alkyl; $C_{1-6}$alkylsulfonylamino$C_{1-6}$alkyl; $C_{1-6}$alkoxycarbonylamino$C_{1-6}$alkyl; or heterocycloalkyl$C_{1-6}$alkyl, wherein heterocycloalkyl is N-containing monocyclic heterocycloalkyl;
One of V, W, X and Y is selected from $CR^8R^9$, O, S, $SO_2$ and $NR^{10}$, the others of V, W, X and Y are independently selected from a bond and $CR^8R^9$, wherein
  $R^8$ is hydrogen or $C_{1-6}$alkyl;
  $R^9$ is hydrogen or $C_{1-6}$alkyl;
  $R^{10}$ is phenyl$C_{1-6}$alkoxycarbonyl, phenyl$C_{1-6}$alkylcarbonyl, phenyl$C_{1-6}$alkylsulfonyl, $C_{1-6}$alkoxycarbonyl, $C_{1-6}$alkylcarbonyl, or $C_{1-6}$alkylsulfonyl;
or pharmaceutically acceptable salts, or enantiomers, or diastereomer thereof.

Another embodiment of present invention is (ii) a compound of formula I, wherein
$R^1$ is hydrogen;
$R^2$ is halogen or $C_{1-6}$alkoxy;
$R^3$ is selected from $C_{1-6}$alkyl, pyrrolidinyl or $OR^7$, wherein
  $R^7$ is hydrogen, $C_{1-6}$alkyl, halo$C_{1-6}$alkyl, $C_{3-7}$cycloalkyl$C_{1-6}$alkyl, phenyl$C_{1-6}$alkyl, cyano$C_{1-6}$alkyl, hydroxy$C_{1-6}$alkyl, $C_{1-6}$alkoxy$C_{1-6}$alkyl, carboxy$C_{1-6}$alkyl, $C_{1-6}$alkoxycarbonyl$C_{1-6}$alkyl, $C_{1-6}$alkylsulfanyl$C_{1-6}$alkyl, $C_{1-6}$alkylsulfonyl$C_{1-6}$alkyl, amino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl, morpholinyl$C_{1-6}$alkyl, pyrrolidinyl$C_{1-6}$alkyl or (2-oxo-pyrrolidinyl)$C_{1-6}$alkyl;

$R^4$ is hydrogen;
$R^5$ is hydrogen or $C_{1-6}$alkyl;
$R^6$ is hydrogen or $C_{1-6}$alkyl;
V and Y are $CH_2$;
X is selected from a bond, $CH_2$, O, S, $SO_2$ and phenyl$C_{1-6}$alkoxycarbonylamino when W is a bond; or
X is $CH_2$ when W is $CH_2$;
or pharmaceutically acceptable salts, or enantiomers, or diastereomer thereof.

A further embodiment of present invention is (iii) a compound of formula I, wherein
$R^1$ is hydrogen;
$R^2$ is chloro or methoxy;
$R^3$ is selected from methyl, ethyl, propyl, pyrrolidinyl, hydroxy, methoxy, difluoroethoxy, trifluoroethoxy, cyclopropylmethoxy, benzyloxy, cyanopropoxy, hydroxypropoxy, hydroxyhexyloxy, hydroxydimethylpropoxy, methoxyethoxy, methoxypropoxy, carboxypropoxy, ethoxycarbonylpropoxy, methylsulfanylpropoxy, methylsulfonylpropoxy, aminohexyloxy, methylcarbonylaminohexyloxy, methylsulfonylaminohexyloxy, tert-butoxycarbonylaminohexyloxy, morpholinylpropoxy, pyrrolidinylpropoxy and (2-oxo-pyrrolidinyl)propoxy;
$R^4$ is hydrogen;
$R^5$ is hydrogen or methyl;
$R^6$ is hydrogen or methyl;
V and Y are $CH_2$;
X is selected from a bond, $CH_2$, O, S, $SO_2$ and phenylmethoxycarbonylamino when W is a bond; or
X is $CH_2$ when W is $CH_2$;
or pharmaceutically acceptable salts, or enantiomers, or diastereomer thereof.

Another embodiment of present invention is (iv) a compound of formula I, wherein
$R^1$ is hydrogen;
$R^2$ is $C_{1-6}$alkoxy;
$R^3$ is selected from $C_{1-6}$alkyl, pyrrolidinyl or $OR^7$, wherein $R^7$ is hydrogen, $C_{1-6}$alkyl, halo$C_{1-6}$alkyl, $C_{3-7}$cycloalkyl$C_{1-6}$alkyl, phenyl$C_{1-6}$alkyl, cyano$C_{1-6}$alkyl, hydroxy$C_{1-6}$alkyl, $C_{1-6}$alkoxy$C_{1-6}$alkyl, carboxy$C_{1-6}$alkyl, $C_{1-6}$alkoxycarbonyl$C_{1-6}$alkyl, $C_{1-6}$alkylsulfanyl$C_{1-6}$alkyl, $C_{1-6}$alkylsulfonyl$C_{1-6}$alkyl, amino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl, morpholinyl$C_{1-6}$alkyl, pyrrolidinyl$C_{1-6}$alkyl or (2-oxo-pyrrolidinyl)$C_{1-6}$alkyl;
$R^4$ is hydrogen;
$R^5$ is $C_{1-6}$alkyl;
$R^6$ is $C_{1-6}$alkyl;
V and Y are $CH_2$;
W is a bond;
X is a bond;
or a pharmaceutically acceptable salts, or enantiomers, or diastereomer thereof.

A further embodiment of present invention is (v) a compound of formula I as defined above, or pharmaceutically acceptable salts, or enantiomers, or diastereomer thereof, wherein $R^2$ is methoxy, and all remaining substituents have the significances given herein before.

A further embodiment of present invention is (vi) a compound of formula I as defined above, or pharmaceutically acceptable salts, or enantiomers, or diastereomer thereof, wherein $R^3$ is $OR^7$, wherein $R^7$ is $C_{1-6}$alkyl, halo$C_{1-6}$alkyl, $C_{3-7}$cycloalkyl$C_{1-6}$alkyl, hydroxy$C_{1-6}$alkyl, $C_{1-6}$alkoxy$C_{1-6}$alkyl, $C_{1-6}$alkylsulfanyl$C_{1-6}$alkyl, $C_{1-6}$alkylsulfonyl$C_{1-6}$alkyl, amino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl or morpholinyl$C_{1-6}$alkyl; and all remaining substituents have the significances given herein before.

A further embodiment of present invention is (vii) a compound of formula I as defined above, or pharmaceutically acceptable salts, or enantiomers, or diastereomer, or diastereomer thereof, wherein $R^3$ is selected from methoxy, difluoroethoxy, trifluoroethoxy, cyclopropylmethoxy, hydroxypropoxy, hydroxyhexyloxy, hydroxydimethylpropoxy, methoxyethoxy, methoxypropoxy, methylsulfanylpropoxy, methylsulfonylpropoxy, aminohexyloxy, methylcarbonylaminohexyloxy, methylsulfonylaminohexyloxy, tert-butoxycarbonylaminohexyloxy or morpholinylpropoxy, and all remaining substituents have the significances given herein before.

A further embodiment of present invention is (viii) a compound of formula I as defined above, or pharmaceutically acceptable salts, or enantiomers, or diastereomer thereof, wherein $R^5$ is methyl; $R^6$ is methyl, and all remaining substituents have the significances given herein before.

Another embodiment of present invention is (ix) a compound of formula I, wherein
$R^1$ is hydrogen;
$R^2$ is halogen or $C_{1-6}$alkoxy;
$R^3$ is $OR^7$; wherein $R^7$ is phenyl$C_{1-6}$alkyl or $C_{1-6}$alkoxy-$C_{1-6}$alkyl;
$R^4$ is hydrogen;
$R^5$ is hydrogen;
$R^6$ is hydrogen;
V and Y are $CH_2$;
X is selected from $CH_2$, O, S, $SO_2$ and phenyl$C_{1-6}$alkoxycarbonylamino when W is a bond; or
X is $CH_2$ when W is $CH_2$;
or pharmaceutically acceptable salts, or enantiomers, or diastereomer thereof.

A further embodiment of present invention is (x) a compound of formula I as defined above, or pharmaceutically acceptable salts, or enantiomers, or diastereomer thereof, wherein $R^2$ is chloro or methoxy, and all remaining substituents have the significances given herein before.

A further embodiment of present invention is (xi) a compound of formula I as defined above, or pharmaceutically acceptable salts, or enantiomers, or diastereomer thereof, wherein $R^3$ is benzyloxy or methoxypropoxy, and all remaining substituents have the significances given herein before.

A further embodiment of present invention is (xii) a compound of formula I as defined above, or pharmaceutically acceptable salts, or enantiomers, or diastereomer thereof, wherein X is $CH_2$ or S when W is a bond, or X is $CH_2$ when W is $CH_2$, and all remaining substituents have the significances given herein before.

Another embodiment of present invention is (xiii) a compound of formula I, wherein
$R^1$ is hydrogen;
$R^2$ is halogen or $C_{1-6}$alkoxy;
$R^3$ is selected from $C_{1-6}$alkyl, pyrrolidinyl or $OR^7$, wherein $R^7$ is halo$C_{1-6}$alkyl, hydroxy$C_{1-6}$alkyl, $C_{1-6}$alkoxy$C_{1-6}$alkyl, $C_{1-6}$alkylsulfonyl$C_{1-6}$alkyl, $C_{1-6}$alkylcarbonylamino$C_{1-6}$alkyl, $C_{1-6}$alkylsulfonylamino$C_{1-6}$alkyl or morpholinyl$C_{1-6}$alkyl;
$R^4$ is hydrogen;
$R^5$ is hydrogen or $C_{1-6}$alkyl;
$R^6$ is hydrogen or $C_{1-6}$alkyl;
V and Y are $CH_2$;
X is a bond or S when W is a bond, or
X is $CH_2$ when W is $CH_2$;

or pharmaceutically acceptable salts, or enantiomers, or diastereomer thereof.

Another embodiment of present invention is (xiv) a compound of formula I, wherein
$R^1$ is hydrogen;
$R^2$ is chloro or methoxy;
$R^3$ is selected from ethyl, pyrrolidinyl, difluoroethoxy, trifluoroethoxy, hydroxydimethylpropoxy, methoxypropoxy, methylsulfonylpropoxy, methylcarbonylaminohexyloxy, methylsulfonylaminohexyloxy and morpholinylpropoxy;
$R^4$ is hydrogen;
$R^5$ is hydrogen or methyl;
$R^6$ is hydrogen or methyl;
V and Y are $CH_2$;
X is a bond or S when W is a bond, or
X is $CH_2$ when W is $CH_2$;
or pharmaceutically acceptable salts, or enantiomers, or diastereomer thereof.

A further embodiment of the present invention is (xv) cis-isomer of formula I, or pharmaceutically acceptable salts, or enantiomers or diastereomers thereof, wherein $R^1$ to $R^6$, V, W, X and Y have the significances given herein before.

Another embodiment of the present invention is (xvi) trans-isomer of formula I, or pharmaceutically acceptable salts, or enantiomers or diastereomers thereof, wherein $R^1$ to $R^6$, V, W, X and Y have the significances given herein before.

Particular compounds of formula I according to the invention are the following:

Trans-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid;

Cis-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid;

Cis-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid;

(3aS,12bR)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid;

(3aR,12bS)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-hydroxy-10-methoxy-3,3-dimethyl-7-oxo-1,2,3,3a,7,12b-hexahydrocyclopenta[c]pyrido[2,1-a]isoquinoline-6-carboxylic acid;

Cis-10,11-dimethoxy-3,3-dimethyl-7-oxo-1,2,3,3a,7,12b-hexahydrocyclopenta[c]pyrido[2,1-a]isoquinoline-6-carboxylic acid;

Cis-10-methoxy-3,3-dimethyl-7-oxo-11-(2,2,2-trifluoroethoxy)-1,2,3,3a,7,12b-hexahydrocyclopenta[c]pyrido[2,1-a]isoquinoline-6-carboxylic acid;

Cis-11-isobutoxy-10-methoxy-3,3-dimethyl-7-oxo-1,2,3,3a,7,12b-hexahydrocyclopenta[c]pyrido[2,1-a]isoquinoline-6-carboxylic acid;

Cis-11-(cyclopropylmethoxy)-10-methoxy-3,3-dimethyl-7-oxo-1,2,3,3a,7,12b-hexahydrocyclopenta[c]pyrido[2,1-a]isoquinoline-6-carboxylic acid;

Cis-10-methoxy-11-(2-methoxyethoxy)-3,3-dimethyl-7-oxo-1,2,3,3a,7,12b-hexahydrocyclopenta[c]pyrido[2,1-a]isoquinoline-6-carboxylic acid;

Cis-11-(3-cyanopropoxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-(3-hydroxypropoxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-(3-hydroxy-2,2-dimethylpropoxy)-10-methoxy-3,3-dimethyl-7-oxo-1,2,3,3a,7,12b-hexahydrocyclopenta[c]pyrido[2,1-a]isoquinoline-6-carboxylic acid;

Cis-10-methoxy-3,3-dimethyl-11-(3-morpholinopropoxy)-7-oxo-1,2,3,3a,7,12b-hexahydrocyclopenta[c]pyrido[2,1-a]isoquinoline-6-carboxylic acid;

Cis-10-methoxy-3,3-dimethyl-7-oxo-11-(3-(pyrrolidin-1-yl)propoxy)-1,2,3,3a,7,12b-hexahydrocyclopenta[c]pyrido[2,1-a]isoquinoline-6-carboxylic acid;

Cis-10-methoxy-3,3-dimethyl-7-oxo-11-(3-(2-oxopyrrolidin-1-yl)propoxy)-1,2,3,3a,7,12b-hexahydrocyclopenta[c]pyrido[2,1-a]isoquinoline-6-carboxylic acid;

Cis-11-(4-ethoxy-4-oxobutoxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-(3-carboxypropoxy)-10-methoxy-3,3-dimethyl-7-oxo-1,2,3,3a,7,12b-hexahydrocyclopenta[c]pyrido[2,1-a]isoquinoline-6-carboxylic acid;

Cis-10-methoxy-3,3-dimethyl-11-(3-(methylthio)propoxy)-7-oxo-1,2,3,3a,7,12b-hexahydrocyclopenta[c]pyrido[2,1-a]isoquinoline-6-carboxylic acid;

Cis-10-methoxy-3,3-dimethyl-11-(3-(methylsulfonyl)propoxy)-7-oxo-1,2,3,3a,7,12b-hexahydrocyclopenta[c]pyrido[2,1-a]isoquinoline-6-carboxylic acid;

Cis-11-((6-hydroxyhexyl)oxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-((6-(((tert-butoxycarbonyl)amino)hexyl)oxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-((6-acetamidohexyl)oxy)-10-methoxy-3,3-dimethyl-7-oxo-1,2,3,3a,7,12b-hexahydrocyclopenta[c]pyrido[2,1-a]isoquinoline-6-carboxylic acid;

Cis-10-methoxy-3,3-dimethyl-11-((6-(methylsulfonamido)hexyl)oxy)-7-oxo-1,2,3,3a,7,12b-hexahydrocyclopenta[c]pyrido[2,1-a]isoquinoline-6-carboxylic acid;

Trans-13-chloro-12-(3-methoxypropoxy)-2-oxo-2,5a,6,7,8,9,10,10a-octahydrocyclohepta[c]pyrido[2,1-a]isoquinoline-3-carboxylic acid;

Cis-13-chloro-12-(3-methoxypropoxy)-2-oxo-2,5a,6,7,8,9,10,10a-octahydrocyclohepta[c]pyrido[2,1-a]isoquinoline-3-carboxylic acid;

Trans-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid;

Cis-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid;

Trans-12-benzyloxy-11-methoxy-8-oxo-1,2,3,4,4a,13b-hexahydropyrido[1,2-f]phenanthridine-7-carboxylic acid;

Cis-12-benzyloxy-11-methoxy-8-oxo-1,2,3,4,4a,13b-hexahydropyrido[1,2-f]phenanthridine-7-carboxylic acid;

Trans-11-methoxy-12-(3-methoxypropoxy)-8-oxo-1,3,4,4a,8,13b-hexahydropyrano[4,3-c]pyrido[2,1-a]isoquinoline-7-carboxylic acid;

Cis-11-methoxy-12-(3-methoxypropoxy)-8-oxo-1,3,4,4a,8,13b-hexahydropyrano[4,3-c]pyrido[2,1-a]isoquinoline-7-carboxylic acid;

Trans-11-methoxy-12-(3-methoxypropoxy)-8-oxo-1,3,4,4a,8,13b-hexahydropyrido[2,1-a]thiopyrano[4,3-c]isoquinoline-7-carboxylic acid;
Cis-11-methoxy-12-(3-methoxypropoxy)-8-oxo-1,3,4,4a,8,13b-hexahydropyrido[2,1-a]thiopyrano[4,3-c]isoquinoline-7-carboxylic acid;
Trans-11-methoxy-12-(3-methoxypropoxy)-8-oxo-1,3,4,4a,8,13b-hexahydropyrido[2,1-a]thiopyrano[4,3-c]isoquinoline-7-carboxylic acid 2,2-dioxide;
Cis-10-methoxy-3,3,11-trimethyl-7-oxo-1,2,3,3a,7,12b-hexahydrocyclopenta[c]pyrido[2,1-a]isoquinoline-6-carboxylic acid;
Cis-10-methoxy-3,3,11-trimethyl-7-oxo-1,2,3,3a,7,12b-hexahydrocyclopenta[c]pyrido[2,1-a]isoquinoline-6-carboxylic acid;
Cis-10-methoxy-3,3-dimethyl-7-oxo-11-propyl-1,2,3,3a,7,12b-hexahydrocyclopenta[c]pyrido[2,1-a]isoquinoline-6-carboxylic acid;
Cis-10-methoxy-3,3-dimethyl-7-oxo-11-(pyrrolidin-1-yl)-1,2,3,3a,7,12b-hexahydrocyclopenta[c]pyrido[2,1-a]isoquinoline-6-carboxylic acid;
or pharmaceutically acceptable salts, or enantiomers, or diastereomer thereof.

More particularly, the invention relates to the following compounds of formula I:
Trans-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid;
Cis-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid;
Cis-10-methoxy-3,3-dimethyl-7-oxo-11-(2,2,2-trifluoroethoxy)-1,2,3,3a,7,12b-hexahydrocyclopenta[c]pyrido[2,1-a]isoquinoline-6-carboxylic acid;
Cis-11-isobutoxy-10-methoxy-3,3-dimethyl-7-oxo-1,2,3,3a,7,12b-hexahydrocyclopenta[c]pyrido[2,1-a]isoquinoline-6-carboxylic acid;
Cis-11-(3-hydroxy-2,2-dimethylpropoxy)-10-methoxy-3,3-dimethyl-7-oxo-1,2,3,3a,7,12b-hexahydrocyclopenta[c]pyrido[2,1-a]isoquinoline-6-carboxylic acid;
Cis-10-methoxy-3,3-dimethyl-11-(3-morpholinopropoxy)-7-oxo-1,2,3,3a,7,12b-hexahydrocyclopenta[c]pyrido[2,1-a]isoquinoline-6-carboxylic acid;
Cis-10-methoxy-3,3-dimethyl-11-(3-(methylsulfonyl)propoxy)-7-oxo-1,2,3,3a,7,12b-hexahydrocyclopenta[c]pyrido[2,1-a]isoquinoline-6-carboxylic acid;
Cis-11-((6-acetamidohexyl)oxy)-10-methoxy-3,3-dimethyl-7-oxo-1,2,3,3a,7,12b-hexahydrocyclopenta[c]pyrido[2,1-a]isoquinoline-6-carboxylic acid;
Cis-10-methoxy-3,3-dimethyl-11-((6-(methylsulfonamido)hexyl)oxy)-7-oxo-1,2,3,3a,7,12b-hexahydrocyclopenta[c]pyrido[2,1-a]isoquinoline-6-carboxylic acid;
Cis-13-chloro-12-(3-methoxypropoxy)-2-oxo-2,5a,6,7,8,9,10,10a-octahydrocyclohepta[c]pyrido[2,1-a]isoquinoline-3-carboxylic acid;
Cis-11-methoxy-12-(3-methoxypropoxy)-8-oxo-1,3,4,4a,8,13b-hexahydropyrido[2,1-a]thiopyrano[4,3-c]isoquinoline-7-carboxylic acid;
Cis-10-methoxy-3,3,11-trimethyl-7-oxo-1,2,3,3a,7,12b-hexahydrocyclopenta[c]pyrido[2,1-a]isoquinoline-6-carboxylic acid;
Cis-10-methoxy-3,3-dimethyl-7-oxo-11-(pyrrolidin-1-yl)-1,2,3,3a,7,12b-hexahydrocyclopenta[c]pyrido[2,1-a]isoquinoline-6-carboxylic acid;
or pharmaceutically acceptable salts, or enantiomers thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^6$, V, W, X and Y are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Intermediates (Scheme 1)

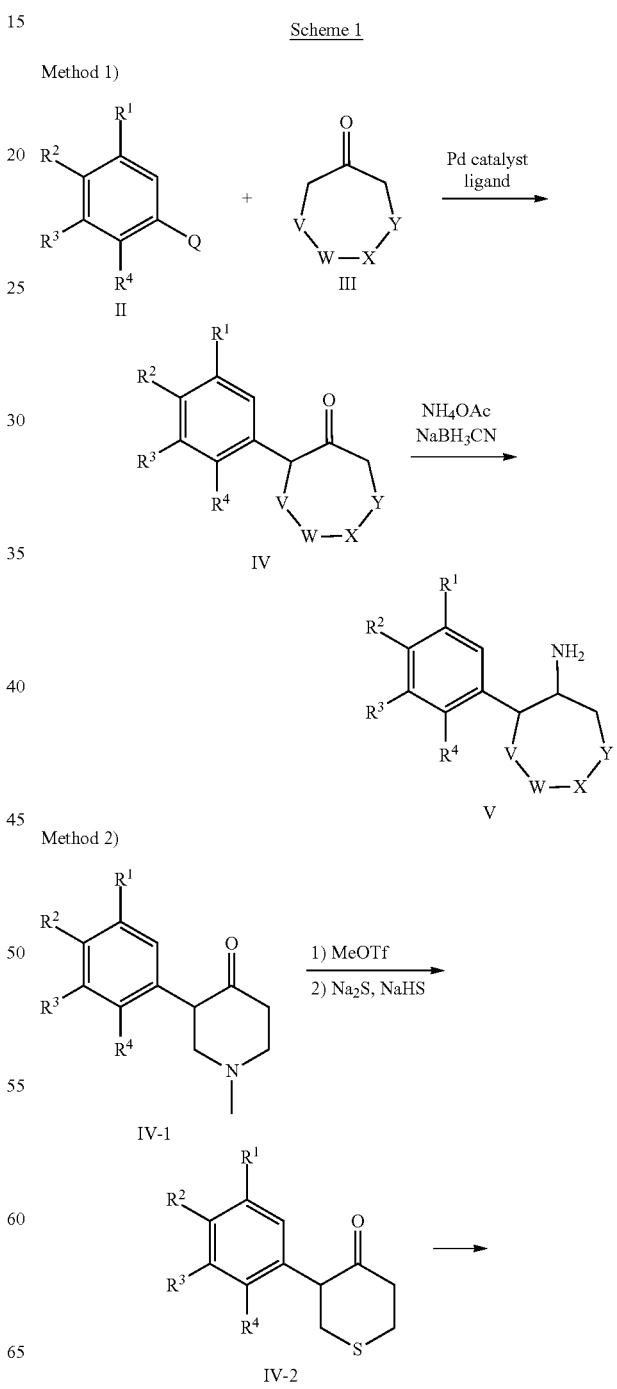

-continued

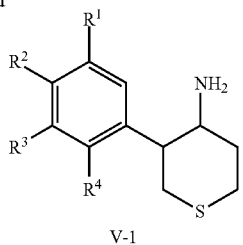

V-1

Intermediates can be prepared according to Scheme 1, wherein Q is Br or I; None of V, W, X and Y is S.

By Method 1) Coupling reaction of Halide II with Ketone III affords Compound IV. The reaction can be carried out in the presence of a Pd catalyst such as $Pd_2(dba)_3$, $Pd(PPh_3)_4$ or $PdCl_2(PPh_3)_2$, a ligand such as Xantphos, and a suitable base such as tert-BuONa, $Na_2CO_3$ or $Cs_2CO_3$, in a suitable solvent such as THF, toluene or 1,4-dioxane at a temperature between room temperature and 130° C. Reductive amination of Compound IV affords Amine V. The reaction can be carried out by using $NH_4OAc$ and $NaBH_3CN$ in a suitable solvent such as methanol.

By Method 2), quaternization of Compound IV-1 with methyl trifluoromethanesulfonate followed by heating with NaHS, $Na_2S$ and water affords Compound IV-2. The quaternization reaction can be carried out in a suitable solvent such as isobutyl methylketone at 0° C. to room temperature. Reductive amination of Compound IV-2 by using $NH_4OAc$ and $NaBH_3CN$ affords Compound V-1.

General Synthetic Route for Compounds I, Ia, Ib, Iaa, Iab, Iba and Ibb (Scheme 2)

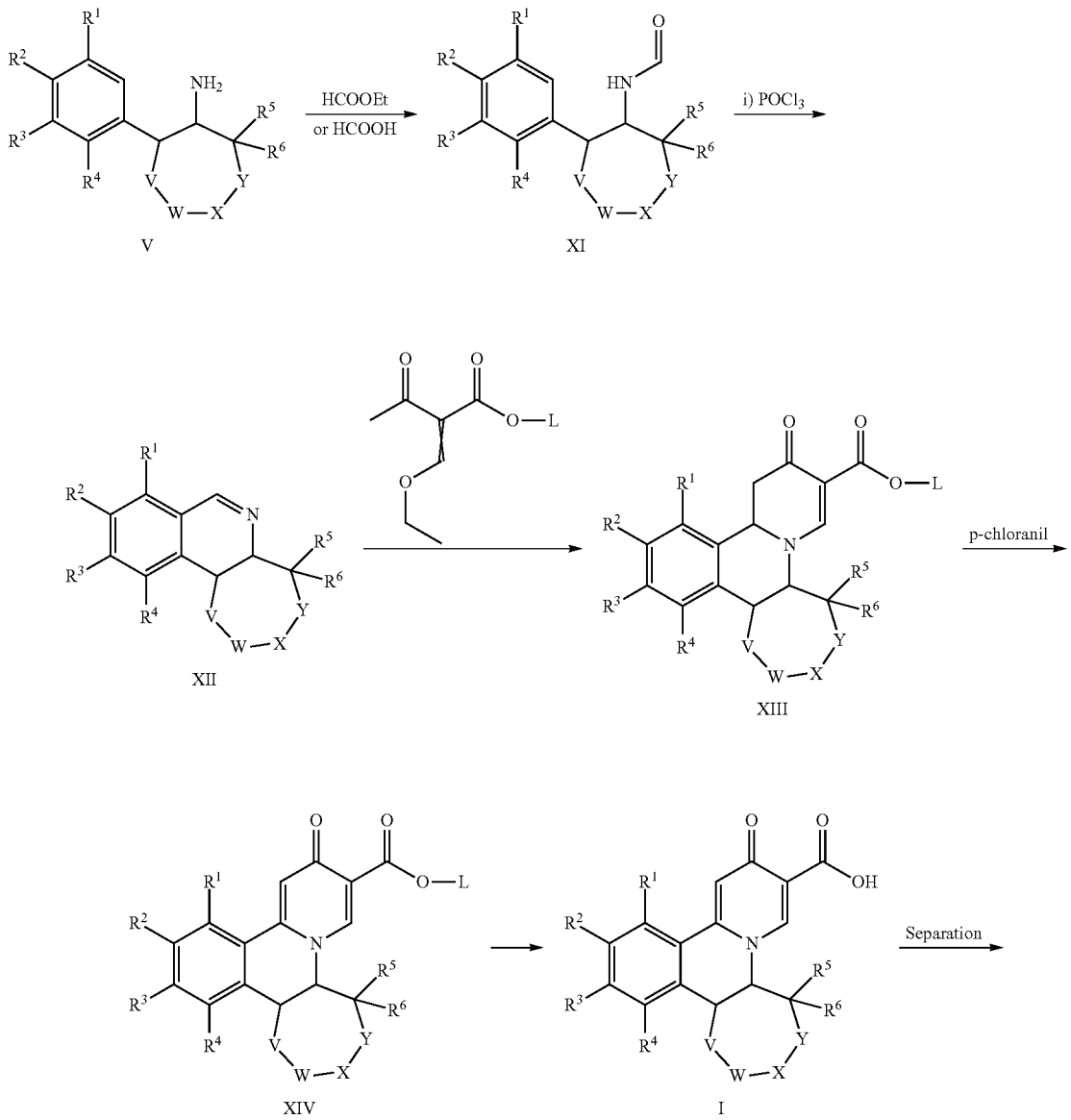

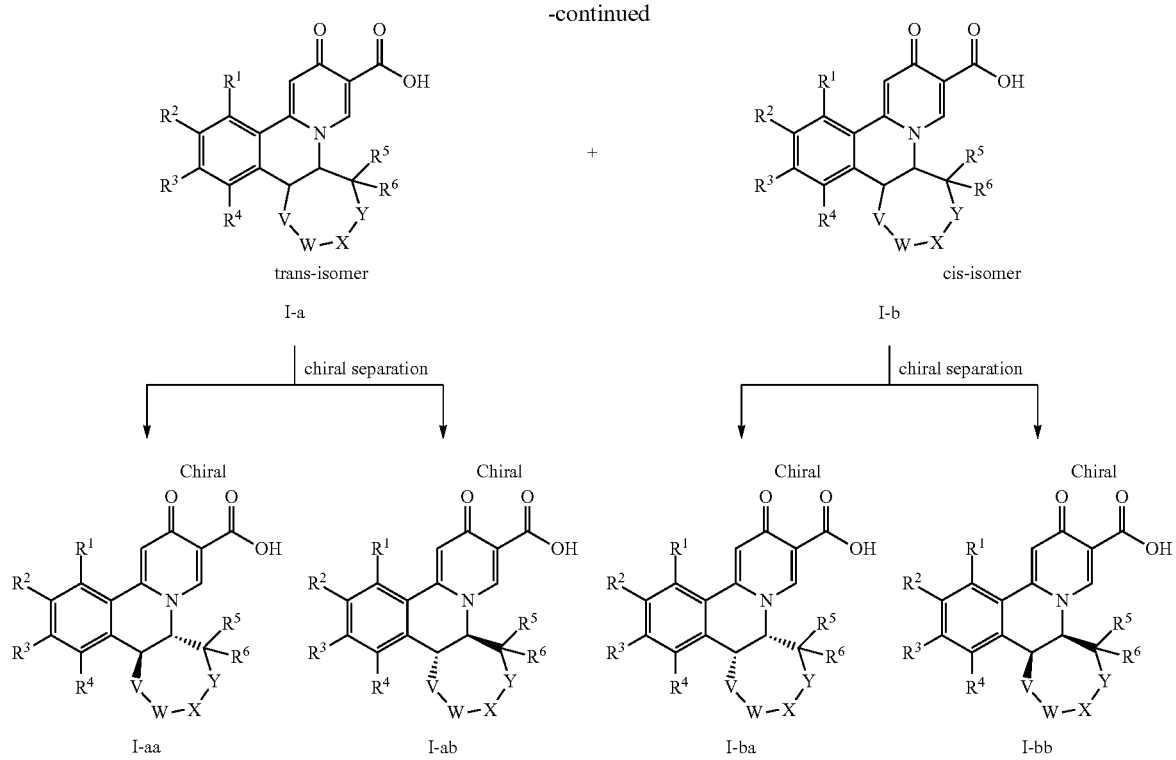

The compound of formula I, Ia, Ib, Iaa, Iab, Iba and Ibb can be prepared according to Scheme 2, wherein L is $C_{1-6}$alkyl. Compound V is heated with ethyl formate or formic acid in a solvent such as ethanol or dioxane to afford Compound XI. Compound XI is treated with $POCl_3$ in a suitable solvent such as acetonitrile or DCM at a temperature between room temperature and 100° C. to give Compound XII. Compound XII reacts with $C_{1-6}$alkyl 2-(ethoxymethylene)-3-oxo-butanoate in a solvent such as ethanol to give Compound XIII. After dehydrogenation of XIII by p-chloranil, compound XIV is obtained. Hydrolyzation of XIV by lithium hydroxide or sodium hydroxide in a suitable solvent such as $THF/H_2O$, $EtOH/H_2O$ or $MeOH/H_2O$ affords Compound I. Compound I can be separated by crystallization, or column chromatography, or preparative HPLC to give Ia and Ib, which can be further separated by chiral HPLC to give Compounds Iaa, Iab and Iba, Ibb respectively.

General Synthetic Route for Compounds I-1 (Scheme 3)

Scheme 3

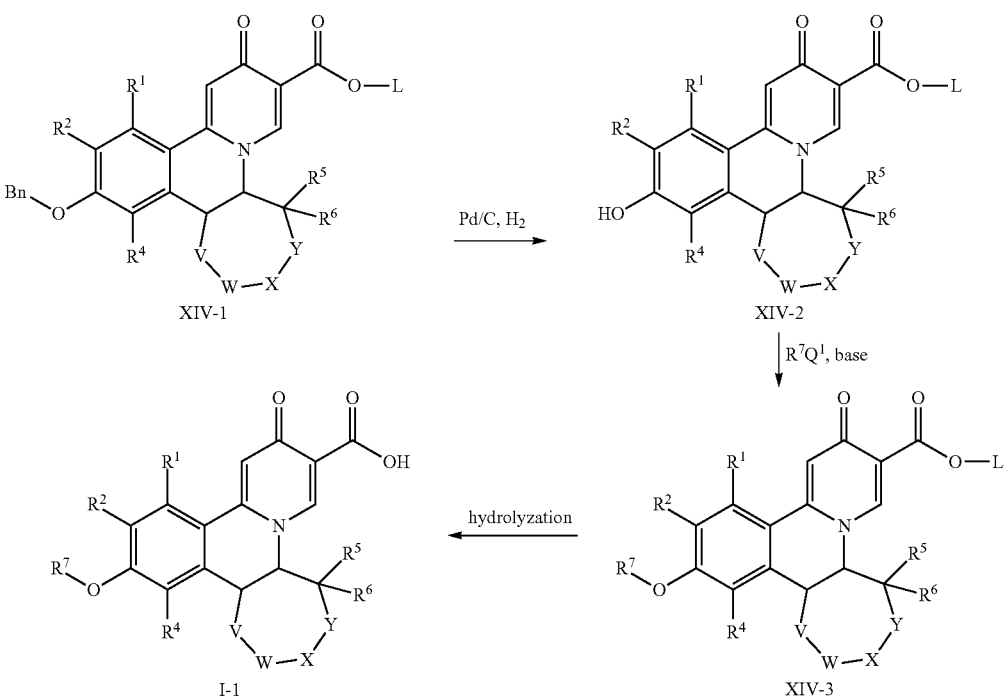

The compound of formula I-1 can be prepared according to Scheme 3, wherein $Q^1$ is halogen, —O—S(O)$_2$CH$_3$ or —O—S(O)$_2$-(4-CH$_3$-Ph); L is C$_{1-6}$alkyl. Debenzylation of Compound XIV-1 by hydrogenation is carried out in the presence of Pd/C in a solvent such as ethanol, THF, methanol to afford XIV-2. Then XIV-2 reacts with halide, mesylate or tosylate in the presence of a base such as K$_2$CO$_3$ in a solvent such as acetone or DMF to give Compound XIV-3. Hydrolyzation of XIV-3 by lithium hydroxide or sodium hydroxide in a suitable solvent such as THF/H$_2$O, EtOH/H$_2$O or MeOH/H$_2$O affords I-1.

This invention also relates to a process for the preparation of a compound of formula I comprising
(a) hydrolysis of a compound of formula (A) by using a base,

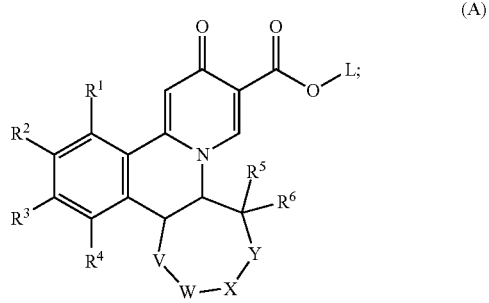

(A)

or
(b) hydrolysis of a compound of formula (B) by using a base,

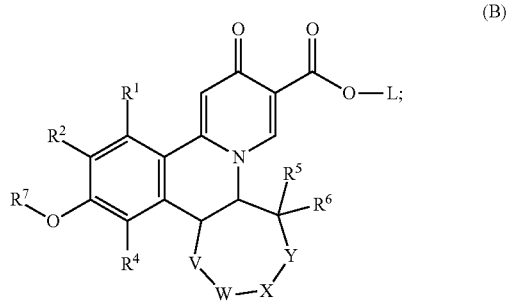

(B)

wherein $R^1$ to $R^7$, V, W, X and Y are defined above unless otherwise indicated, L is C$_{1-6}$alkyl.

In step (a) and (b) a base is for example lithium hydroxide or sodium hydroxide.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) $K_{30}$, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
$CDCl_3$: deuterated chloroform
DME: 1,2-dimethoxyethane
DMSO-$d_6$: deuterated dimethylsulfoxide
g: gram
h: hour
hrs: hours
$IC_{50}$: the half maximal inhibitory concentration
HPLC: high performance liquid chromatography
LC/MS: liquid chromatography/mass spectrometry
LiOH.$H_2O$: lithium hydroxide monohydrate
M: molarity
mg: milligram
MHz: megahertz
min: minute
mM: millimoles per liter
mm: millimeter
mmol: millimole
MS (ESI): mass spectroscopy (electron spray ionization)
NaOH: sodium hydroxide
$Na_2SO_4$: sodium sulfate
$NaBH_3CN$: sodium cyanotrihydroborate
$NaHCO_3$: sodium hydrogen carbonate
nM: nanomoles per liter
nm: nanometer
NMR: nuclear magnetic resonance
obsd. observed
rt: room temperature
Pd/C: palladium on activated carbon
$Pd(PPh_3)_4$: tetrakis(triphenylphosphine)palladium(0)
$Pd(dppf)Cl_2.CH_2Cl_2$: [1,1*-bis(diphenylphosphino)ferrocene]dichloropalladium(II), complex with dichloromethane
prep-HPLC: preparative high performance liquid chromatography
$POCl_3$: phosphorus oxychloride
TFA: trifluoroacetic acid
δ: chemical shift General Experimental Conditions Intermediates and final compounds were purified by flash chromatography using one of the following instruments: i) Biotage SP1 system and the Quad 12/25 Cartridge module.

ii) ISCO combi-flash chromatography instrument. Silica gel Brand and pore size: i) KP-SIL 60 Å, particle size: 40-60 µM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 µm, OBD™ 30×100 mm) column or SunFire™ Perp $C_{18}$ (5 µm, OBD™ 30×100 mm) column.

Chiral separation was carried out on a preparative SFC 80Q using AD-H, 250×20 mmI.D. column. Condition: A: $CO_2$; B: 0.5% diethyl amine in MeOH; gradient: B 40%.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in $H_2O$; B: 0.1% formic acid in acetonitrile;

Basic condition: A: 0.05% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty or CEM Discover.

NMR Spectra were obtained using Bruker Avance 400 MHz.

A single crystal was mounted in a loop and cooled to 160 K in a nitrogen stream. Data were collected on a Gemini R Ultra diffractometer (Oxford Diffraction, UK) with Cu—K-alpha-radiation (1.54178 Å) and processed with the Crysalis-package. Structure solution and refinement was performed using the ShelXTL software (Bruker AXS, Karlsruhe).

All reactions involving air-sensitive reagents were performed under an argon atmosphere. Reagents were used as received from commercial suppliers without further purification unless otherwise noted.

PREPARATIVE EXAMPLES

Example 1 and 2: Trans-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid and cis-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid

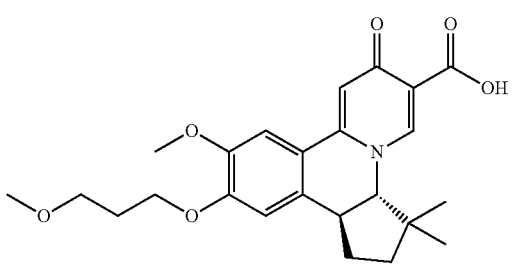

Example 1

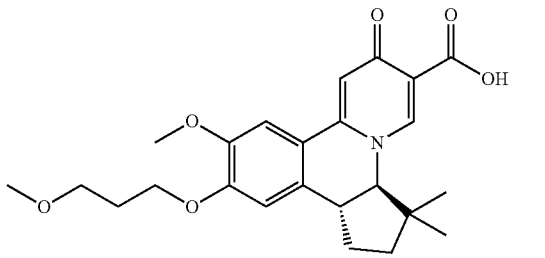

Example 2

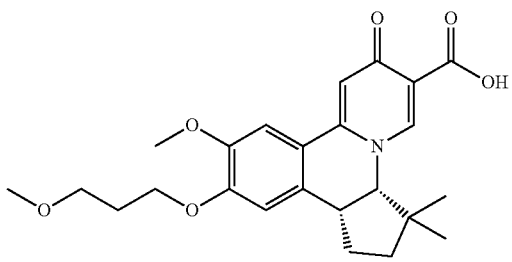

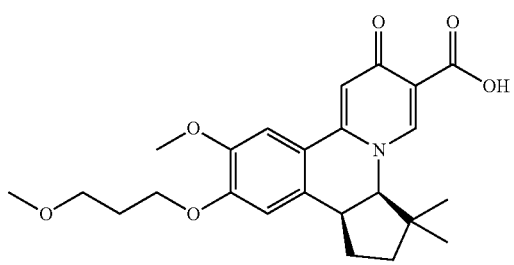

Step 1: Preparation of 5-[4-methoxy-3-(3-methoxypropoxy)phenyl]-2,2-dimethyl-cyclopentanone

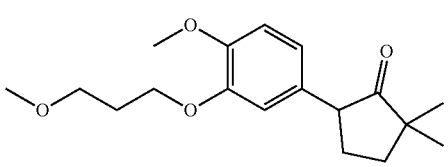

To a mixture of 4-bromo-1-methoxy-2-(3-methoxypropoxy)benzene (2.74 g, 10 mmol), tris(dibenzylideneacetone)dipalladium(0) (92 mg, 0.1 mmol), 2-dicyclohexylphosphino-2'-methylbiphenyl (73 mg, 0.2 mmol) and t-BuONa (1.92 g, 20 mmol) in THF (20 mL) was added 2,2-dimethylcyclopentanone (2.24 g, 20 mmol). The resulting mixture was heated at 50° C. for 1 hr under microwave irradiation and argon atmosphere. After being cooled to rt, the mixture was filtered. The filter cake was partitioned between water and EtOAc. The aqueous layer was extracted with EtOAc. The combined organic layers were washed with brine, dried over anhydrous $Na_2SO_4$ and concentrated under reduced pressure to give crude 5-[4-methoxy-3-(3-methoxypropoxy)phenyl]-2,2-dimethyl-cyclopentanone (2.23 g) as a yellow oil, which was directly used in the next step without further purification.

Step 2: Preparation of 5-[4-methoxy-3-(3-methoxypropoxy)phenyl]-2,2-dimethyl-cyclopentanamine

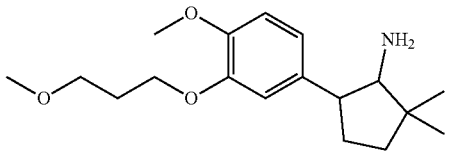

To a mixture of crude 5-[4-methoxy-3-(3-methoxypropoxy)phenyl]-2,2-dimethyl-cyclopentanone (2.51 g, 7.3 mmol) and ammonium acetate (8.43 g, 109.5 mmol) in ethanol (30 mL) was added NaBH$_3$CN (920 mg, 14.6 mmol). The resulting mixture was heated at 100° C. with stirring for 30 hrs under argon atmosphere. The reaction mixture was diluted with water, then basified with 1 M NaOH aqueous solution to pH=10-12. The resulting mixture was stirred at rt for 30 min, then extracted with CH$_2$Cl$_2$ for three times. The combined organic layers were washed with brine, dried over anhydrous Na$_2$SO$_4$, and concentrated under reduced pressure to give crude 5-[4-methoxy-3-(3-methoxypropoxy)phenyl]-2,2-dimethyl-cyclopentanamine (2.17 g) as a yellow oil, which was directly used in the next step without further purification.

Step 3: Preparation of N-[5-[4-methoxy-3-(3-methoxypropoxy)phenyl]-2,2-dimethyl-cyclopentyl]formamide

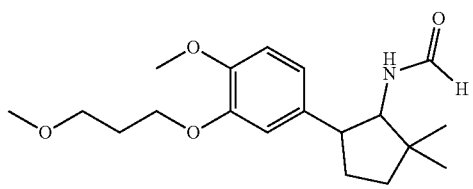 [SMILES: COCCCOc1cc(C2CCC(C)(C)C2NC=O)ccc1OC]

A solution of crude 5-[4-methoxy-3-(3-methoxypropoxy)phenyl]-2,2-dimethyl-cyclopentanamine (2.17 g, 7.1 mmol) and formic acid (0.3 mL) in ethyl formate (30 mL) was heated at 90° C. for 6 hrs. The mixture was concentrated under reduced pressure to give crude N-[5-[4-methoxy-3-(3-methoxypropoxy)phenyl]-2,2-dimethyl-cyclopentyl]formamide (2.47 g) as a yellow oil which was directly used in the next step without further purification.

Step 4: Preparation of 7-methoxy-8-(3-methoxypropoxy)-3,3-dimethyl-1,2,3a,9b-tetrahydrocyclopenta[c]isoquinoline

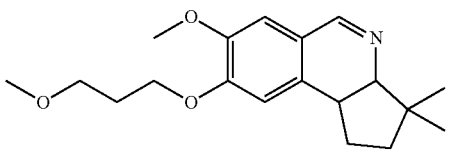

To a solution of crude N-[5-[4-methoxy-3-(3-methoxypropoxy)phenyl]-2,2-dimethyl-cyclopentyl]formamide (2.47 g, 7.1 mmol) in CH$_3$CN (20 mL) was added POCl$_3$ (1.09 g, 7.1 mmol). The reaction mixture was stirred at rt for 14 hrs, then concentrated under reduced pressure. The residue was dissolved in CH$_3$CN and then basified with ammonium hydroxide to pH=10 at 0° C. The mixture was allowed to warm to rt and stirred for 1 hr at rt. The resulting mixture was extracted with CH$_2$Cl$_2$ for three times. The combined organic layers were washed with brine, dried over anhydrous Na$_2$SO$_4$ and concentrated under reduced pressure to give crude 7-methoxy-8-(3-methoxypropoxy)-3,3-dimethyl-1,2,3a,9b-tetrahydrocyclopenta[c]isoquinoline (1.98 g) as a yellow oil which was directly used in the next step without further purification.

Step 5: Preparation of ethyl 10-methoxy-11-(3-methoxypropoxy)-3,3-dimethyl-7-oxo-1,2,3,3a,7,8,8a,12b-octahydrocyclopenta[c]pyrido[2,1-a]isoquinoline-6-carboxylate

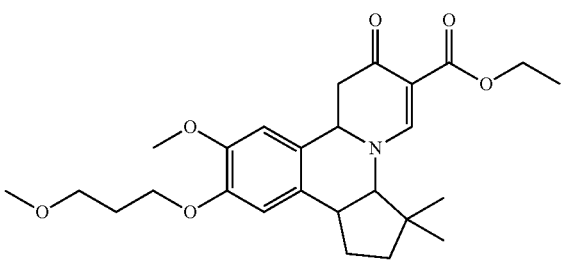 [SMILES: CCOC(=O)C1=CN2C(CC1=O)c1cc(OC)c(OCCCOC)cc1C1CCC(C)(C)C12]

A mixture of crude 7-methoxy-8-(3-methoxypropoxy)-3,3-dimethyl-1,2,3a,9b-tetrahydrocyclopenta[c]isoquinoline (1.98 g, 6.25 mmol) and ethyl 2-(ethoxymethylene)-3-oxobutanoate (3.49 g, 18.75 mmol) in ethanol (20 mL) was heated at 100° C. with stirring for 16 hrs. The mixture was concentrated under reduced pressure to give crude ethyl 10-methoxy-11-(3-methoxypropoxy)-3,3-dimethyl-7-oxo-1,2,3,3a,7,8,8a,12b-octahydrocyclopenta[c]pyrido[2,1-a]isoquinoline-6-carboxylate (5.16 g) as a brown oil which was directly used in the next step without further purification.

Step 6: Preparation of trans-ethyl 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate and cis-ethyl 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate

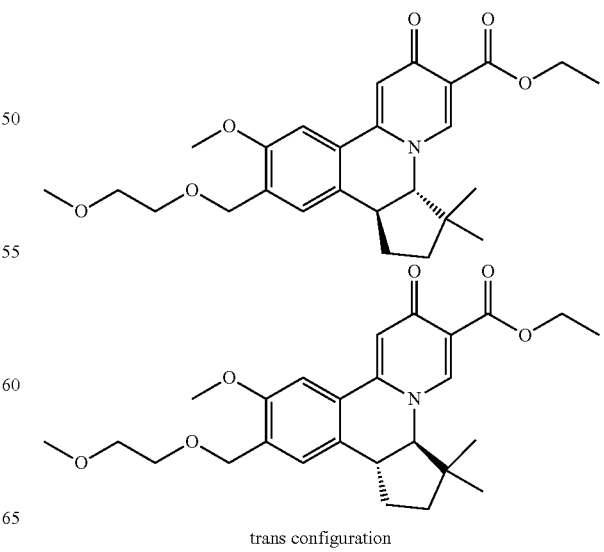

trans configuration

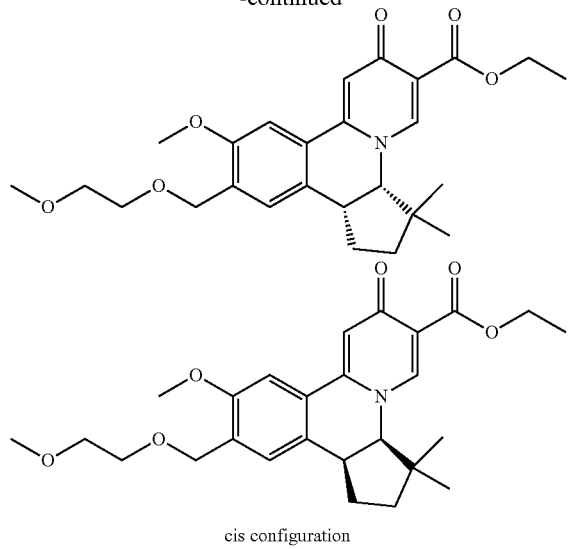

cis configuration

A mixture of crude ethyl 10-methoxy-11-(3-methoxypropoxy)-3,3-dimethyl-7-oxo-1,2,3,3a,7,8,8a,12b-octahydrocyclopenta[c]pyrido[2,1-a]isoquinoline-6-carboxylate (5.16 g, 6.25 mmol) and p-chloranil (1.54 g, 6.25 mmol) in DME (20 mL) was heated at 70° C. for 3 hrs under argon atmosphere. After being cooled to rt, the mixture was filtered. The filter cake was dried to give trans-ethyl 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate (930 mg) as a yellow solid. The filtrate was concentrated to give crude cis-ethyl 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate (6.13 g) as a brown oil which was directly used in the next step without further purification.

Step 7: Preparation of trans-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid and cis-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid Example 1

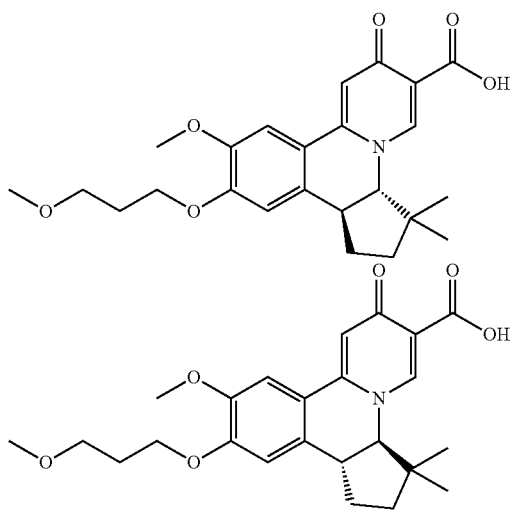

Example 2

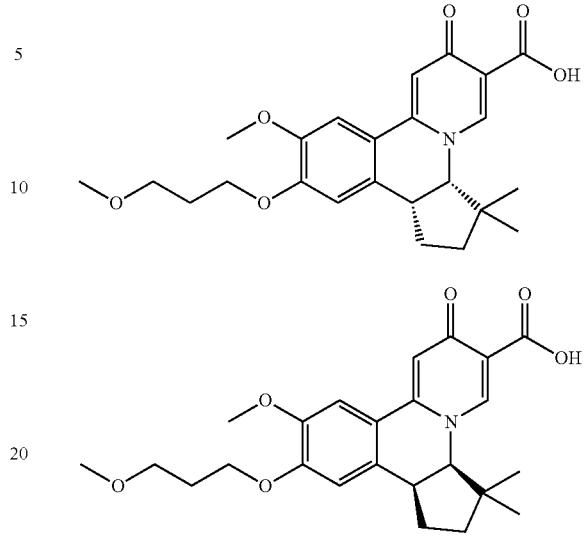

To a solution of crude trans-ethyl 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate (930 mg, 2 mmol) in methanol (8 mL) and H$_2$O (2 mL) was added LiOH.H$_2$O (672 mg, 16 mmol). The resulting mixture was stirred at rt for 3 hrs, then acidified with 1 M hydrochloric acid to pH=2-3. The resulting mixture was extracted with CH$_2$Cl$_2$ for three times. The combined organic layers were washed with brine, dried over anhydrous Na$_2$SO$_4$ and concentrated under reduced pressure. The residue was treated with diethyl ether to afford trans-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid (290 mg, Example 1) as a yellow solid. $^1$H NMR (400 MHz, DMSO-d$_6$): δ ppm 8.59 (s, 1H), 7.50 (s, 2H), 6.85 (s, 1H), 4.13 (m, 2H), 3.90-3.82 (m, 4H), 3.50-3.44 (m, 3H), 3.26 (s, 3H), 2.32-2.19 (m, 1H), 1.99 (quin, 2H), 1.94-1.77 (m, 3H), 1.47 (s, 3H), 1.24 (s, 3H). MS obsd. (EsI$^+$) [(M+H)$^+$]: 428.

To a solution of crude cis-ethyl 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate (6.13 g, 2 mmol) in methanol (16 mL) and H$_2$O (4 mL) was added LiOH.H$_2$O (2.02 g, 48 mmol). The resulting mixture was stirred at rt for 5 hrs, then acidified with 1 M hydrochloric acid to pH=2-3, and extracted with CH$_2$Cl$_2$ for three times. The combined organic layers were washed with brine, dried over anhydrous Na$_2$SO$_4$ and concentrated under reduced pressure. The residue was treated with diethyl ether to afford cis-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid (309 mg, Example 2) as a yellow solid. $^1$H NMR (400 MHz, DMSO-d$_6$): δ ppm 8.53 (s, 1H), 7.58 (s, 1H), 7.52 (s, 1H), 7.01 (s, 1H), 4.63 (d, 1H), 4.20-4.06 (m, 2H), 3.89 (s, 3H), 3.76 (t, 1H), 3.48 (t, 2H), 3.26 (s, 3H), 2.33-2.19 (m, 2H), 1.98 (quin, 2H), 1.63-1.53 (m, 1H), 1.36 (td, 1H), 1.16 (s, 3H), 0.40 (s, 3H). MS obsd. (ESI$^+$) [(M+H)$^+$]: 428.

Example 3: Cis-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid

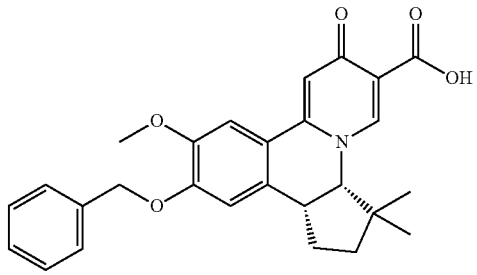

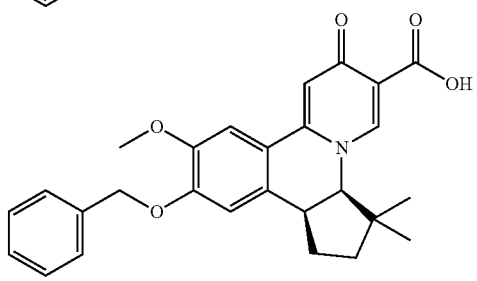

Step 1: Preparation of 2-benzyloxy-4-bromo-1-methoxy-benzene

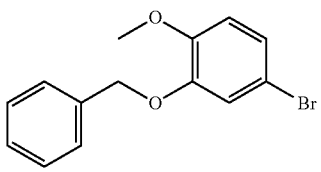 [SMILES: COc1ccc(Br)cc1OCc1ccccc1]

To a mixture of 5-bromo-2-methoxy-phenol (40.6 g, 200 mmol), $K_2CO_3$ (55.2 g, 400 mmol) in $CH_3CN$ (300 mL) and DMF (100 mL) was added benzyl bromide (35.9 g, 210 mmol). The mixture was stirred at rt overnight, then partitioned between $CH_2Cl_2$ and water. The separated aqueous layer was extracted with $CH_2Cl_2$ for three times. The combined organic layers were washed with brine, dried over anhydrous $Na_2SO_4$ and concentrated under reduced pressure to give crude 2-benzyloxy-4-bromo-1-methoxy-benzene (62.6 g) as a yellow solid which was directly used in the next step without further purification.

Step 2: Preparation of 5-(3-benzyloxy-4-methoxy-phenyl)-2,2-dimethyl-cyclopentanone

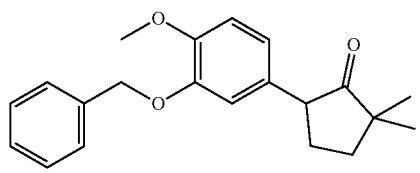 [SMILES: COc1ccc(C2CCC(C)(C)C2=O)cc1OCc1ccccc1]

To a mixture of 2-benzyloxy-4-bromo-1-methoxy-benzene (53.5 g, 183 mmol), tris(dibenzylideneacetone)dipalladium(0) (3.4 g, 3.7 mmol), 2-dicyclohexylphosphino-2'-methylbiphenyl (2.7 g, 7.4 mmol) and t-BuONa (22.8 g, 238 mmol) in THF (600 mL) was added 2,2-dimethylcyclopentanone (24.6 g, 220 mmol). The resulting mixture was heated at 60° C. for 3.5 hrs under argon atmosphere. After being cooled to rt, the mixture was filtered. The filtrate was diluted with water and acidified with 2 M hydrochloric acid. The resulting mixture was extracted with diethyl ether for three times. The combined organic layers were washed with brine, dried over anhydrous $Na_2SO_4$ and concentrated under reduced pressure to give crude 5-(3-benzyloxy-4-methoxy-phenyl)-2,2-dimethyl-cyclopentanone (58.5 g) as a brown oil which was directly used in the next step without further purification.

Step 3: Preparation of 5-(3-benzyloxy-4-methoxy-phenyl)-2,2-dimethyl-cyclopentanamine

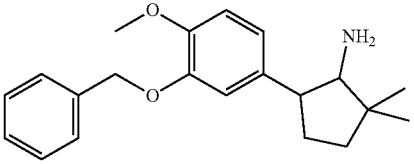 [SMILES: COc1ccc(C2CCC(C)(C)C2N)cc1OCc1ccccc1]

To a mixture of crude 5-(3-benzyloxy-4-methoxy-phenyl)-2,2-dimethyl-cyclopentanone (58.5 g, 181 mmol) and ammonium acetate (209 g, 2720 mmol) in ethanol (500 mL) was added $NaBH_3CN$ (22.8 g, 362 mmol). The resulting mixture was heated at 90° C. for 16 hrs under argon atmosphere, then to the reaction mixture were added additional ammonium acetate (69 g, 896 mmol) and $NaBH_3CN$ (5.7 g, 90 mmol) successively. The resulting mixture was heated at 100° C. for additional 40 hrs. After being cooled to rt, the mixture was diluted with water, then basified with 2 M NaOH aqueous solution to pH=10-12, and extracted with $CH_2Cl_2$ for three times. The combined organic lays were washed with water, brine, dried over anhydrous $Na_2SO_4$ and concentrated under reduced pressure to give crude 5-(3-benzyloxy-4-methoxy-phenyl)-2,2-dimethyl-cyclopentanamine (60.0 g) as a yellow oil which was directly used in the next step without further purification.

Step 4: Preparation of N-[5-(3-benzyloxy-4-methoxy-phenyl)-2,2-dimethyl-cyclopentyl]formamide

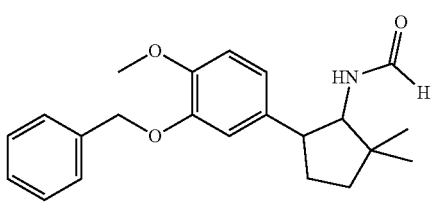 [SMILES: COc1ccc(C2CCC(C)(C)C2NC=O)cc1OCc1ccccc1]

A solution of crude 5-(3-benzyloxy-4-methoxy-phenyl)-2,2-dimethyl-cyclopentanamine (60.0 g, 181 mmol) and formic acid (3 mL) in ethyl formate (300 mL) was heated at 90° C. for 16 hrs. The mixture was concentrated under reduced pressure to give crude N-[5-(3-benzyloxy-4-methoxy-phenyl)-2,2-dimethyl-cyclopentyl]formamide (61.9 g) as a yellow oil which was directly used in the next step without further purification.

Step 5: Preparation of 8-benzyloxy-7-methoxy-3,3-dimethyl-1,2,3a,9b-tetrahydrocyclopenta[c]isoquinoline

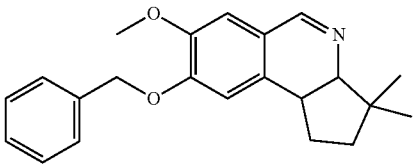 [SMILES: COc1cc2c(cc1OCc1ccccc1)C1CCC(C)(C)C1N=C2]

To a solution of crude N-[5-(3-benzyloxy-4-methoxy-phenyl)-2,2-dimethyl-cyclopentyl]formamide (61.9 g, 175 mmol) in CH$_3$CN (400 mL) was added POCl$_3$ (26.8 g, 175 mmol). The reaction mixture was stirred at rt for 20 hrs under argon atmosphere, then concentrated under reduced pressure. The residue was dissolved in CH$_3$CN and then basified with ammonium hydroxide to pH=10 at 0° C. The resulting mixture was allowed to warm to rt and stirred at rt for 1 hr, and then extracted with CH$_2$Cl$_2$ for three times. The combined organic layers were washed with brine, dried over anhydrous Na$_2$SO$_4$ and concentrated under reduced pressure to give crude 8-benzyloxy-7-methoxy-3,3-dimethyl-1,2,3a,9b-tetrahydrocyclopenta[c]isoquinoline (42.5 g) as a brown oil which was directly used in the next step without further purification.

Step 6: Preparation of ethyl 11-(benzyloxy)-10-methoxy-3,3-dimethyl-7-oxo-1,2,3,3a,7,8,8a,12b-octahydrocyclopenta[c]pyrido[2,1-a]isoquinoline-6-carboxylate

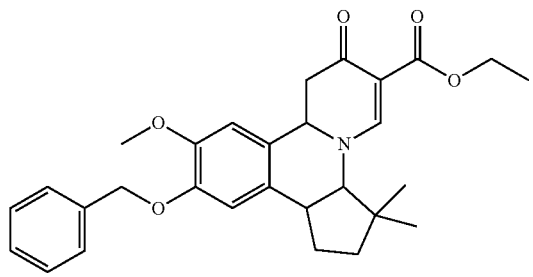 [SMILES: CCOC(=O)C1=CN2C(CC1=O)c1cc(OC)c(OCc3ccccc3)cc1C1CCC(C)(C)C12]

A mixture of crude 8-benzyloxy-7-methoxy-3,3-dimethyl-1,2,3a,9b-tetrahydrocyclopenta[c]isoquinoline (42.5 g, 127 mmol) and ethyl 2-(ethoxymethylene)-3-oxo-butanoate (70.9 g, 381 mmol) in ethanol (400 mL) was heated at 100° C. for 48 hrs under argon atmosphere. The mixture was concentrated under reduced pressure to give crude ethyl 11-(benzyloxy)-10-methoxy-3,3-dimethyl-7-oxo-1,2,3,3a,7,8,8a,12b-octahydrocyclopenta[c]pyrido[2,1-a]isoquinoline-6-carboxylate (126.8 g) as a red oil which was directly used in the next step without further purification.

Step 7: Preparation of cis-ethyl 11-(benzyloxy)-10-methoxy-3,3-dimethyl-7-oxo-1,2,3,3a,7,12b-hexahydrocyclopenta[c]pyrido[2,1-a]isoquinoline-6-carboxylate

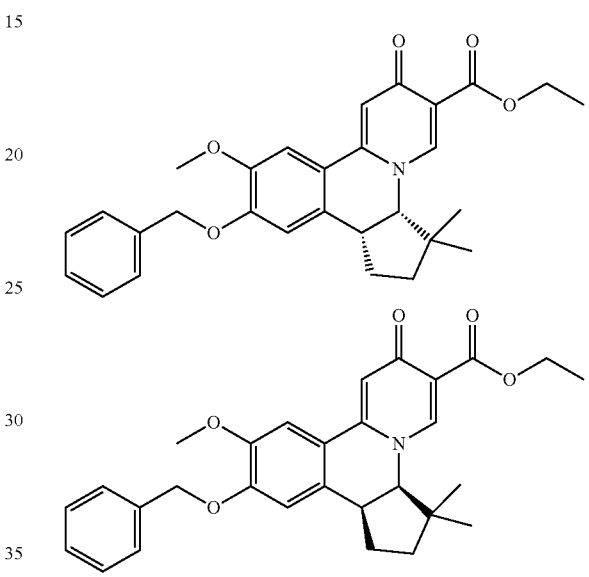

A mixture of crude ethyl 11-(benzyloxy)-10-methoxy-3,3-dimethyl-7-oxo-1,2,3,3a,7,8,8a,12b-octahydrocyclopenta[c]pyrido[2,1-a]isoquinoline-6-carboxylate (126.8 g, 127 mmol) and p-chloranil (31.2 g, 127 mmol) in DME (200 mL) was heated at 70° C. for 4 hrs. The resulting mixture was concentrated under reduced pressure, and the residue was dissolved in DME (100 mL). The resulting solution was stirred at rt for 1 h, and then filtered. The filtrate was concentrated under reduced pressure and the residue was dissolved in 2-methyltetrahydrofuran (300 mL). To the above solution was added saturated NaHCO$_3$ aqueous solution (200 mL). The resulting mixture was stirred for 30 min. The separated organic layer was washed with saturated NaHCO$_3$ aqueous solution (200 mL) twice and 4 M hydrochloric acid (75 mL) for three times. The combined acidic aqueous layers were basified with 4 M NaOH aqueous to pH=9 at 0° C., and then extracted with CH$_2$Cl$_2$ (200 mL) for three times. The combined organic layers were washed with brine, dried over anhydrous Na$_2$SO$_4$ and concentrated under reduced pressure to give cis-ethyl 11-(benzyloxy)-10-methoxy-3,3-dimethyl-7-oxo-1,2,3,3a,7,12b-hexahydrocyclopenta[c]pyrido[2,1-a]isoquinoline-6-carboxylate (9.87 g) as a brown solid which was directly used in the next step without further purification.

Step 8: Preparation of cis-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid

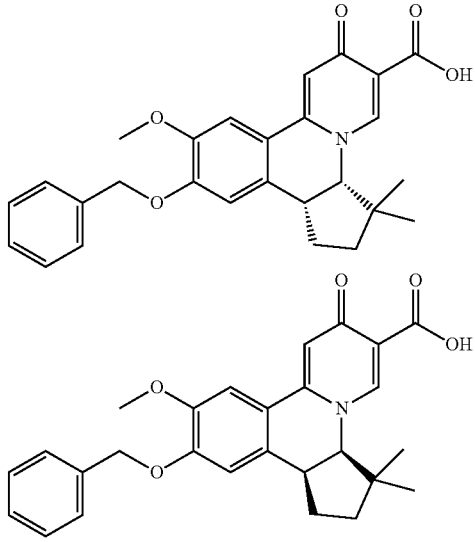

To a solution of crude cis-ethyl 11-(benzyloxy)-10-methoxy-3,3-dimethyl-7-oxo-1,2,3,3a,7,12b-hexahydrocyclopenta[c]pyrido[2,1-a]isoquinoline-6-carboxylate (2.17 g, 4.6 mmol) in methanol (16 mL) and H$_2$O (4 mL) was added LiOH.H$_2$O (773 mg, 18.4 mmol). The resulting mixture was stirred at rt for 3 hrs, then diluted with water and acidified with 1 M hydrochloric acid to pH=2-3. The resulting mixture was stirred at rt for 30 min and filtered. The filter cake was washed with water, dried and purified by prep-HPLC to afford cis-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid (420 mg) as a yellow solid. $^1$H NMR (400 MHz, DMSO-d$_6$): δ ppm 8.54 (s, 1H), 7.60 (s, 1H), 7.54 (s, 1H), 7.50-7.45 (m, 2H), 7.42 (t, 2H), 7.38-7.33 (m, 1H), 7.12 (s, 1H), 5.30-5.16 (m, 2H), 4.63 (d, 1H), 3.90 (s, 3H), 3.75 (t, 1H), 2.24 (t, 2H), 1.56 (ddd, 1H), 1.30 (td, 1H), 1.16 (s, 3H), 0.38 (s, 3H). MS obsd. (ESI$^+$) [(M+H)$^+$]: 446.

Example 4 and 5: (3aS,12bR)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid and (3aR,12bS)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid Example 4

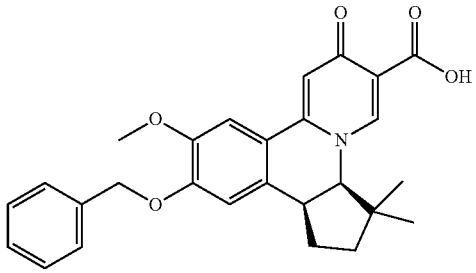

Example 5

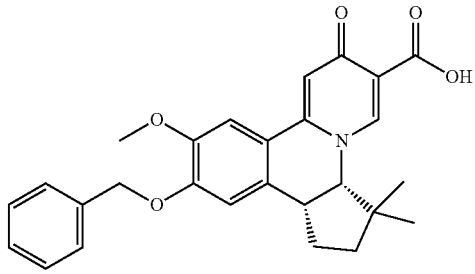

Separation of the two enantiomers from cis-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid by chiral HPLC afforded (3aS,12bR)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid and (3aR,12bS)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid.

Example 4

$^1$H NMR (400 MHz, DMSO-d$_6$) δ ppm 8.54 (s, 1H), 7.59 (s, 1H), 7.54 (s, 1H), 7.50-7.45 (m, 2H), 7.42 (t, 2H), 7.38-7.33 (m, 1H), 7.12 (s, 1H), 5.31-5.15 (m, 2H), 4.62 (d, 1H), 3.89 (s, 3H), 3.75 (br. s., 1H), 2.23 (m, 2H), 1.63-1.50 (m, 1H), 1.36-1.24 (m, 1H), 1.15 (s, 3H), 0.37 (s, 3H). MS obsd. (ESI$^+$) [(M+H)$^+$]: 446. The absolute stereochemistry was determined by the X-ray diffraction study (FIG. 1).

Example 5

$^1$H NMR (400 MHz, DMSO-d$_6$) δ ppm 8.54 (s, 1H), 7.61-7.33 (m, 7H), 7.11 (s, 1H), 5.32-5.14 (m, 2H), 4.62 (m, 1H), 3.89 (s, 3H), 3.75 (br. s., 1H), 2.24 (m, 2H), 1.60-1.48 (m, 1H), 1.35-1.23 (m, 1H), 1.15 (s, 3H), 0.37 (s, 3H). MS obsd. (ESI$^+$) [(M+H)$^+$]: 446.

Example 6: Cis-11-hydroxy-10-methoxy-3,3-dimethyl-7-oxo-1,2,3,3a,7,12b-hexahydrocyclopenta[c]pyrido[2,1-a]isoquinoline-6-carboxylic acid

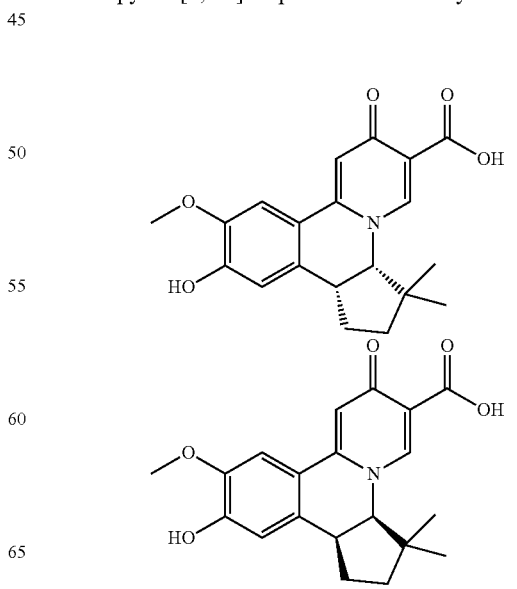

Step 1: Preparation of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate

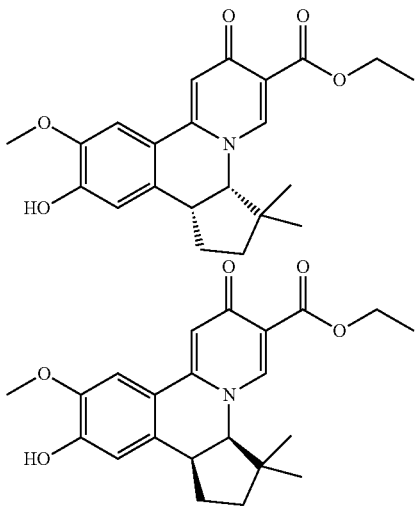

A mixture of cis-ethyl 11-(benzyloxy)-10-methoxy-3,3-dimethyl-7-oxo-1,2,3,3a,7,12b-hexahydrocyclopenta[c]pyrido[2,1-a]isoquinoline-6-carboxylate (7.7 g, 16.3 mmol) and 10 wt. % palladium on carbon (770 mg) in ethanol (300 mL) was stirred at rt for 64 hrs under hydrogen atmosphere by using a hydrogen balloon. The reaction mixture was filtered, and then the filtrate was concentrated under reduced pressure to give crude cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (6.3 g) as a dark brown oil which was directly used in the next step without further purification.

Step 2: Preparation of cis-11-hydroxy-10-methoxy-3,3-dimethyl-7-oxo-1,2,3,3a,7,12b-hexahydrocyclopenta[c]pyrido[2,1-a]isoquinoline-6-carboxylic acid

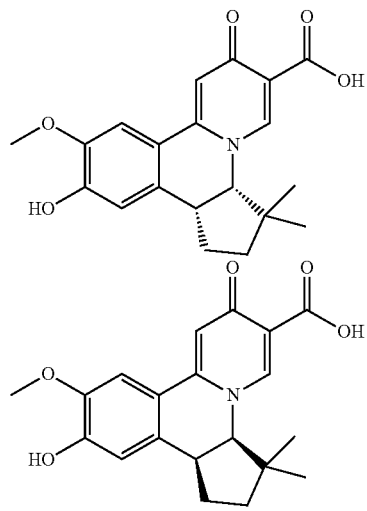

To a solution of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (76 mg, 0.2 mmol) in methanol (3 mL) and $H_2O$ (1 mL) was added $LiOH \cdot H_2O$ (34 mg, 0.8 mmol). The mixture was stirred at rt overnight, then diluted with water and acidified with 2 M hydrochloric acid to pH=2-3. The resulting mixture was extracted with $CH_2Cl_2$ for three times. The combined organic layers were washed with brine, dried over anhydrous $Na_2SO_4$ and concentrated under reduced pressure. The residue was purified by prep-HPLC to afford cis-11-hydroxy-10-methoxy-3,3-dimethyl-7-oxo-1,2,3,3a,7,12b-hexahydrocyclopenta[c]pyrido[2,1-a]isoquinoline-6-carboxylic acid (9 mg) as a yellow solid. $^1H$ NMR (400 MHz, DMSO-$d_6$) δ ppm 8.51 (s, 1H), 7.53 (s, 1H), 7.51 (s, 1H), 6.85 (s, 1H), 4.59 (d, 1H), 3.89 (s, 3H), 3.75-3.65 (m, 1H), 2.28-2.08 (m, 2H), 1.63-1.52 (m, 1H), 1.42-1.30 (m, 1H), 1.15 (s, 3H), 0.39 (s, 3H). MS obsd. (ESI$^+$) [(M+H)$^+$]: 356.

Example 7: Cis-10,11-dimethoxy-3,3-dimethyl-7-oxo-1,2,3,3a,7,12b-hexahydrocyclopenta[c]pyrido[2,1-a]isoquinoline-6-carboxylic acid

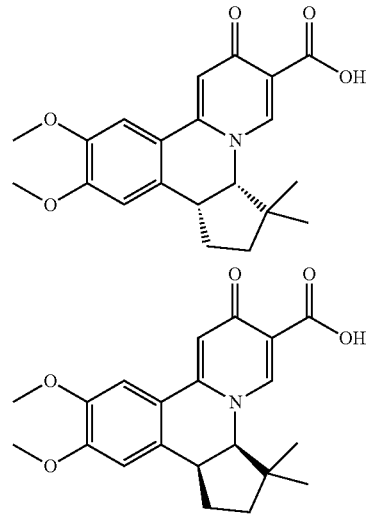

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added iodomethane (207 mg, 1.8 mmol). The mixture was stirred at rt overnight. To the above mixture was added LiOH aqueous solution (0.5 mL, 1.2 mmol). The resulting mixture was stirred at rt for 2 hrs, then acidified with 2 M hydrochloric acid to pH=2-3, and extracted with $CH_2Cl_2$ for three times. The combined organic layers were washed with brine, dried over anhydrous $Na_2SO_4$ and concentrated under reduced pressure. The residue was purified by prep-HPLC to afford cis-10,11-dimethoxy-3,3-dimethyl-7-oxo-1,2,3,3a,7,12b-hexahydrocyclopenta[c]pyrido[2,1-a]isoquinoline-6-carboxylic acid (22 mg) as a white solid. $^1H$ NMR (400 MHz, DMSO-$d_6$) δ ppm 8.54 (s, 1H), 7.59 (s, 1H), 7.52 (s, 1H), 7.01 (s, 1H), 4.64 (d, 1H), 3.90-3.88 (m, 3H), 3.88-3.86 (m, 3H), 3.81-3.74 (m, 1H), 2.37-2.21 (m, 2H), 1.59 (ddd, 1H), 1.37 (td, 1H), 1.16 (s, 3H), 0.40 (s, 3H). MS obsd. (ESI$^+$) [(M+H)$^+$]: 370.

Example 8: Cis-10-methoxy-3,3-dimethyl-7-oxo-11-(2,2,2-trifluoroethoxy)-1,2,3,3a,7,12b-hexahydrocyclopenta[c]pyrido[2,1-a]isoquinoline-6-carboxylic acid

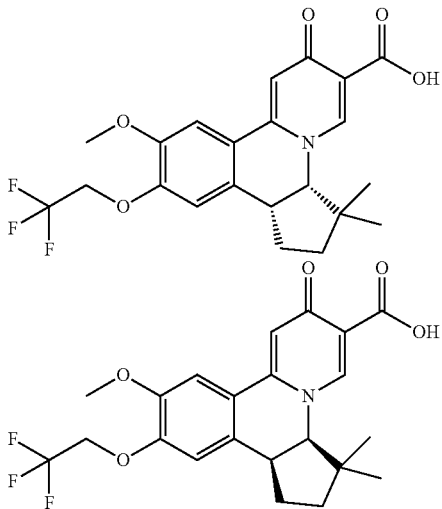

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added 1,1,1-trifluoro-2-iodo-ethane (315 mg, 1.5 mmol). The resulting mixture was heated at 120° C. with stirring for 4 hrs, and then cooled to rt. To the above mixture was added LiOH aqueous solution (2.4 M, 0.5 mL, 1.2 mmol). The reaction mixture was stirred at rt for 16 hrs, then acidified with 2 M hydrochloric acid to pH=2-3, and extracted with $CH_2Cl_2$ for three times. The combined organic layers were washed with brine, dried over anhydrous $Na_2SO_4$ and concentrated under reduced pressure. The residue was purified by prep-HPLC to afford cis-10-methoxy-3,3-dimethyl-7-oxo-11-(2,2,2-trifluoroethoxy)-1,2,3,3a,7,12b-hexahydrocyclopenta[c]pyrido[2,1-a]isoquinoline-6-carboxylic acid (13 mg) as a white solid. $^1$H NMR (400 MHz, DMSO-d$_6$) δ ppm 8.56 (s, 1H), 7.65 (s, 1H), 7.60 (s, 1H), 7.17 (s, 1H), 5.00-4.79 (m, 2H), 4.65 (d, 1H), 3.93 (s, 3H), 3.76 (t, 1H), 2.41-2.30 (m, 1H), 2.28-2.17 (m, 1H), 1.59 (ddd, 1H), 1.36 (td, 1H), 1.17 (s, 3H), 0.40 (s, 3H). MS obsd. (ESI$^+$) [(M+H)$^+$]: 438.

Example 9: Cis-11-isobutoxy-10-methoxy-3,3-dimethyl-7-oxo-1,2,3,3a,7,12b-hexahydrocyclopenta[c]pyrido[2,1-a]isoquinoline-6-carboxylic acid

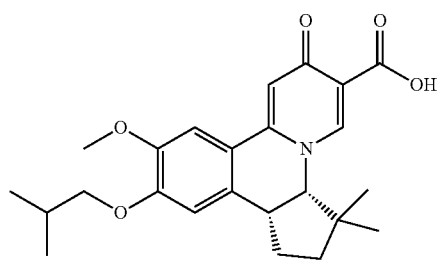

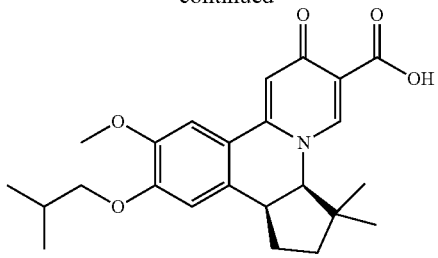

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added 1-iodo-2-methyl-propane (166 mg, 0.9 mmol). The resulting mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with 2 M hydrochloric acid to pH=2-3 and extracted with $CH_2Cl_2$ for three times. The combined organic layers were washed with brine, dried over anhydrous $Na_2SO_4$ and concentrated under reduced pressure. The residue was purified by prep-HPLC to afford cis-11-isobutoxy-10-methoxy-3,3-dimethyl-7-oxo-1,2,3,3a,7,12b-hexahydrocyclopenta[c]pyrido[2,1-a]isoquinoline-6-carboxylic acid (21 mg) as a yellow solid. $^1$H NMR (400 MHz, DMSO-d$_6$) δ ppm 8.54 (s, 1H), 7.58 (s, 1H), 7.52 (s, 1H), 6.99 (s, 1H), 4.63 (d, 1H), 3.89 (s, 3H), 3.88-3.80 (m, 2H), 3.76 (t, 1H), 2.37-2.20 (m, 2H), 2.13-1.99 (m, 1H), 1.58 (ddd, 1H), 1.36 (td, 1H), 1.16 (s, 3H), 1.01 (d, 3H), 0.99 (d, 3H), 0.40 (s, 3H). MS obsd. (ESI$^+$) [(M+H)$^+$]: 412.

Example 10: Cis-11-(cyclopropylmethoxy)-10-methoxy-3,3-dimethyl-7-oxo-1,2,3,3a,7,12b-hexahydrocyclopenta[c]pyrido[2,1-a]isoquinoline-6-carboxylic acid

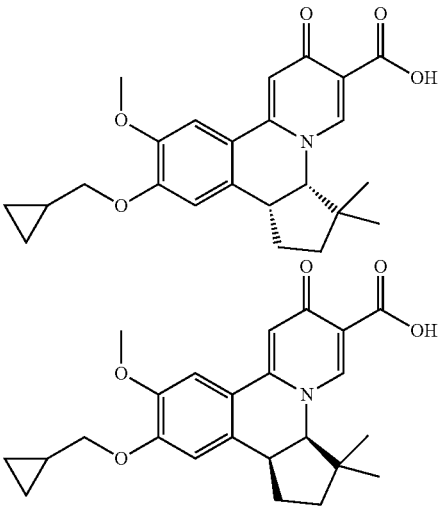

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added bromomethylcyclopropane (122 mg, 0.9 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with 2 M hydrochloric acid to pH=2-3 and extracted with CH$_2$Cl$_2$ for three times. The combined organic layers were washed with brine, dried over anhydrous Na$_2$SO$_4$ and concentrated under reduced pressure. The reside was purified by prep-HPLC to afford cis-11-(cyclopropylmethoxy)-10-methoxy-3,3-dimethyl-7-oxo-1,2,3,3a,7,12b-hexahydrocyclopenta[c]pyrido[2,1-a]isoquinoline-6-carboxylic acid (27 mg) as a yellow solid. $^1$H NMR (400 MHz, DMSO-d$_6$) δ ppm 8.53 (s, 1H), 7.58 (s, 1H), 7.51 (s, 1H), 6.96 (s, 1H), 4.62 (d, 1H), 3.96-3.91 (m, 2H), 3.90 (s, 3H), 3.78-3.71 (m, 1H), 2.34-2.17 (m, 2H), 1.57 (ddd, 1H), 1.35 (td, 1H), 1.29-1.20 (m, 1H), 1.16 (s, 3H), 0.60 (dd, 2H), 0.40 (s, 3H), 0.35 (q, 2H). MS obsd. (ESI$^+$) [(M+H)$^+$]: 410.

Example 11: Cis-10-methoxy-11-(2-methoxyethoxy)-3,3-dimethyl-7-oxo-1,2,3,3a,7,12b-hexahydrocyclopenta[c]pyrido[2,1-a]isoquinoline-6-carboxylic acid

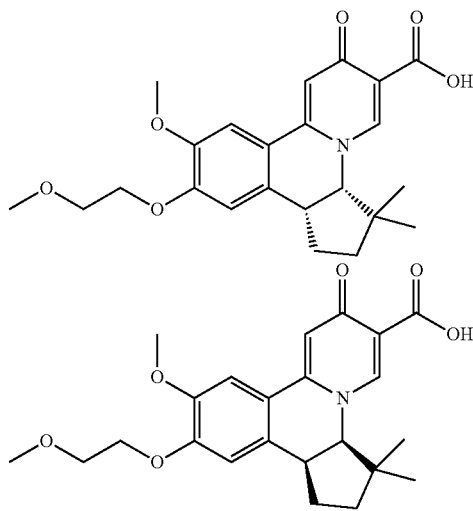

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and K$_2$CO$_3$ (83 mg, 0.6 mmol) in DMF (2 mL) was added 1-bromo-2-methoxy-ethane (292 mg, 2.1 mmol). The mixture was stirred at rt for 40 hrs. To the above mixture was added LiOH. H$_2$O (50 mg, 1.2 mmol) and H$_2$O (1 mL). The resulting mixture was stirred at rt for 2 hrs, then acidified with 2 M hydrochloric acid to pH=2-3 and extracted with CH$_2$Cl$_2$ for three times. The combined organic layers were washed with brine, dried over anhydrous Na$_2$SO$_4$ and concentrated under reduced pressure. The residue was purified by prep-HPLC to afford cis-10-methoxy-11-(2-methoxyethoxy)-3,3-dimethyl-7-oxo-1,2,3,3a,7,12b-hexahydrocyclopenta[c]pyrido[2,1-a]isoquinoline-6-carboxylic acid (26 mg) as a white solid. $^1$H NMR (400 MHz, DMSO-d$_6$) δ ppm 8.53 (s, 1H), 7.59 (s, 1H), 7.52 (s, 1H), 7.03 (s, 1H), 4.63 (d, 1H), 4.29-4.15 (m, 2H), 3.89 (s, 3H), 3.76 (t, 1H), 3.69 (t, 2H), 3.32 (s, 3H), 2.37-2.18 (m, 2H), 1.58 (ddd, 1H), 1.36 (td, 1H), 1.16 (s, 3H), 0.40 (s, 3H). MS obsd. (ESI$^+$) [(M+H)$^+$]: 414.

Example 12: Cis-11-(3-cyanopropoxy)-10-methoxy-3,3-dimethyl-7-oxo-1,2,3,3a,7,12b-hexahydrocyclopenta[c]pyrido[2,1-a]isoquinoline-6-carboxylic acid

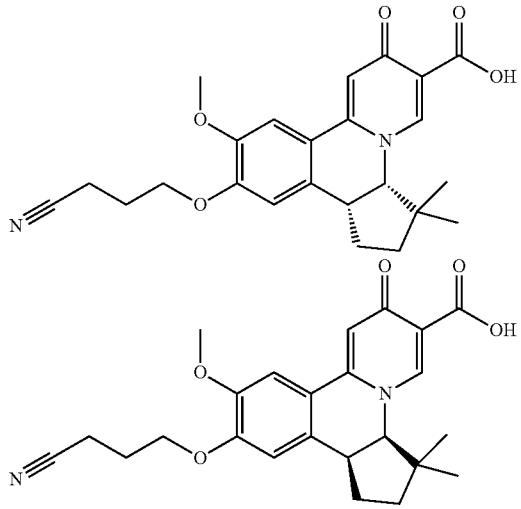

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and K$_2$CO$_3$ (83 mg, 0.6 mmol) in DMF (2 mL) was added 4-bromobutanenitrile (133 mg, 0.9 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with 2 M hydrochloric acid to pH=2-3 and extracted with CH$_2$Cl$_2$ for three times. The combined organic layers were washed with brine, dried over anhydrous Na$_2$SO$_4$ and concentrated under reduced pressure. The residue was purified by prep-HPLC to afford cis-11-(3-cyanopropoxy)-10-methoxy-3,3-dimethyl-7-oxo-1,2,3,3a,7,12b-hexahydrocyclopenta[c]pyrido[2,1-a]isoquinoline-6-carboxylic acid (24 mg) as a yellow solid. $^1$H NMR (400 MHz, DMSO-d$_6$) δ ppm 8.54 (s, 1H), 7.60 (s, 1H), 7.54 (s, 1H), 7.05 (s, 1H), 4.64 (d, 1H), 4.24-4.09 (m, 2H), 3.90 (s, 3H), 3.81-3.73 (m, 1H), 2.66 (t, 2H), 2.37-2.19 (m, 2H), 2.07 (quin, 2H), 1.58 (ddd, 1H), 1.36 (td, 1H), 1.16 (s, 3H), 0.40 (s, 3H). MS obsd. (ESI$^+$) [(M+H)$^+$]: 423.

Example 13: Cis-11-(3-hydroxypropoxy)-10-methoxy-3,3-dimethyl-7-oxo-1,2,3,3a,7,12b-hexahydrocyclopenta[c]pyrido[2,1-a]isoquinoline-6-carboxylic acid

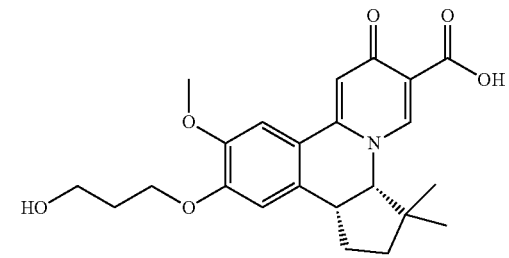

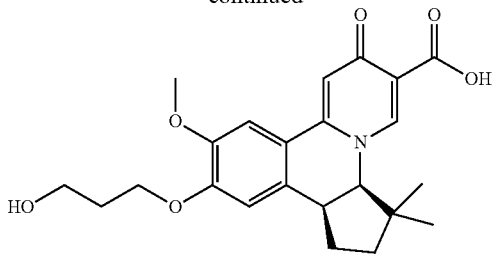

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added 3-bromopropan-1-ol (167 mg, 0.9 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with 2 M hydrochloric acid to pH=2-3 and extracted with $CH_2Cl_2$ for three times. The combined organic layers were washed with brine, dried over anhydrous $Na_2SO_4$ and concentrated under reduced pressure. The residue was purified by prep-HPLC to afford cis-11-(3-hydroxypropoxy)-10-methoxy-3,3-dimethyl-7-oxo-1,2,3,3a,7,12b-hexahydrocyclopenta[c]pyrido[2,1-a]isoquinoline-6-carboxylic acid (13 mg) as a yellow solid. $^1$H NMR (400 MHz, DMSO-$d_6$) δ ppm 8.53 (s, 1H), 7.58 (s, 1H), 7.51 (s, 1H), 7.01 (s, 1H), 4.63 (m, 2H), 4.23-4.09 (m, 2H), 3.89 (s, 3H), 3.81-3.72 (m, 1H), 3.57 (t, 2H), 2.35-2.18 (m, 2H), 1.89 (quin, 2H), 1.63-1.52 (m, 1H), 1.36 (td, 1H), 1.16 (s, 3H), 0.40 (s, 3H). MS obsd. (ESI$^+$) [(M+H)$^+$]: 414.

Example 14: Cis-11-(3-hydroxy-2,2-dimethyl-propoxy)-10-methoxy-3,3-dimethyl-7-oxo-1,2,3,3a,7,12b-hexahydrocyclopenta[c]pyrido[2,1-a]isoquinoline-6-carboxylic acid

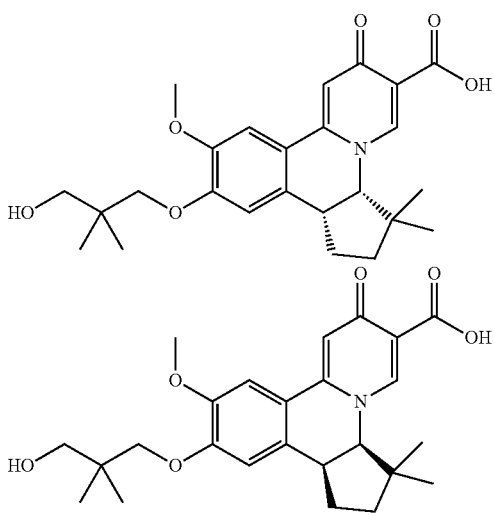

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added 3-bromo-2,2-dimethyl-propan-1-ol (150 mg, 0.9 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with 2 M hydrochloric acid to pH=2-3 and extracted with $CH_2Cl_2$ for three times. The combined organic layers were washed with brine, dried over anhydrous $Na_2SO_4$ and concentrated under reduced pressure. The residue was purified by prep-HPLC to afford cis-11-(3-hydroxy-2,2-dimethyl-propoxy)-10-methoxy-3,3-dimethyl-7-oxo-1,2,3,3a,7,12b-hexahydrocyclopenta[c]pyrido[2,1-a]isoquinoline-6-carboxylic acid (8 mg) as a yellow solid. $^1$H NMR (400 MHz, DMSO-$d_6$) δ ppm 8.54 (s, 1H), 7.58 (s, 1H), 7.52 (s, 1H), 7.00 (s, 1H), 4.63 (m, 2H), 3.90 (s, 3H), 3.87-3.81 (m, 1H), 3.80-3.74 (m, 2H), 3.30 (s, 2H), 2.35-2.19 (m, 2H), 1.64-1.52 (m, 1H), 1.36 (td, 1H), 1.16 (s, 3H), 0.95 (s, 6H), 0.40 (s, 3H). MS obsd. (ESI$^+$) [(M+H)$^+$]: 442.

Example 15: Cis-10-methoxy-3,3-dimethyl-11-(3-morpholinopropoxy)-7-oxo-1,2,3,3a,7,12b-hexahydrocyclopenta[c]pyrido[2,1-a]isoquinoline-6-carboxylic acid

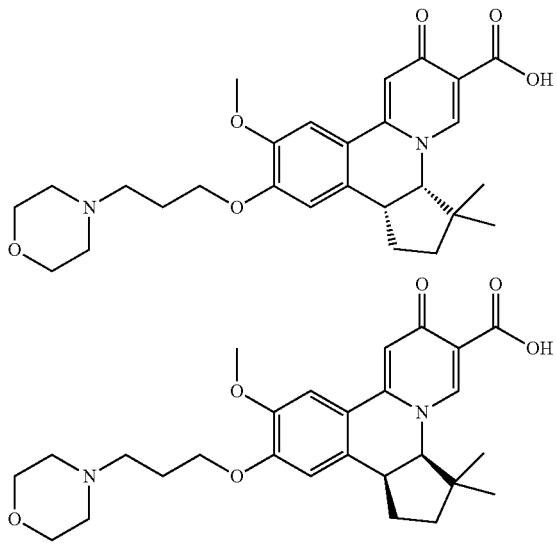

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added 4-(3-chloropropyl)morpholine (145 mg, 0.9 mmol). The mixture was heated at 120° C. with stirring for 4 hrs. To the above mixture was added LiOH aqueous solution (2.4 M, 0.5 mL, 1.2 mmol). The resulting mixture was stirred at rt for 16 hrs, and then acidified with acetic acid and extracted with $CH_2Cl_2$ for three times. The combined organic layers were washed with brine, dried over anhydrous $Na_2SO_4$ and concentrated under reduced pressure. The residue was purified by prep-HPLC to afford cis-10-methoxy-3,3-dimethyl-11-(3-morpholinopropoxy)-7-oxo-1,2,3,3a,7,12b-hexahydrocyclopenta[c]pyrido[2,1-a]isoquinoline-6-carboxylic acid (23 mg) as a yellow solid. $^1$H NMR (400 MHz, CDCl$_3$) δ ppm 8.42 (s, 1H), 7.20 (s, 1H), 7.17 (s, 1H), 6.85 (s, 1H), 4.22-4.13 (m, 3H), 3.94 (s, 3H), 3.84-3.75 (m, 5H), 2.68-2.55 (m, 6H), 2.38-2.26 (m, 2H), 2.19-2.08 (m, 2H), 1.75-1.64 (m, 1H), 1.56-1.47 (m, 1H), 1.28 (s, 3H), 0.54 (s, 3H). MS obsd. (ESI$^+$) [(M+H)$^+$]: 483.

Example 16: Cis-10-methoxy-3,3-dimethyl-7-oxo-11-(3-(pyrrolidin-1-yl)propoxy)-1,2,3,3a,7,12b-hexahydrocyclopenta[c]pyrido[2,1-a]isoquinoline-6-carboxylic acid

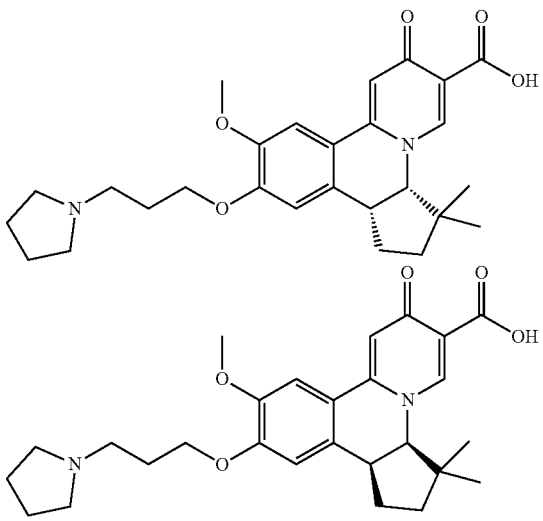

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and K₂CO₃ (124 mg, 0.9 mmol) in DMF (2 mL) was added 1-(3-chloropropyl)pyrrolidine hydrochloride (166 mg, 0.9 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, and then acidified with acetic acid and extracted with CH₂Cl₂ for three times. The combined organic layers were washed with brine, dried over anhydrous Na₂SO₄ and concentrated under reduced pressure. The residue was purified by prep-HPLC to afford cis-10-methoxy-3,3-dimethyl-7-oxo-11-(3-(pyrrolidin-1-yl)propoxy)-1,2,3,3a,7,12b-hexahydrocyclopenta[c]pyrido[2,1-a]isoquinoline-6-carboxylic acid (10 mg) as a yellow solid. ¹H NMR (400 MHz, DMSO-d₆) δ ppm 8.54 (s, 1H), 7.58 (s, 1H), 7.51 (s, 1H), 7.01 (s, 1H), 4.63 (d, 1H), 4.18-4.09 (m, 2H), 3.89 (s, 3H), 3.80-3.72 (m, 1H), 2.56-2.50 (m, 2H), 2.48-2.40 (m, 4H), 2.31-2.23 (m, 2H), 1.95-1.87 (m, 2H), 1.70-1.65 (m, 4H), 1.62-1.54 (m, 1H), 1.41-1.34 (m, 1H), 1.16 (s, 3H), 0.40 (s, 3H). MS obsd. (ESI⁺) [(M+H)⁺]: 467.

Example 17: Cis-10-methoxy-3,3-dimethyl-7-oxo-11-(3-(2-oxopyrrolidin-1-yl)propoxy)-1,2,3,3a,7,12b-hexahydrocyclopenta[c]pyrido[2,1-a]isoquinoline-6-carboxylic acid

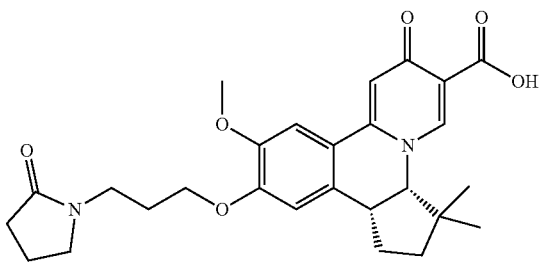

-continued

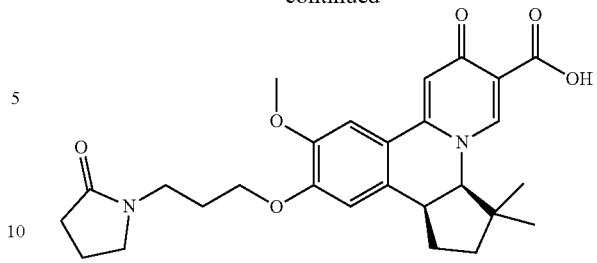

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and K₂CO₃ (83 mg, 0.6 mmol) in DMF (2 mL) was added 3-(2-oxopyrrolidin-1-yl)propyl 4-methylbenzenesulfonate (178 mg, 0.6 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with acetic acid and extracted with CH₂Cl₂ for three times. The combined organic layers were washed with brine, dried over anhydrous Na₂SO₄ and concentrated under reduced pressure. The residue was purified by prep-HPLC to afford cis-10-methoxy-3,3-dimethyl-7-oxo-11-(3-(2-oxopyrrolidin-1-yl)propoxy)-1,2,3,3a,7,12b-hexahydrocyclopenta[c]pyrido[2,1-a]isoquinoline-6-carboxylic acid (20 mg) as a yellow solid. ¹H NMR (400 MHz, DMSO-d₆) δ ppm 8.54 (s, 1H), 7.59 (s, 1H), 7.52 (s, 1H), 6.98 (s, 1H), 4.63 (d, J=8.5 Hz, 1H), 4.17-4.01 (m, 2H), 3.90 (s, 3H), 3.80-3.72 (m, 1H), 3.40-3.35 (m, 2H), 2.34-2.16 (m, 4H), 1.99-1.88 (m, 4H), 1.64-1.53 (m, 1H), 1.36 (td, J=7.8, 12.8 Hz, 1H), 1.16 (s, 3H), 0.40 (s, 3H). MS obsd. (ESI⁺) [(M+H)⁺]: 481.

Example 18: Cis-11-(4-ethoxy-4-oxobutoxy)-10-methoxy-3,3-dimethyl-7-oxo-1,2,3,3a,7,12b-hexahydrocyclopenta[c]pyrido[2,1-a]isoquinoline-6-carboxylic acid

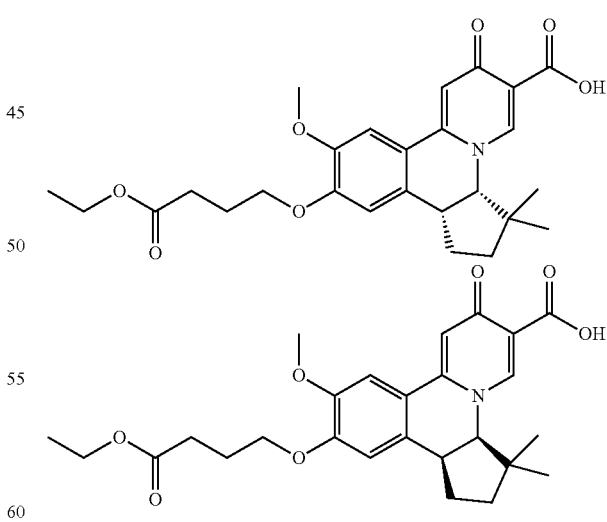

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and K₂CO₃ (83 mg, 0.6 mmol) in DMF (2 mL) was added ethyl 4-bromobutanoate (176 mg, 0.9 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with acetic acid and extracted with $CH_2Cl_2$ for three times. The combined organic layers were washed with brine, dried over anhydrous $Na_2SO_4$ and concentrated under reduced pressure. The residue was purified by prep-HPLC to afford cis-11-(4-ethoxy-4-oxobutoxy)-10-methoxy-3,3-dimethyl-7-oxo-1,2,3,3a,7,12b-hexahydrocyclopenta[c]pyrido[2,1-a]isoquinoline-6-carboxylic acid (15 mg) as a yellow solid. $^1$H NMR (400 MHz, DMSO-$d_6$) δ ppm 8.53 (s, 1H), 7.59 (s, 1H), 7.52 (s, 1H), 7.01 (s, 1H), 4.63 (d, 1H), 4.17-4.02 (m, 4H), 3.89 (s, 3H), 3.82-3.72 (m, 1H), 2.49-2.44 (m, 2H), 2.35-2.18 (m, 2H), 2.00 (quin, 2H), 1.63-1.53 (m, 1H), 1.35 (td, 1H), 1.22-1.14 (m, 6H), 0.40 (s, 3H). MS obsd. (ESI$^+$) [(M+H)$^+$]: 470.

Example 19: Cis-11-(3-carboxypropoxy)-10-methoxy-3,3-dimethyl-7-oxo-1,2,3,3a,7,12b-hexahydrocyclopenta[c]pyrido[2,1-a]isoquinoline-6-carboxylic acid

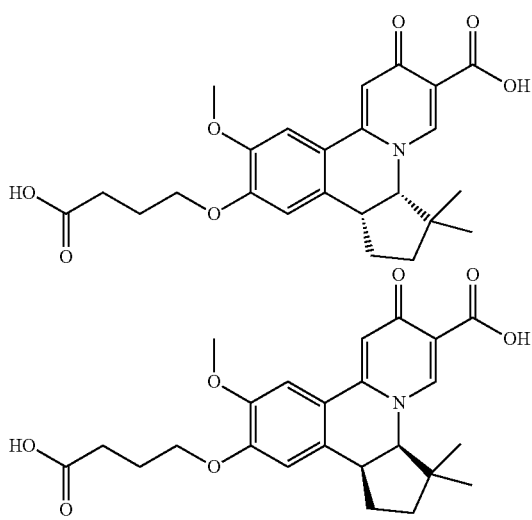

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added ethyl 4-bromobutanoate (176 mg, 0.9 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with acetic acid and extracted with $CH_2Cl_2$ for three times. The combined organic layers were washed with brine, dried over anhydrous $Na_2SO_4$ and concentrated under reduced pressure. The residue was purified by prep-HPLC to afford desired cis-11-(3-carboxypropoxy)-10-methoxy-3,3-dimethyl-7-oxo-1,2,3,3a,7,12b-hexahydrocyclopenta[c]pyrido[2,1-a]isoquinoline-6-carboxylic acid (25 mg) as a yellow solid. $^1$H NMR (400 MHz, DMSO-$d_6$) δ ppm 8.53 (s, 1H), 7.58 (s, 1H), 7.51 (s, 1H), 7.02 (s, 1H), 4.62 (d, 1H), 4.18-4.02 (m, 2H), 3.89 (s, 3H), 3.82-3.72 (m, 1H), 2.40 (t, 2H), 2.35-2.20 (m, 2H), 1.96 (quin, 2H), 1.58 (ddd, 1H), 1.35 (td, 1H), 1.16 (s, 3H), 0.39 (s, 3H). MS obsd. (ESI$^+$) [(M+H)$^+$]: 442.

Example 20: Cis-10-methoxy-3,3-dimethyl-11-(3-(methylthio)propoxy)-7-oxo-1,2,3,3a,7,12b-hexahydrocyclopenta[c]pyrido[2,1-a]isoquinoline-6-carboxylic acid

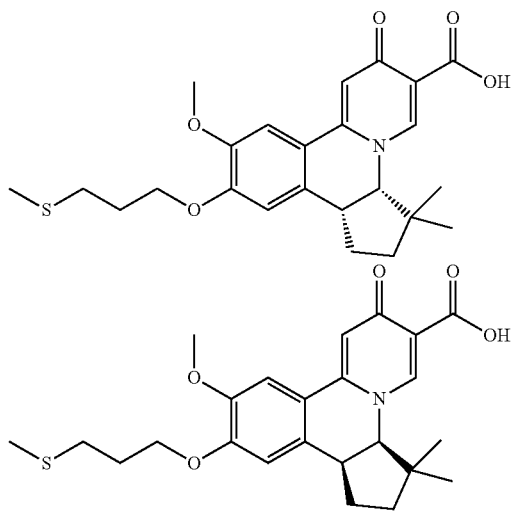

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added 3-methylsulfanylpropyl 4-methylbenzenesulfonate (156 mg, 0.6 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with acetic acid and extracted with $CH_2Cl_2$ for three times. The combined organic layers were washed with brine, dried over anhydrous $Na_2SO_4$ and concentrated under reduced pressure. The residue was purified by prep-HPLC to afford desired cis-10-methoxy-3,3-dimethyl-11-(3-(methylthio)propoxy)-7-oxo-1,2,3,3a,7,12b-hexahydrocyclopenta[c]pyrido[2,1-a]isoquinoline-6-carboxylic acid (14 mg) as a yellow solid. $^1$H NMR (400 MHz, DMSO-$d_6$) δ ppm 8.53 (s, 1H), 7.58 (s, 1H), 7.51 (s, 1H), 7.02 (s, 1H), 4.62 (d, 1H), 4.24-4.08 (m, 2H), 3.89 (s, 3H), 3.81-3.71 (m, 1H), 2.62 (m, 2H), 2.32-2.22 (m, 2H), 2.07 (s, 3H), 2.01 (quin, 2H), 1.64-1.53 (m, 1H), 1.35 (td, 1H), 1.16 (s, 3H), 0.39 (s, 3H). MS obsd. (ESI$^+$) [(M+H)$^+$]: 444.

Example 21: Cis-10-methoxy-3,3-dimethyl-11-(3-(methylsulfonyl)propoxy)-7-oxo-1,2,3,3a,7,12b-hexahydrocyclopenta[c]pyrido[2,1-a]isoquinoline-6-carboxylic acid

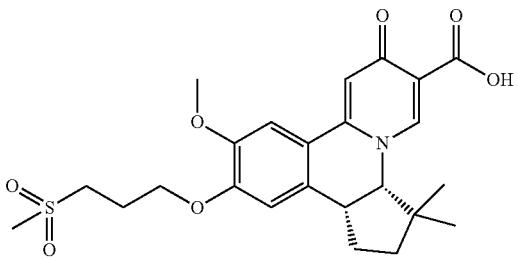

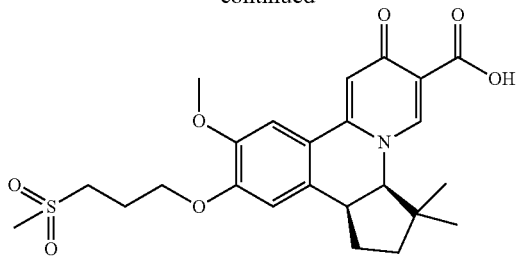

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added 3-methylsulfonylpropyl 4-methylbenzenesulfonate (175 mg, 0.6 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with acetic acid and extracted with $CH_2Cl_2$ for three times. The combined organic layers were washed with brine, dried over anhydrous $Na_2SO_4$ and concentrated under reduced pressure. The residue was purified by prep-HPLC to afford cis-10-methoxy-3,3-dimethyl-11-(3-(methylsulfonyl)propoxy)-7-oxo-1,2,3,3a,7,12b-hexahydrocyclopenta[c]pyrido[2,1-a]isoquinoline-6-carboxylic acid (13 mg) as a yellow solid. $^1$H NMR (400 MHz, DMSO-$d_6$) δ ppm 8.54 (s, 1H), 7.59 (s, 1H), 7.53 (s, 1H), 7.02 (s, 1H), 4.63 (d, 1H), 4.30-4.14 (m, 2H), 3.90 (s, 3H), 3.81-3.73 (m, 1H), 3.31-3.25 (m, 2H), 3.04 (s, 3H), 2.35-2.12 (m, 4H), 1.64-1.53 (m, 1H), 1.35 (td, 1H), 1.16 (s, 3H), 0.39 (s, 3H). MS obsd. (ESI$^+$) [(M+H)$^+$]: 476.

Example 22: Cis-11-((6-hydroxyhexyl)oxy)-10-methoxy-3,3-dimethyl-7-oxo-1,2,3,3a,7,12b-hexahydrocyclopenta[c]pyrido[2,1-a]isoquinoline-6-carboxylic acid

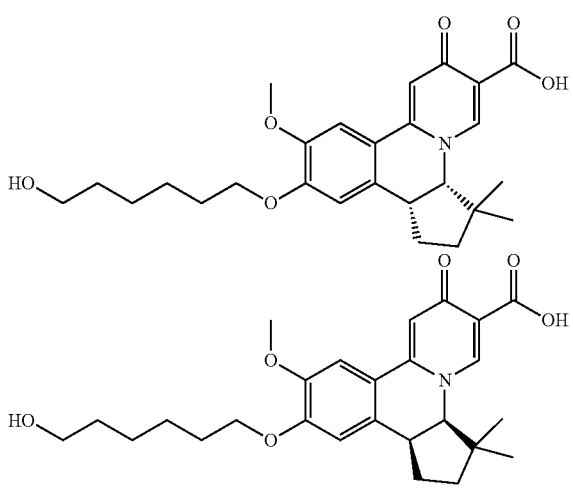

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (115 mg, 0.3 mmol) and $K_2CO_3$ (83 mg, 0.6 mmol) in DMF (2 mL) was added 3-methylsulfonylpropyl 4-methylbenzenesulfonate (163 mg, 0.9 mmol). The mixture was heated at 120° C. with stirring for 4 hrs, and then cooled to rt. To the above mixture was added LiOH aqueous solution (2.4 M, 0.5 mL, 1.2 mmol). The resulting mixture was stirred at rt for 16 hrs, then acidified with acetic acid and extracted with $CH_2Cl_2$ for three times. The combined organic layers were washed with brine, dried over anhydrous $Na_2SO_4$ and concentrated under reduced pressure. The residue was purified by prep-HPLC to afford cis-11-((6-hydroxyhexyl)oxy)-10-methoxy-3,3-dimethyl-7-oxo-1,2,3,3a,7,12b-hexahydrocyclopenta[c]pyrido[2,1-a]isoquinoline-6-carboxylic acid (21 mg) as a yellow solid. $^1$H NMR (400 MHz, DMSO-$d_6$) δ ppm 8.53 (s, 1H), 7.58 (s, 1H), 7.51 (s, 1H), 7.00 (s, 1H), 4.63 (d, 1H), 4.37 (br. s., 1H), 4.15-3.99 (m, 2H), 3.89 (s, 3H), 3.76 (t, 1H), 3.40 (br. s., 2H), 2.36-2.18 (m, 2H), 1.74 (quin, 2H), 1.58 (ddd, 1H), 1.50-1.30 (m, 7H), 1.16 (s, 3H), 0.40 (s, 3H). MS obsd. (ESI$^+$) [(M+H)$^+$]: 456.

Example 23: Cis-11-((6-((tert-butoxycarbonyl)amino)hexyl)oxy)-10-methoxy-3,3-dimethyl-7-oxo-1,2,3,3a,7,12b-hexahydrocyclopenta[c]pyrido[2,1-a]isoquinoline-6-carboxylic acid

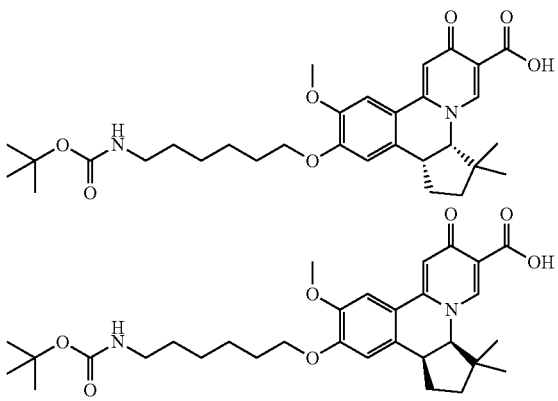

Step 1: Preparation of 6-(tert-butoxycarbonylamino)hexyl 4-methylbenzenesulfonate

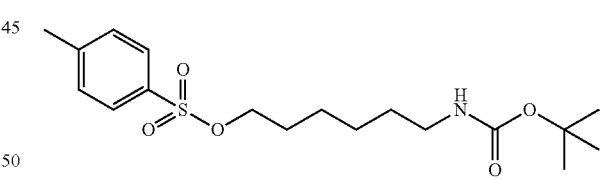

A mixture of tert-butyl N-(6-hydroxyhexyl)carbamate (5.38 g, 24.8 mmol), triethylamine (5.01 g, 49.6 mmol) and 4-dimethylaminopyridine (151 mg, 1.24 mmol) in $CH_2Cl_2$ (60 mL) was stirred at 0° C. for 30 min, then p-tolylsulfonylchloride (4.71 g, 24.8 mmol) was added in portions at 0° C. The resulting mixture was allowed to warm to rt and stirred at rt overnight. The mixture was diluted with water, and extracted with $CH_2Cl_2$ for three times. The combined organic layers were washed with 1 M hydrochloric acid for three times, then washed with saturated $NaHCO_3$ aqueous solution and brine, dried over anhydrous $Na_2SO_4$ and concentrated under reduced pressure to give 6-(tert-butoxycarbonylamino)hexyl 4-methylbenzenesulfonate (8.30 g) as a yellow oil which was directly used in the next step without further purification.

Step 2: Cis-ethyl 11-((6-((tert-butoxycarbonyl) amino)hexyl)oxy)-10-methoxy-3,3-dimethyl-7-oxo-1,2,3,3a,7,12b-hexahydrocyclopenta[c]pyrido[2,1-a] isoquinoline-6-carboxylate

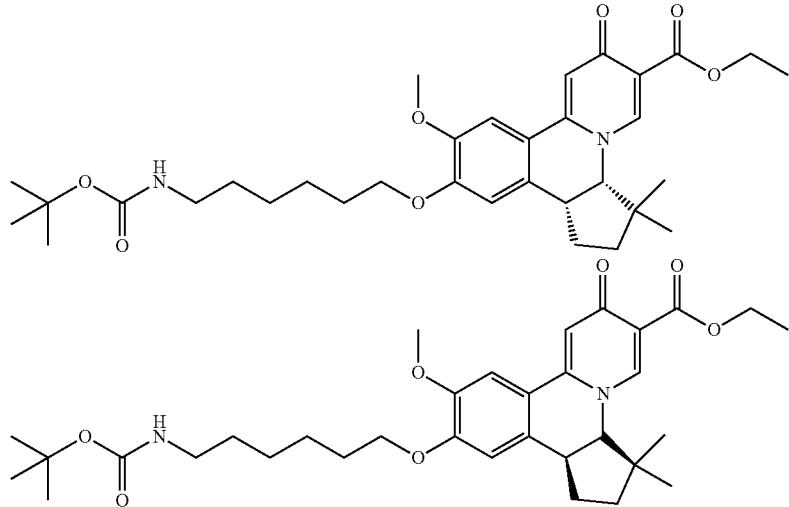

To a mixture of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (460 mg, 1.2 mmol) and K$_2$CO$_3$ (331 mg, 2.4 mmol) in DMF (8 mL) was added 6-(tert-butoxycarbonylamino)hexyl 4-methylbenzenesulfonate (1.33 g, 3.6 mmol). The mixture was heated at 120° C. with stirring for 3 hrs. After being cooled to rt, the mixture was partitioned between CH$_2$Cl$_2$ and water. The separated aqueous layer was extracted with CH$_2$Cl$_2$ for three times. The combined organic layers were washed with brine, dried over anhydrous Na$_2$SO$_4$ and concentrated under reduced pressure to give crude cis-ethyl 11-((6-((tert-butoxycarbonyl)amino)hexyl)oxy)-10-methoxy-3,3-dimethyl-7-oxo-1,2,3,3a,7,12b-hexahydrocyclopenta[c]pyrido[2,1-a]isoquinoline-6-carboxylate (1.48 g) as a brown oil which was directly used in the next step without further purification.

Step 3: Preparation of cis-11-((6-((tert-butoxycarbonyl)amino)hexyl)oxy)-10-methoxy-3,3-dimethyl-7-oxo-1,2,3,3a,7,12b-hexahydrocyclopenta[c]pyrido[2,1-a]isoquinoline-6-carboxylic acid To a solution of crude cis-ethyl 11-((6-((tert-butoxycarbonyl)amino)hexyl)oxy)-10-methoxy-3,3-dimethyl-7-oxo-1,2,3,3a,7,12b-hexahydrocyclopenta[c]pyrido[2,1-a]isoquinoline-6-carboxylate (370 mg, 0.3 mmol) in methanol (3 mL) and H$_2$O (1 mL) was added LiOH.H$_2$O (50 mg, 1.2 mmol). The mixture was stirred at rt overnight, then diluted with water and acidified with 2 M hydrochloric acid to pH=2-3. The resulting mixture was extracted with CH$_2$Cl$_2$ for three times. The combined organic layers were washed with brine, dried over anhydrous Na$_2$SO$_4$ and concentrated under reduced pressure. The residue was purified by prep-HPLC to afford cis-11-((6-((tert-butoxycarbonyl)amino) hexyl)oxy)-10-methoxy-3,3-dimethyl-7-oxo-1,2,3,3a,7,12b-hexahydrocyclopenta[c]pyrido[2,1-a]isoquinoline-6-carboxylic acid (28 mg) as a yellow solid. $^1$H NMR (400 MHz, DMSO-d$_6$) δ ppm 8.53 (s, 1H), 7.58 (s, 1H), 7.51 (s, 1H), 6.99 (s, 1H), 6.79 (m, 1H), 4.63 (d, 1H), 4.16-4.00 (m, 2H), 3.89 (s, 3H), 3.76 (t, 1H), 2.96-2.85 (m, 2H), 2.35-2.18 (m, 2H), 1.79-1.65 (m, 2H), 1.64-1.51 (m, 1H), 1.45-1.22 (m, 17H), 1.16 (s, 3H), 0.40 (s, 3H). MS obsd. (ESI$^+$) [(M+H)$^+$]: 555.

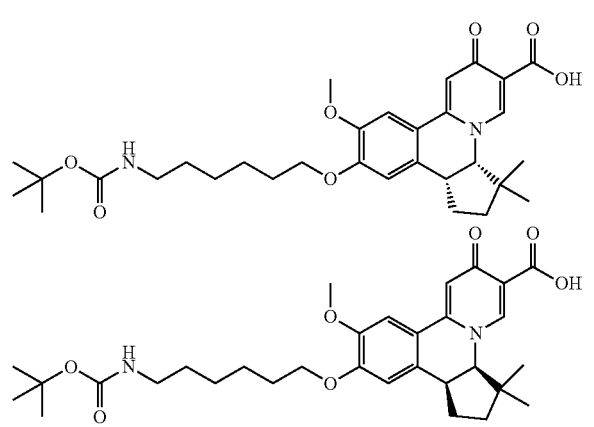

Example 24: Cis-11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylic acid

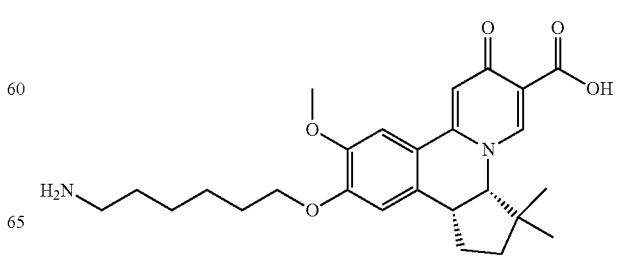

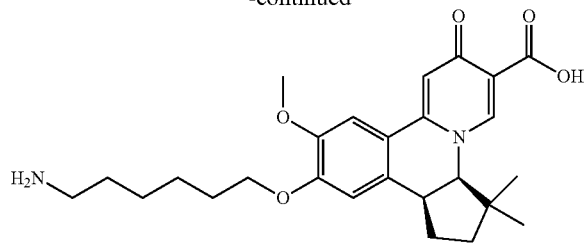

Step 1: Preparation of cis-ethyl 11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylate

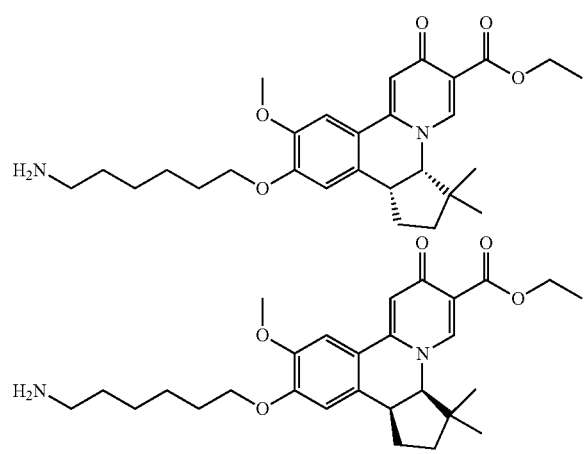

To a solution of crude cis-ethyl 11-((6-((tert-butoxycarbonyl)amino)hexyl)oxy)-10-methoxy-3,3-dimethyl-7-oxo-1,2,3,3a,7,12b-hexahydrocyclopenta[c]pyrido[2,1-a]isoquinoline-6-carboxylate (1.11 g, 0.9 mmol) in $CH_2Cl_2$ (10 mL) was added trifluoroacetic acid (2 mL). The resulting mixture was stirred at rt overnight, then concentrated under reduced pressure to give crude cis-ethyl 11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylate (2.10 g) as a brown oil which was directly used in the next step without further purification.

Step 2: Preparation of cis-11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylic acid

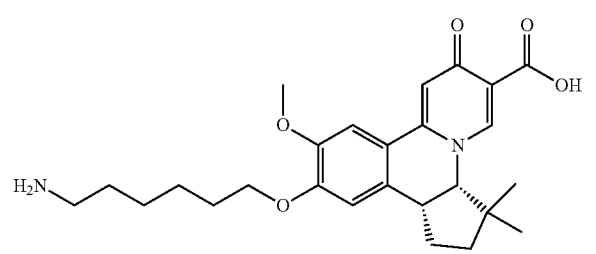

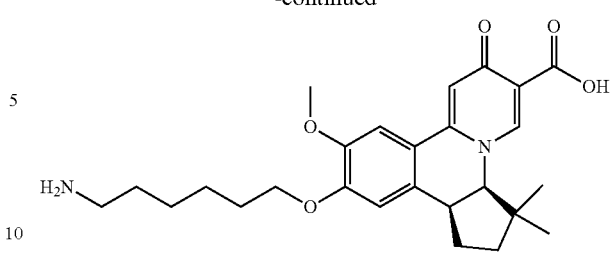

To a solution of crude cis-ethyl 11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylate (700 mg, 0.3 mmol) in methanol (3 mL) and $H_2O$ (1 mL) was added $LiOH \cdot H_2O$ (252 mg, 6 mmol). The mixture was stirred at rt for 2 hrs, then diluted with water and acidified with 2 M hydrochloric acid to pH=2-3. The resulting mixture was extracted with $CH_2Cl_2$ for three times. The combined organic layers were washed with brine, dried over anhydrous $Na_2SO_4$ and concentrated under reduced pressure. The residue was purified by prep-HPLC to afford cis-11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylic acid (6 mg) as a colorless oil. MS obsd. (ESI$^+$) [(M+H)$^+$]: 455.

Example 25: Cis-11-((6-acetamidohexyl)oxy)-10-methoxy-3,3-dimethyl-7-oxo-1,2,3,3a,7,12b-hexahydrocyclopenta[c]pyrido[2,1-a]isoquinoline-6-carboxylic acid

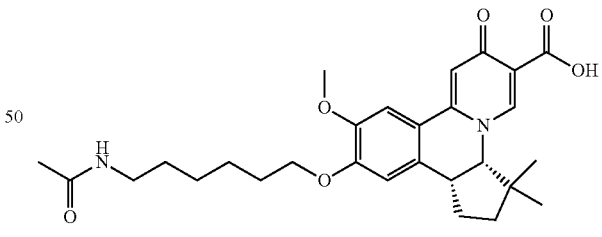

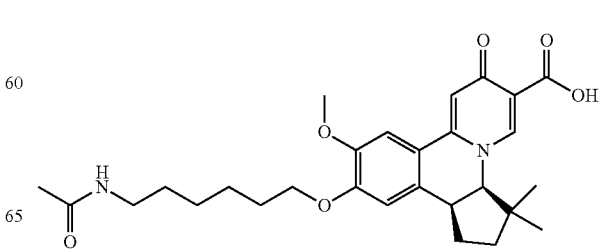

Step 1: Preparation of cis-ethyl 11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylate hydrochloride

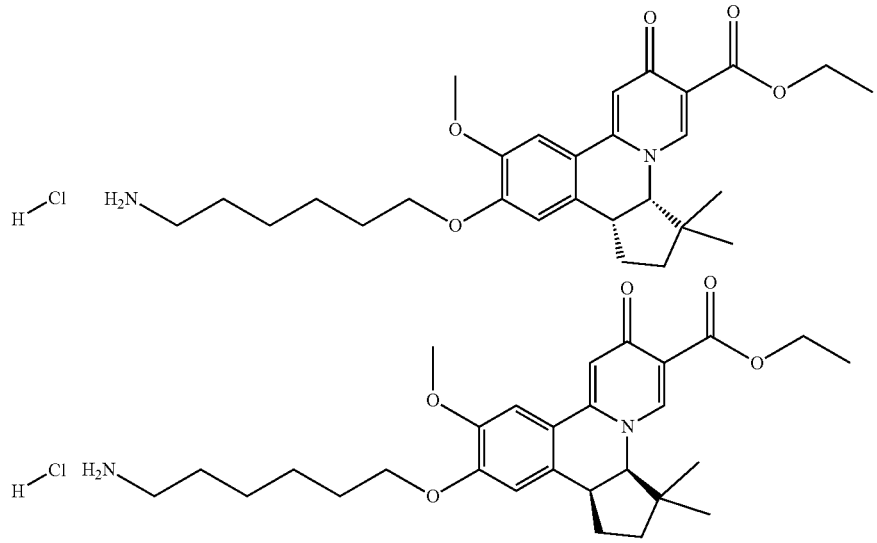

A mixture of cis-ethyl 11-((6-((tert-butoxycarbonyl)amino)hexyl)oxy)-10-methoxy-3,3-dimethyl-7-oxo-1,2,3,3a,7,12b-hexahydrocyclopenta[c]pyrido[2,1-a]isoquinoline-6-carboxylate (510 mg, 0.6 mmol) and 1 M HCl in EtOAc solution (15 mL) stirred at rt overnight. The resulting mixture was concentrated under reduced pressure to give crude cis-ethyl 11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylate hydrochloride (454 mg) as a brown oil which was directly used in the next step without further purification.

Step 2: Preparation of cis-11-((6-acetamidohexyl)oxy)-10-methoxy-3,3-dimethyl-7-oxo-1,2,3,3a,7,12b-hexahydrocyclopenta[c]pyrido[2,1-a]isoquinoline-6-carboxylic acid

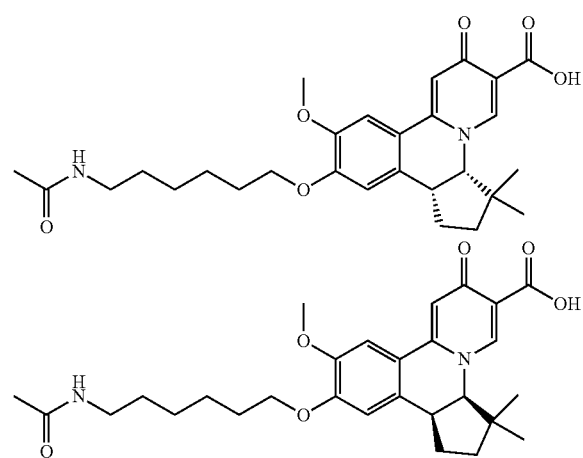

To a solution of cis-ethyl 11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylate hydrochloride (227 mg, 0.3 mmol) and N,N-diisopropylethylamine (194 mg, 1.5 mmol) in $CH_2Cl_2$ (3 mL) was added acetyl chloride (70 mg, 0.9 mmol). The resulting mixture was stirred at rt for 1 h, and then concentrated under reduced pressure. The residue was dissolved in methanol (3 mL) and $H_2O$ (1 mL), then to the solution was added $LiOH \cdot H_2O$ (101 mg, 2.4 mmol). The resulting mixture was stirred at rt for 16 hrs, then diluted with water and acidified with 2 M hydrochloric acid to pH=2-3. The resulting mixture was extracted with $CH_2Cl_2$ for three times. The combined organic layers were washed with brine, dried over anhydrous $Na_2SO_4$ and concentrated under reduced pressure. The residue was purified by prep-HPLC to afford cis-11-((6-acetamidohexyl)oxy)-10-methoxy-3,3-dimethyl-7-oxo-1,2,3,3a,7,12b-hexahydrocyclopenta[c]pyrido[2,1-a]isoquinoline-6-carboxylic acid (27 mg) as a yellow solid. $^1$H NMR (400 MHz, DMSO-$d_6$) δ ppm 8.54 (s, 1H), 7.80 (t, 1H), 7.58 (s, 1H), 7.51 (s, 1H), 7.00 (s, 1H), 4.63 (d, 1H), 4.15-4.00 (m, 2H), 3.89 (s, 3H), 3.76 (t, 1H), 3.02 (q, 2H), 2.35-2.19 (m, 2H), 1.78 (s, 3H), 1.77-1.69 (m, 2H), 1.58 (ddd, 1H), 1.47-1.28 (m, 7H), 1.16 (s, 3H), 0.40 (s, 3H). MS obsd. (ESI$^+$) [(M+H)$^+$]: 497.

Example 26: Cis-10-methoxy-3,3-dimethyl-11-((6-(methylsulfonamido)hexyl)oxy)-7-oxo-1,2,3,3a,7,12b-hexahydrocyclopenta[c]pyrido[2,1-a]isoquinoline-6-carboxylic acid

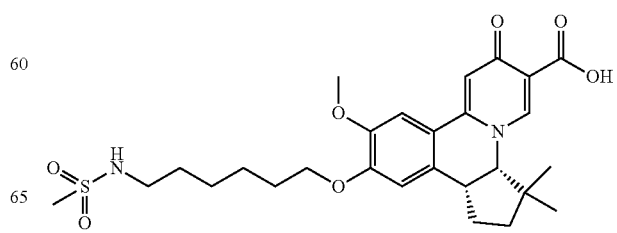

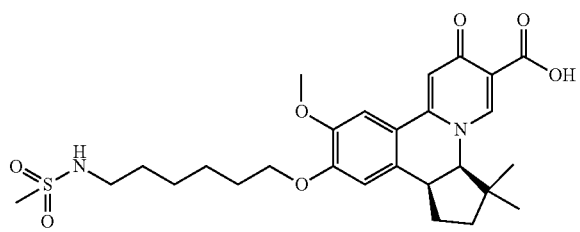

To a solution of cis-ethyl 11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylate hydrochloride (227 mg, 0.3 mmol) and N,N-diisopropylethylamine (194 mg, 1.5 mmol) in $CH_2Cl_2$ (3 mL) was added methanesulfonic anhydride (263 mg, 1.5 mmol). The mixture was stirred at rt for 1 h, and then concentrated under reduced pressure. The residue was dissolved in methanol (3 mL) and $H_2O$ (1 mL), then to the solution was added $LiOH.H_2O$ (101 mg, 2.4 mmol). The resulting mixture was stirred at rt for 16 hrs, then diluted with water and acidified with 2 M hydrochloric acid to pH=2-3. The resulting mixture was extracted with $CH_2Cl_2$ for three times. The combined organic layers were washed with brine, dried over anhydrous $Na_2SO_4$ and concentrated under reduced pressure. The residue was purified by prep-HPLC to afford cis-10-methoxy-3,3-dimethyl-11-((6-(methylsulfonamido)hexyl)oxy)-7-oxo-1,2,3,3a,7,12b-hexahydrocyclopenta[c]pyrido[2,1-a]isoquinoline-6-carboxylic acid (15 mg) as a yellow solid.

$^1$H NMR (400 MHz, DMSO-$d_6$) δ ppm 8.53 (s, 1H), 7.57 (s, 1H), 7.51 (s, 1H), 7.00 (s, 1H), 6.95 (t, 1H), 4.63 (d, 1H), 4.15-4.01 (m, 2H), 3.89 (s, 3H), 3.76 (t, 1H), 2.93 (q, 2H), 2.88 (s, 3H), 2.37-2.19 (m, 2H), 1.75 (quin, 2H), 1.58 (ddd, 1H), 1.52-1.33 (m, 7H), 1.16 (s, 3H), 0.40 (s, 3H). MS obsd. (ESI$^+$) [(M+H)$^+$]: 533.

Example 27 and 28: Trans-13-chloro-12-(3-methoxypropoxy)-2-oxo-2,5a,6,7,8,9,10,10a-octahydrocyclohepta[c]pyrido[2,1-a]isoquinoline-3-carboxylic acid and cis-13-chloro-12-(3-methoxypropoxy)-2-oxo-2,5a,6,7,8,9,10,10a-octahydrocyclohepta[c]pyrido[2,1-a]isoquinoline-3-carboxylic acid

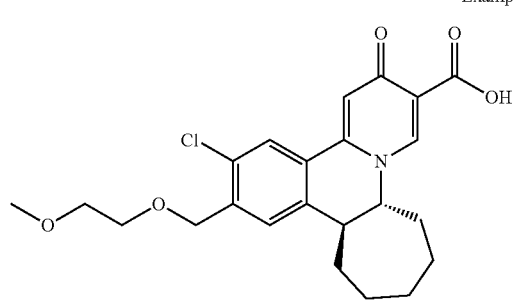

Example 27

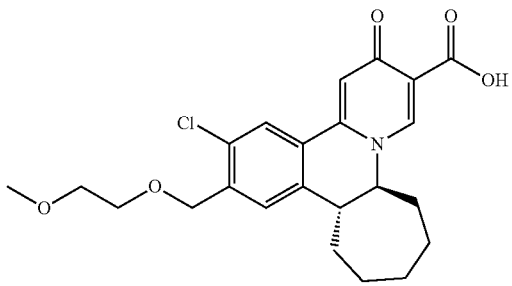

Example 28

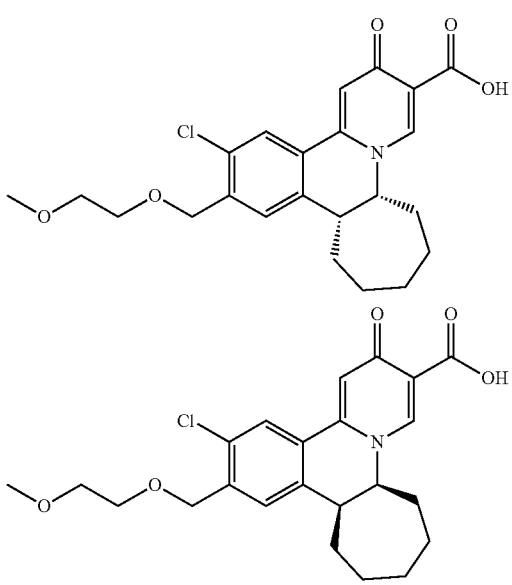

Step 1: Preparation of 2-[4-chloro-3-(3-methoxypropoxy)phenyl]cycloheptanone

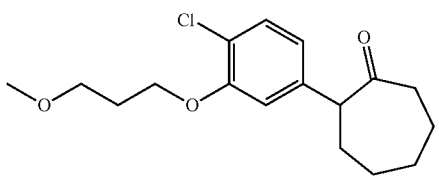 [SMILES: COCCCOc1cc(C2CCCCCC2=O)ccc1Cl]

To a mixture of 4-bromo-1-chloro-2-(3-methoxypropoxy)benzene (834 mg, 3 mmol), tris(dibenzylideneacetone)dipalladium(0) (28 mg, 0.03 mmol), 2-dicyclohexylphosphino-2'-methylbiphenyl (22 mg, 0.06 mmol) and t-BuONa (576 mg, 6 mmol) in THF (10 mL) was added cycloheptanone (672 mg, 6 mmol). The mixture was heated at 60° C. for 30 min under microwave irradiation and argon atmosphere. Then the mixture was partitioned between 1 M hydrochloric acid and EtOAc. The aqueous layer was extracted with EtOAc for three times. The combined organic layers were washed with brine, dried over anhydrous $Na_2SO_4$ and concentrated under reduced pressure to give crude 2-[4-chloro-3-(3-methoxypropoxy)phenyl]cycloheptanone (1.23 g) as a yellow oil which was directly used in the next step without further purification.

Step 2: Preparation of 2-[4-chloro-3-(3-methoxy-propoxy)phenyl]cycloheptanamine

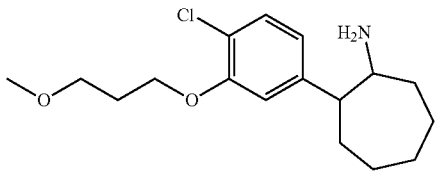 [SMILES: COCCCOc1cc(C2CCCCCC2N)ccc1Cl]

To a mixture of crude 2-[4-chloro-3-(3-methoxypropoxy)phenyl]cycloheptanone (1.23 g, 3 mmol) and ammonium acetate (6.93 g, 90 mmol) in methanol (10 mL) was added NaBH₃CN (756 mg, 12 mmol). The mixture was stirred at rt overnight, then diluted with water and basified with 2 M NaOH aqueous solution to pH=10-12. The resulting mixture was stirred at rt for 30 min, and then extracted with $CH_2Cl_2$ for three times. The combined organic layers were washed with brine, dried over anhydrous $Na_2SO_4$ and concentrated under reduced pressure to give crude 2-[4-chloro-3-(3-methoxypropoxy)phenyl]cycloheptanamine (810 mg) as a yellow oil which was directly used in the next step without further purification.

Step 3: Preparation of N-[2-[4-chloro-3-(3-methoxypropoxy)phenyl]cycloheptyl] formamide

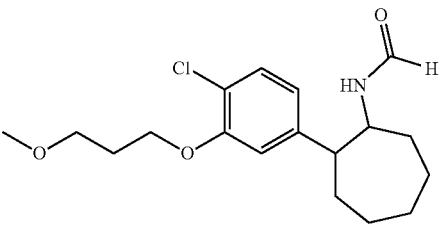 [SMILES: COCCCOc1cc(C2CCCCCC2NC=O)ccc1Cl]

A solution of crude 2-[4-chloro-3-(3-methoxypropoxy)phenyl]cycloheptanamine (810 mg, 2.6 mmol) and formic acid (0.15 mL) in ethyl formate (15 mL) was heated at 90° C. for 2 hrs. After being cooled to rt, the mixture was concentrated under reduced pressure to give crude N-[2-[4-chloro-3-(3-methoxypropoxy)phenyl]cycloheptyl]formamide (790 mg) as a yellow oil which was directly used in the next step without further purification.

Step 4: Preparation of 3-chloro-2-(3-methoxy-propoxy)-7,8,9,10,11,11a-hexahydro-6aH-cyclohepta[c]isoquinoline

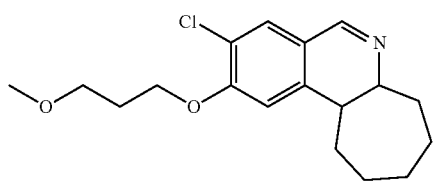 [SMILES: COCCCOc1cc2c(cc1Cl)C=NC1CCCCCC21]

To a solution of crude N-[2-[4-chloro-3-(3-methoxypropoxy)phenyl]cycloheptyl] formamide (790 mg, 2.3 mmol) in $CH_3CN$ (10 mL) was added $POCl_3$ (352 mg, 2.3 mmol). The mixture was heated at 80° C. with stirring for 3 hrs. After being cooled to rt, the mixture was concentrated under reduced pressure. The residue was dissolved in $CH_2Cl_2$. The resulting solution was basified with ammonia water to pH=10 at 0° C., then allowed to warm to rt and stirred at rt for 1 hr. Then the separated aqueous layer was extracted with $CH_2Cl_2$ for three times. The combined organic layers were washed with brine, dried over anhydrous $Na_2SO_4$ and concentrated under reduced pressure to give crude 3-chloro-2-(3-methoxypropoxy)-7,8,9,10,11,11a-hexahydro-6aH-cyclohepta[c]isoquinoline (720 mg) as a yellow oil which was directly used in the next step without further purification.

Step 5: Preparation of ethyl 13-chloro-12-(3-methoxypropoxy)-2-oxo-1,2,5a,6,7,8,9,10,10a,14b-decahydrocyclohepta[c]pyrido[2,1-a]isoquinoline-3-carboxylate

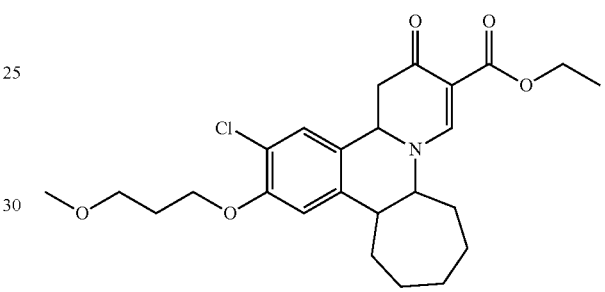

A mixture of crude 3-chloro-2-(3-methoxypropoxy)-7,8,9,10,11,11a-hexahydro-6aH-cyclohepta[c]isoquinoline (720 mg, 2.24 mmol) and ethyl 2-(ethoxymethylene)-3-oxo-butanoate (1.25 g, 6.72 mmol) in ethanol (10 mL) was heated at 100° C. with stirring overnight. The mixture was concentrated under reduced pressure to give crude ethyl 13-chloro-12-(3-methoxypropoxy)-2-oxo-1,2,5a,6,7,8,9,10,10a,14b-decahydrocyclohepta[c]pyrido[2,1-a]isoquinoline-3-carboxylate (2.04 g) as a brown oil which was directly used in the next step without further purification.

Step 6: Preparation of ethyl 13-chloro-12-(3-methoxypropoxy)-2-oxo-2,5a,6,7,8,9,10,10a-octahydrocyclohepta[c]pyrido[2,1-a]isoquinoline-3-carboxylate

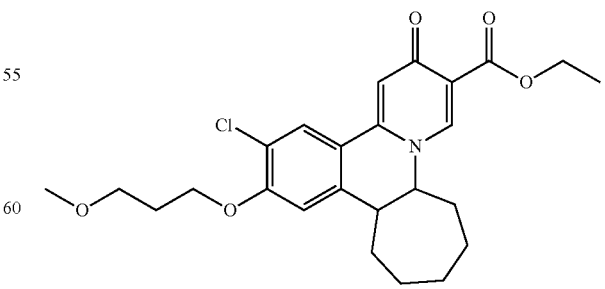

A mixture of crude ethyl 13-chloro-12-(3-methoxypropoxy)-2-oxo-1,2,5a,6,7,8,9,10,10a,14b-decahydrocyclohepta[c]pyrido[2,1-a]isoquinoline-3-carboxylate (2.04 g, 2.24 mmol) and p-chloranil (551 mg, 2.24 mmol) in DME (10 mL) was heated at 70° C. with stirring for 3 hrs. After being cooled to rt, the mixture was filtered. The filter cake was dried under reduced pressure to give crude ethyl 13-chloro-12-(3-methoxypropoxy)-2-oxo-2,5a,6,7,8,9,10,10a-octahydrocyclohepta[c]pyrido[2,1-a]isoquinoline-3-carboxylate (275 mg) which was directly used in the next step without further purification.

Step 7: Preparation of trans-13-chloro-12-(3-methoxypropoxy)-2-oxo-2,5a,6,7,8,9,10,10a-octahydrocyclohepta[c]pyrido[2,1-a]isoquinoline-3-carboxylic acid and cis-13-chloro-12-(3-methoxypropoxy)-2-oxo-2,5a,6,7,8,9,10,10a-octahydrocyclohepta[c]pyrido[2,1-a]isoquinoline-3-carboxylic acid

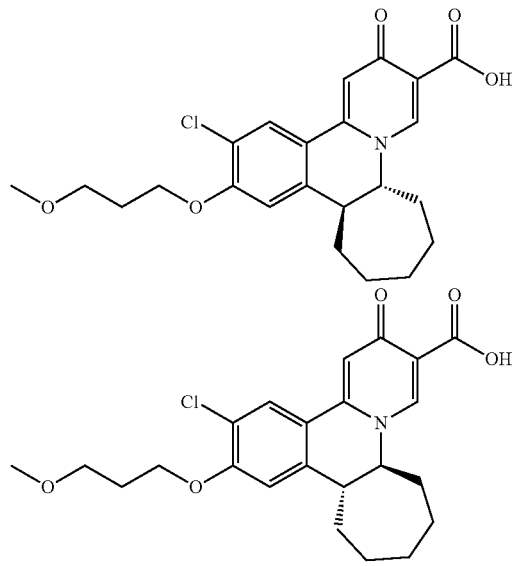

Example 27

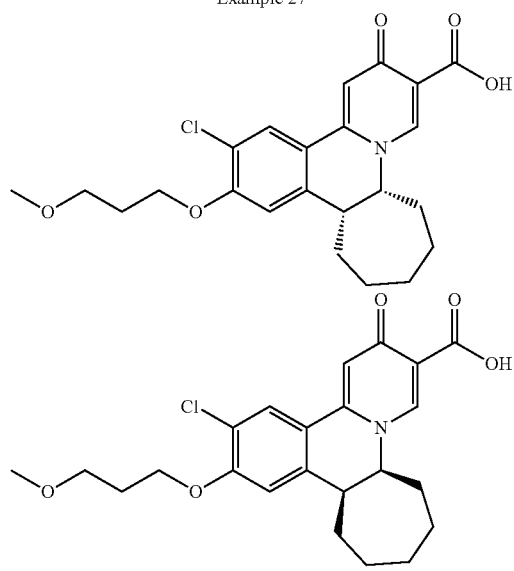

Example 28

To a solution of crude ethyl 13-chloro-12-(3-methoxypropoxy)-2-oxo-2,5a,6,7,8,9,10,10a-octahydrocyclohepta[c]pyrido[2,1-a]isoquinoline-3-carboxylate (275 mg, 0.6 mmol) in methanol (4 mL) and H$_2$O (1 mL) was added LiOH.H$_2$O (202 mg, 4.8 mmol). The mixture was stirred at rt for 64 hrs, then diluted with water and acidified with 1 M hydrochloric acid to pH=2-3. The resulting mixture was extracted with CH$_2$Cl$_2$ for three times. The combined organic layers were washed with brine, dried over anhydrous Na$_2$SO$_4$ and concentrated under reduced pressure. The residue was purified by prep-HPLC and precipitation from diethyl ether/methanol to afford trans-13-chloro-12-(3-methoxypropoxy)-2-oxo-2,5a,6,7,8,9,10,10a-octahydrocyclohepta[c]pyrido[2,1-a]isoquinoline-3-carboxylic acid (50 mg) as a yellow solid and cis-13-chloro-12-(3-methoxypropoxy)-2-oxo-2,5a,6,7,8,9,10,10a-octahydrocyclohepta[c]pyrido[2,1-a]isoquinoline-3-carboxylic acid (15 mg) as a yellow solid.

Example 27

$^1$H NMR (400 MHz, DMSO-d$_6$) δ ppm 8.85 (s, 1H), 8.22 (s, 1H), 7.37 (s, 1H), 7.14 (s, 1H), 4.89-4.78 (m, 1H), 4.31-4.17 (m, 2H), 3.65 (m, 1H), 3.52 (t, 2H), 3.27 (s, 3H), 2.34-2.21 (m, 1H), 2.14-1.96 (m, 4H), 1.76-1.50 (m, 7H). MS obsd. (ESI$^+$) [(M+H)$^+$]: 432.

Example 28

$^1$H NMR (400 MHz, DMSO-d$_6$) δ ppm 8.62 (s, 1H), 8.18 (s, 1H), 7.34 (s, 1H), 7.19 (s, 1H), 4.27 (m, 2H), 4.00-3.90 (m, 1H), 3.52 (t, 2H), 3.27 (s, 3H), 3.04 (m, 1H), 2.46-2.30 (m, 3H), 2.08-1.97 (m, 2H), 1.94-1.50 (m, 7H). MS obsd. (ESI$^+$) [(M+H)$^+$]: 432.

Example 29 and 30: Trans-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid and cis-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid

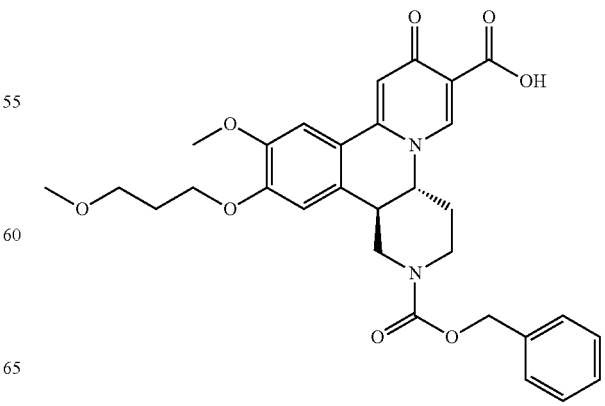

-continued

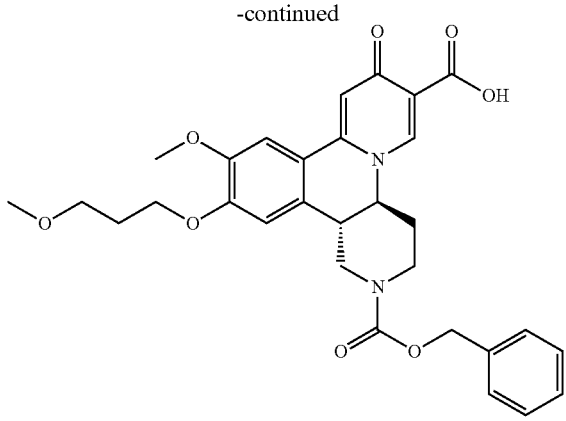

Example 29

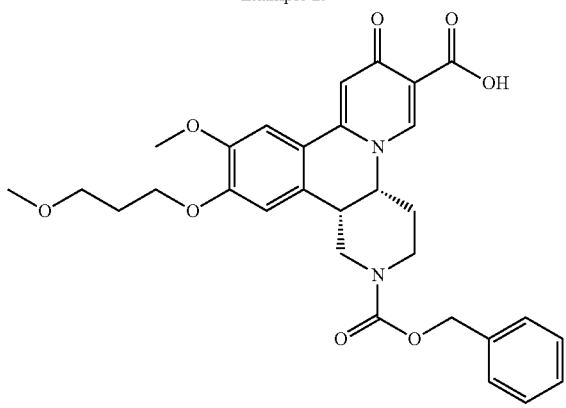

Example 30

Step 1: Preparation of benzyl 3-[4-methoxy-3-(3-methoxypropoxy)phenyl]-4-oxo-piperidine-1-carboxylate

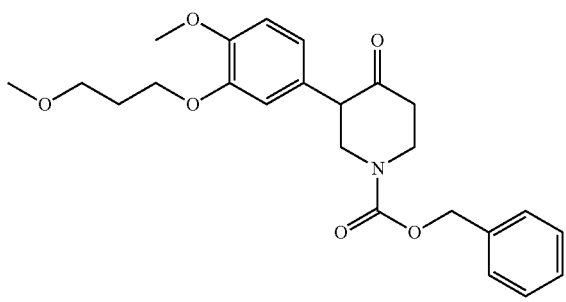 [SMILES: COCCCOc1cc(C2CN(C(=O)OCc3ccccc3)CCC2=O)ccc1OC]

To a mixture of 4-bromo-1-methoxy-2-(3-methoxypropoxy)benzene (1.10 g, 4 mmol), tris(dibenzylideneacetone)dipalladium(0) (37 mg, 0.04 mmol), 2-dicyclohexylphosphino-2'-methylbiphenyl (25 mg, 0.08 mmol) and t-BuONa (768 mg, 8 mmol) in THF (10 mL) was added benzyl 4-oxopiperidine-1-carboxylate (1.86 g, 8 mmol). The mixture was heated at 60° C. for 15 min under microwave irradiation. After being cooled to rt, the mixture was partitioned between water and EtOAc, then the aqueous layer was extracted with EtOAc for two times. The combined organic layers were washed with brine, dried over anhydrous $Na_2SO_4$ and concentrated under reduced pressure to give crude benzyl 3-[4-methoxy-3-(3-methoxypropoxy)phenyl]-4-oxo-piperidine-1-carboxylate (2.72 g) as a yellow oil which was directly used in the next step without further purification.

Step 2: Preparation of benzyl 4-amino-3-[4-methoxy-3-(3-methoxypropoxy)phenyl]piperidine-1-carboxylate

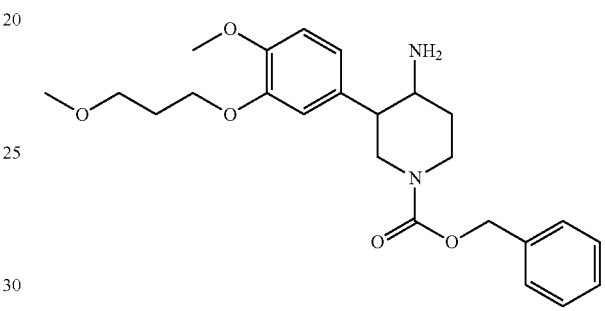

To a mixture of crude benzyl 3-[4-methoxy-3-(3-methoxypropoxy)phenyl]-4-oxo-piperidine-1-carboxylate (2.72 g, 4 mmol) and ammonium acetate (4.62 g, 60 mmol) in methanol (30 mL) was added $NaBH_3CN$ (504 mg, 8 mmol). The mixture was stirred at rt overnight, then diluted with water and basified with 2 M NaOH aqueous solution to pH=10-12. The resulting mixture was stirred at rt for 30 min, and extracted with $CH_2Cl_2$ for three times. The combined organic layers were washed with brine, dried over anhydrous $Na_2SO_4$ and concentrated under reduced pressure to give crude benzyl 4-amino-3-[4-methoxy-3-(3-methoxypropoxy)phenyl]piperidine-1-carboxylate (1.95 g) as a yellow oil which was directly used in the next step without further purification.

Step 3: Preparation of benzyl 4-formamido-3-[4-methoxy-3-(3-methoxypropoxy)phenyl]piperidine-1-carboxylate

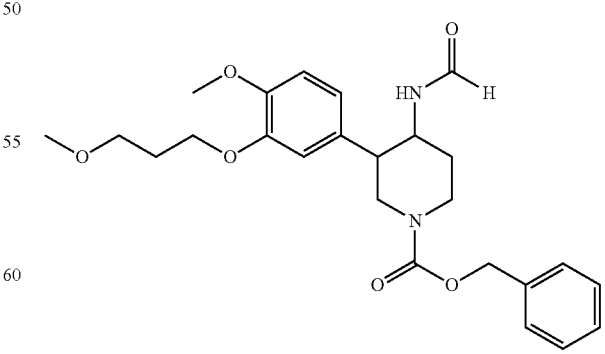

A solution of crude benzyl 4-amino-3-[4-methoxy-3-(3-methoxypropoxy)phenyl]piperidine-1-carboxylate (1.92 g, 4 mmol) and formic acid (0.02 mL) in ethyl formate (20 mL) was heated at 90° C. with stirring overnight. After being

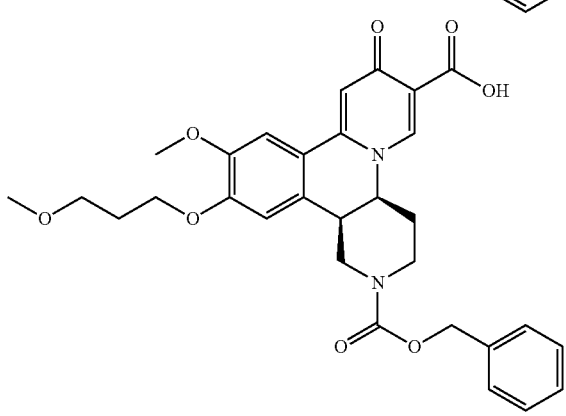

cooled to rt, the mixture was concentrated under reduced pressure to give crude benzyl 4-formamido-3-[4-methoxy-3-(3-methoxypropoxy)phenyl]piperidine-1-carboxylate (1.97 g) as a yellow oil which was directly used in the next step without further purification.

Step 4: Preparation of benzyl 8-methoxy-9-(3-methoxypropoxy)-3,4,4a,10b-tetrahydro-1H-benzo[c][1,6]naphthyridine-2-carboxylate

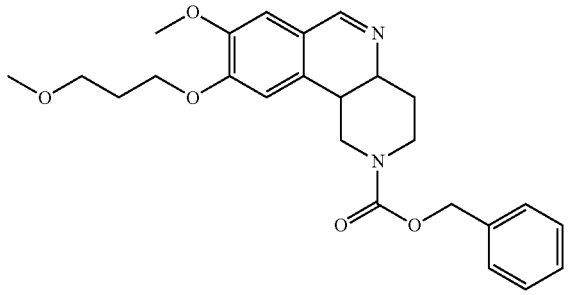 [SMILES: COCCCOc1cc2c(cc1OC)C=NC1CCN(C(=O)OCc3ccccc3)CC21]

To a solution of crude benzyl 4-formamido-3-[4-methoxy-3-(3-methoxypropoxy)phenyl]piperidine-1-carboxylate (1.97 g, 4 mmol) in $CH_3CN$ (15 mL) was added $POCl_3$ (612 mg, 4 mmol). The mixture was heated at 70° C. with stirring for 2 hrs. After being cooled to rt, the mixture was concentrated under reduced pressure. The residue was dissolved in $CH_3CN$. The resulting solution was basified with ammonia water to pH=10 at 0° C. and allowed to warm to rt and stirred at rt for 1 hr. The mixture was extracted with $CH_2Cl_2$ for three times. The combined organic layers were washed with brine, dried over anhydrous $Na_2SO_4$ and concentrated under reduced pressure to give crude benzyl 8-methoxy-9-(3-methoxypropoxy)-3,4,4a,10b-tetrahydro-1H-benzo[c][1,6]naphthyridine-2-carboxylate (1.69 g) as an orange oil which was directly used in the next step without further purification.

Step 5: Preparation of 2-benzyl 7-ethyl 11-methoxy-12-(3-methoxypropoxy)-8-oxo-4,4a,8,9,9a,13b-hexahydro-1H-benzo[c]pyrido[1,2-a][1,6]naphthyridine-2,7(3H)-dicarboxylate

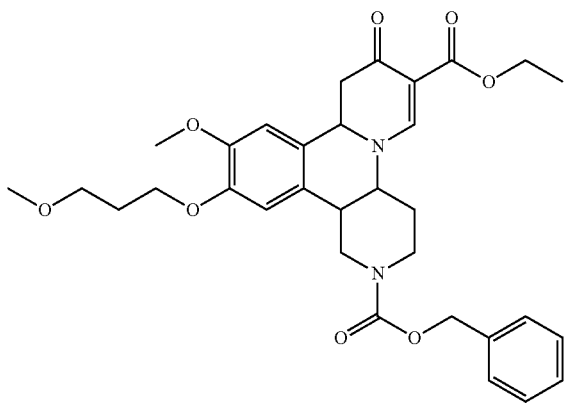 [SMILES: CCOC(=O)C1=CN2C(CC1=O)c1cc(OC)c(OCCCOC)cc1C1CN(C(=O)OCc3ccccc3)CCC12]

A mixture of crude benzyl 8-methoxy-9-(3-methoxypropoxy)-3,4,4a,10b-tetrahydro-1H-benzo[c][1,6]naphthyridine-2-carboxylate (1.69 g, 4 mmol) and ethyl 2-(ethoxymethylene)-3-oxo-butanoate (2.23 g, 12 mmol) in ethanol (20 mL) was heated at 100° C. with stirring overnight. After being cooled to rt, the mixture was concentrated under reduced pressure to give crude 2-benzyl 7-ethyl 11-methoxy-12-(3-methoxypropoxy)-8-oxo-4,4a,8,9,9a,13b-hexahydro-1H-benzo[c]pyrido[1,2-a][1,6]naphthyridine-2,7(3H)-dicarboxylate (3.70 g) as a brown oil which was directly used in the next step without further purification.

Step 6: Preparation of 2-benzyl 7-ethyl 11-methoxy-12-(3-methoxypropoxy)-8-oxo-4,4a,8,13b-tetrahydro-1H-benzo[c]pyrido[1,2-a][1,6]naphthyridine-2,7(3H)-dicarboxylate

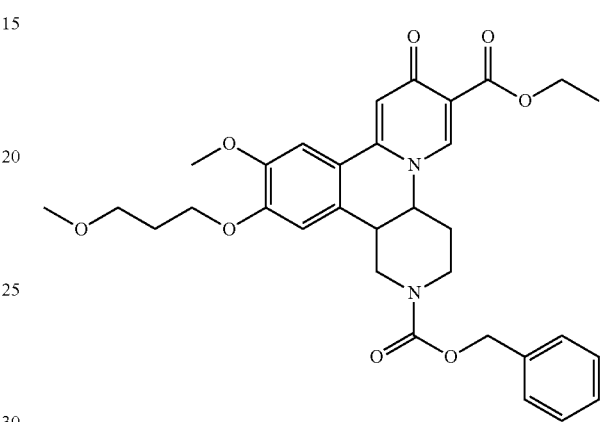

A mixture of crude 2-benzyl 7-ethyl 11-methoxy-12-(3-methoxypropoxy)-8-oxo-4,4a,8,9,9a,13b-hexahydro-1H-benzo[c]pyrido[1,2-a][1,6]naphthyridine-2,7(3H)-dicarboxylate (3.70 g, 4 mmol) and p-chloranil (984 mg, 4 mmol) in DME (20 mL) was heated at 70° C. with stirring for 3 hrs under argon atmosphere. The mixture was concentrated under reduced pressure to give crude 2-benzyl 7-ethyl 11-methoxy-12-(3-methoxypropoxy)-8-oxo-4,4a,8,13b-tetrahydro-1H-benzo[c]pyrido[1,2-a][1,6]naphthyridine-2,7(3H)-dicarboxylate (4.91 g) as a dark brown solid which was directly used in the next step without further purification.

Step 7: Preparation of trans-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid and cis-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid

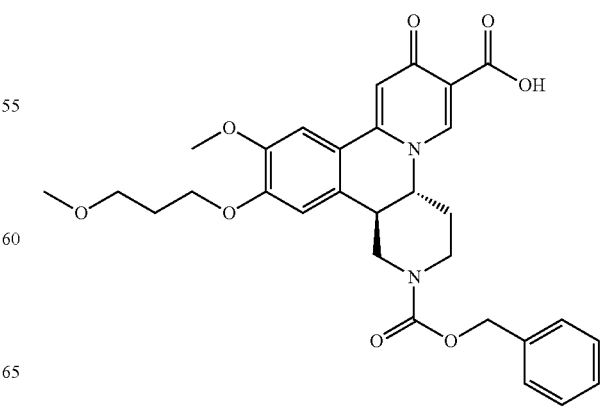

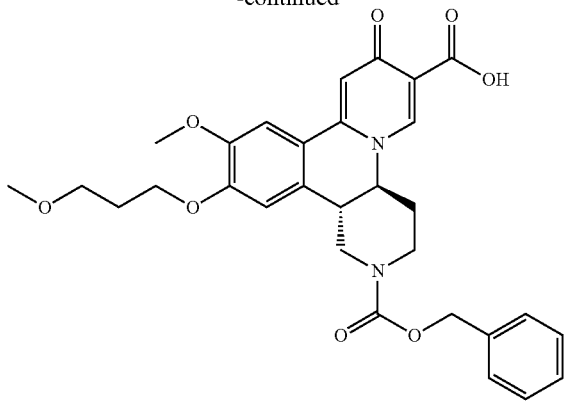

Example 29

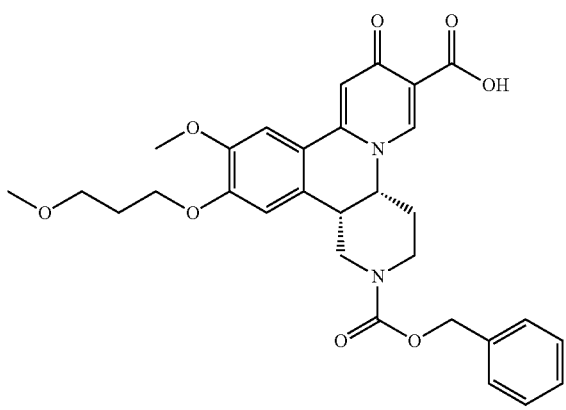 [SMILES: CCOC(=O)c1cn2c(cc1=O)-c1cc(OC)c(OCCCOC)cc1C1CN(C(=O)OCc3ccccc3)CCC12]

Example 30

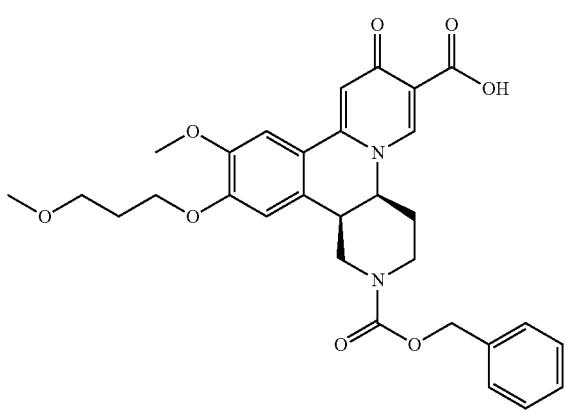

Example 30

To a solution of crude 2-benzyl 7-ethyl 11-methoxy-12-(3-methoxypropoxy)-8-oxo-4,4a,8,13b-tetrahydro-1H-benzo[c]pyrido[1,2-a][1,6]naphthyridine-2,7(3H)-dicarboxylate (4.91 g, 4 mmol) in methanol (20 mL) and H₂O (4 mL) was added LiOH.H₂O (1.34 g, 32 mmol). The mixture was stirred at rt overnight, then acidified with 1 M hydrochloric acid to pH=2-3, and extracted with CH₂Cl₂ for three times. The combined organic layers were washed with brine, dried over anhydrous Na₂SO₄ and concentrated under reduced pressure. The residue was purified by column chromatography and prep-HPLC to afford trans-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid (5 mg) as an off-white solid and cis-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid (23 mg) as a white solid.

Example 29

$^1$H NMR (400 MHz, DMSO-$d_6$) δ ppm 8.53 (s, 1H), 7.57 (s, 1H), 7.47 (s, 1H), 7.44-7.30 (m, 5H), 6.93 (s, 1H), 5.16 (s, 2H), 4.91 (d, 1H), 4.36 (d, 1H), 4.18 (t, 2H), 4.08-3.98 (m, 1H), 3.91 (s, 3H), 3.48 (t, 2H), 3.26 (s, 3H), 3.02 (br. s., 3H), 2.66 (d, 1H), 1.99 (quin, 3H). MS obsd. (ESI$^+$) [(M+H)$^+$]: 549.

Example 30

MS obsd. (ESI$^+$) [(M+H)$^+$]: 549.

Example 31 and 32: Trans-12-benzyloxy-11-methoxy-8-oxo-1,2,3,4,4a,13b-hexahydropyrido[1,2-f]phenanthridine-7-carboxylic acid and cis-12-benzyloxy-11-methoxy-8-oxo-1,2,3,4,4a,13b-hexahydropyrido[1,2-f]phenanthridine-7-carboxylic acid

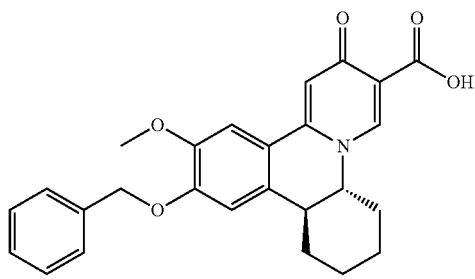

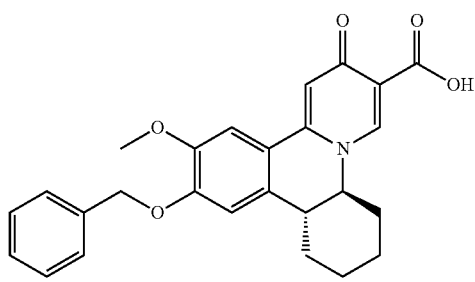

Example 31

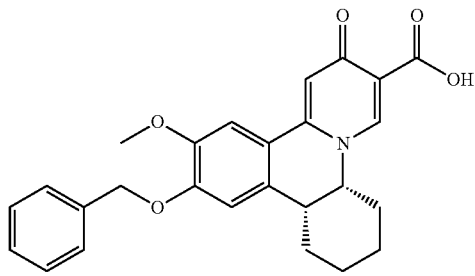

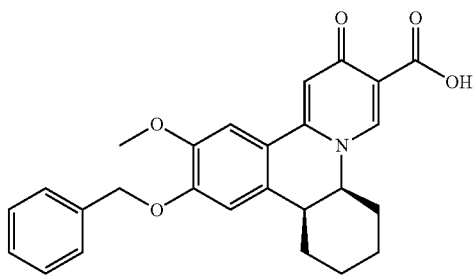

Example 32

Step 1: Preparation of
2-(3-benzyloxy-4-methoxy-phenyl)cyclohexanone

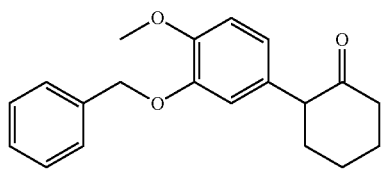 [SMILES: COc1ccc(C2CCCCC2=O)cc1OCc1ccccc1]

To a solution of 2-benzyloxy-4-bromo-1-methoxy-benzene (5.0 g, 17.1 mmol) in anhydrous dioxane (80 mL) was added cyclohexanone (2.0 g, 20.5 mmol), palladium acetate (38.2 mg, 0.17 mmol), tri-tert-butylphosphonium tetrafluoroborate (59.2 mg, 0.20 mmol) and lithium bis(trimethylsilyl)amide (1.3 mol/L, 26.3 mL, 34.2 mmol). The reaction mixture was heated with stirring at 60° C. for 3 hrs under argon atmosphere, then cooled to rt and concentrated under reduced pressure. The residue was partitioned between brine and DCM. The organic layer was separated, dried over anhydrous $Na_2SO_4$ and concentrated under reduced pressure. The residue was purified by column chromatography to give 2-(3-benzyloxy-4-methoxy-phenyl)cyclohexanone (300 mg).

Step 2: Preparation of
2-(3-benzyloxy-4-methoxy-phenyl)cyclohexanamine

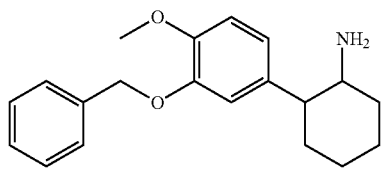 [SMILES: COc1ccc(C2CCCCC2N)cc1OCc1ccccc1]

To a solution of 2-(3-benzyloxy-4-methoxy-phenyl)cyclohexanone (250 mg, 0.81 mmol) in MeOH (30 mL) was added ammonium acetate (624.5 mg, 8.1 mmol) and sodium cyanoborohydride (152.6 mg, 2.43 mmol) at rt. The reaction mixture was stirred at rt for 20 hrs, and then quenched with aqueous sodium hydroxide solution (4 mol/L). The resulting mixture was stirred at rt for 4 hrs, and then partitioned between brine DCM. The organic layer was separated, dried over anhydrous $Na_2SO_4$ and concentrated under reduced pressure to give crude 2-(3-benzyloxy-4-methoxy-phenyl) cyclohexanamine (230 mg), which was used in the next step without further purification.

Step 3: Preparation of N-[2-(3-benzyloxy-4-methoxy-phenyl)cyclohexyl]formamide

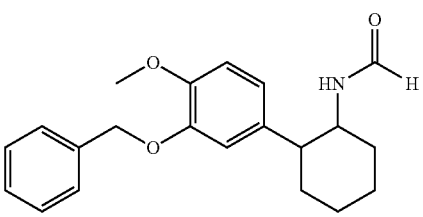 [SMILES: COc1ccc(C2CCCCC2NC=O)cc1OCc1ccccc1]

To a solution of 2-(3-benzyloxy-4-methoxy-phenyl)cyclohexanamine (230 mg, 0.74 mmol) in dioxane (10 mL) was added formic acid (83.7 µL, 2.22 mmol). The reaction mixture was heated at 80° C. with stirring for 16 hrs, then cooled to rt and concentrated under reduced pressure to give crude N-[2-(3-benzyloxy-4-methoxy-phenyl)cyclohexyl] formamide (240 mg), which was used in the next step without further purification.

Step 4: Preparation of 9-benzyloxy-8-methoxy-1,2,3,4,4a,10b-hexahydrophenanthridine

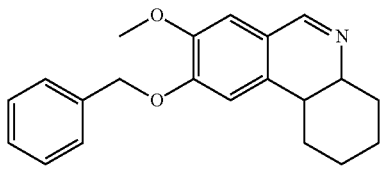 [SMILES: COc1cc2c(cc1OCc1ccccc1)C1CCCCC1N=C2]

To a solution of N-[2-(3-benzyloxy-4-methoxy-phenyl) cyclohexyl]formamide (240 mg, 0.71 mmol) in MeCN (10 mL) was added phosphorus oxychloride (0.1 mL, 1.1 mmol). The resulting mixture was heated at 50° C. with stirring for 2 hrs, and then concentrated under reduced pressure. The residue was partitioned between saturated aqueous $NaHCO_3$ solution and DCM. The organic layer was separated, dried over anhydrous $Na_2SO_4$ and concentrated under reduced pressure to give 9-benzyloxy-8-methoxy-1,2,3,4,4a,10b-hexahydrophenanthridine (200 mg), which was used in the next step without further purification.

Step 5: Preparation of ethyl 12-benzyloxy-11-methoxy-8-oxo-1,2,3,4,4a,9,9a,13b-octahydropyrido[1,2-f]phenanthridine-7-carboxylate

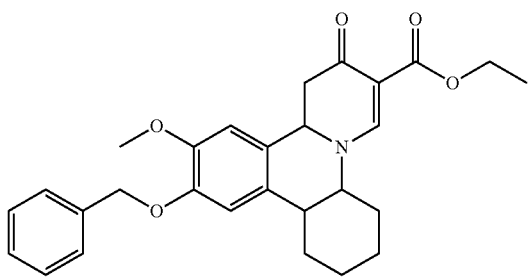 [SMILES: CCOC(=O)C1=CN2C(CC1=O)c1cc(OC)c(OCc3ccccc3)cc1C1CCCCC12]

To a solution of 9-benzyloxy-8-methoxy-1,2,3,4,4a,10b-hexahydrophenanthridine (200 mg, 0.62 mmol) in EtOH (10 mL) was added ethyl 2-(ethoxymethylene)-3-oxo-butanoate (463.6 mL, 2.49 mmol). The reaction mixture was heated at 100° C. with stirring for 16 hrs, and then concentrated under reduced pressure to give crude ethyl 12-benzyloxy-11-methoxy-8-oxo-1,2,3,4,4a,9,9a,13b-octahydropyrido[1,2-f]phenanthridine-7-carboxylate, which was used in the next step without further purification.

Step 6: Preparation of ethyl 12-benzyloxy-11-methoxy-8-oxo-1,2,3,4,4a,13b-hexahydropyrido[1,2-f]phenanthridine-7-carboxylate

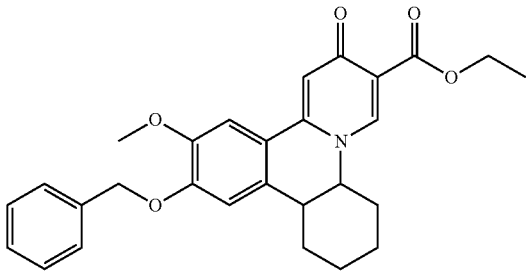 [SMILES: CCOC(=O)c1cn2c(cc1=O)-c1cc(OC)c(OCc3ccccc3)cc1C1CCCCC12]

To a solution of crude ethyl 12-benzyloxy-11-methoxy-8-oxo-1,2,3,4,4a,9,9a,13b-octahydropyrido[1,2-f]phenanthridine-7-carboxylate (all the crude product from the above step) in DME (10 mL) was added p-chloranil (106.7 mg, 0.43 mmol). The resulting mixture was heated at 70° C. with stirring for 2 hrs, then cooled to rt and concentrated under reduced pressure to give crude ethyl 12-benzyloxy-11-methoxy-8-oxo-1,2,3,4,4a,13b-hexahydropyrido[1,2-f]phenanthridine-7-carboxylate, which was used in the next step without further purification.

Step 7: Preparation of trans-12-benzyloxy-11-methoxy-8-oxo-1,2,3,4,4a,13b-hexahydropyrido[1,2-f]phenanthridine-7-carboxylic acid and cis-12-benzyloxy-11-methoxy-8-oxo-1,2,3,4,4a,13b-hexahydropyrido[1,2-f]phenanthridine-7-carboxylic acid

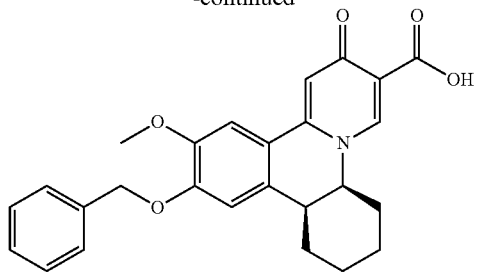

To a solution of crude ethyl 12-benzyloxy-11-methoxy-8-oxo-1,2,3,4,4a,13b-hexahydropyrido[1,2-f]phenanthridine-7-carboxylate (all the crude product from the above step) in a mixture solvent of methanol (9 mL) and water (3 mL) was added LiOH H$_2$O (78.1 mg, 1.86 mmol). The reaction mixture was stirred at rt for 2 hrs, and then acidified with 6 M hydrochloric acid. The resulting mixture was partitioned between brine and DCM. The organic layer was separated, dried over anhydrous Na$_2$SO$_4$ and concentrated under reduced pressure. The residue was purified by preparative HPLC to give trans-12-benzyloxy-11-methoxy-8-oxo-1,2,3,4,4a,13b-hexahydropyrido[1,2-f]phenanthridine-7-carboxylic acid (41 mg) and cis-12-benzyloxy-11-methoxy-8-oxo-1,2,3,4,4a,13b-hexahydropyrido[1,2-f]phenanthridine-7-carboxylic acid (5 mg).

Example 31

$^1$H NMR (400 MHz, DMSO-d$_6$): δ ppm 8.62 (s, 1H), 7.55 (s, 1H), 7.52-7.32 (m, 6H), 7.11 (s, 1H), 5.24 (s, 2H), 3.91 (s, 3H), 3.80-3.71 (m, 1H), 2.86-2.76 (m, 1H), 2.69-2.57 (m, 2H), 2.08-2.00 (m, 1H), 1.90-1.72 (m, 2H), 1.50-1.20 (m, 3H). MS obsd. (ESI$^+$) [(M+H)$^+$]: 432.

Example 32

$^1$H NMR (400 MHz, Acetone-d$_6$): δ ppm 8.63 (s, 1H), 7.61 (s, 1H), 7.58-7.52 (m, 2H), 7.47-7.41 (m, 2H), 7.37-7.34 (m, 1H), 7.22 (s, 1H), 7.18 (s, 1H), 5.33 (s, 2H), 4.74-4.62 (m, 1H), 4.02 (s, 3H), 3.69-3.59 (m, 1H), 2.68-2.63 (m, 2H), 1.95-1.83 (m, 2H), 1.61-1.46 (m, 3H), 1.34-1.20 (m, 1H). MS obsd. (ESI$^+$) [(M+H)$^+$]: 432.

Example 33 and 34: Trans-11-methoxy-12-(3-methoxypropoxy)-8-oxo-1,3,4,4a,8,13b-hexahydropyrano[4,3-c]pyrido[2,1-a]isoquinoline-7-carboxylic acid and cis-11-methoxy-12-(3-methoxypropoxy)-8-oxo-1,3,4,4a,8,13b-hexahydropyrano[4,3-c]pyrido[2,1-a]isoquinoline-7-carboxylic acid

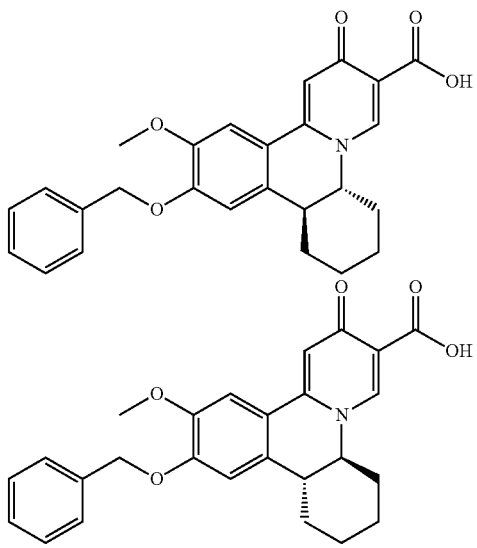

Example 31

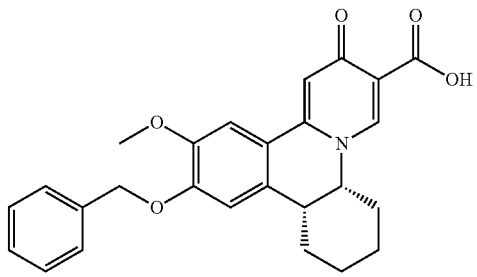

Example 32

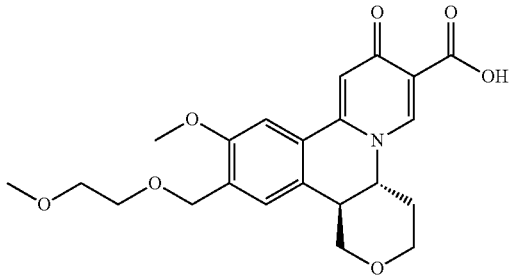

Example 33

69

-continued

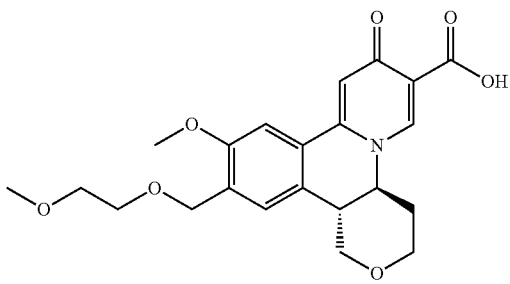

Example 34

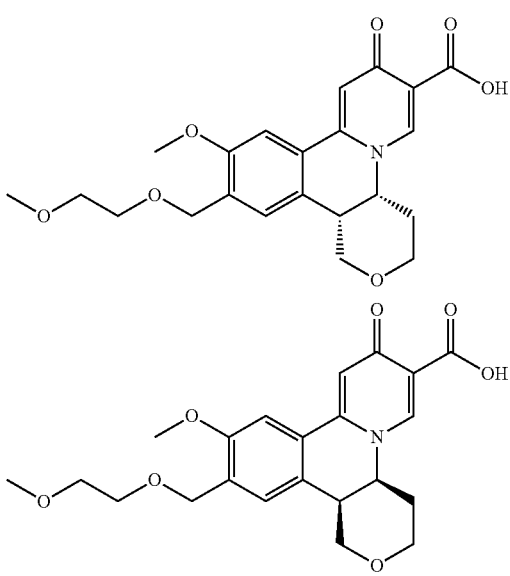

Step 1: Preparation of 3-[4-methoxy-3-(3-methoxy-propoxy)phenyl]tetrahydropyran-4-one

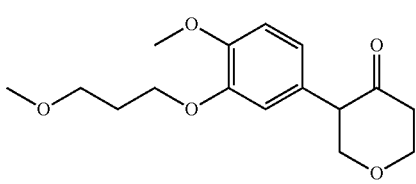 [SMILES: COCCCOc1cc(C2COCCC2=O)ccc1OC]

To a solution of 4-bromo-1-methoxy-2-(3-methoxypropoxy)benzene (5.0 g, 18.2 mmol) in anhydrous toluene (80 mL) was added tetrahydropyran-4-one (7.3 g, 72.8 mmol), palladium acetate (40.9 mg, 0.18 mmol), 4,5-bis(diphenylphosphino)-9,9-dimethylxanthene (210.6 mg, 0.36 mmol) and cesium carbonate (11.9 g, 36.4 mmol). The reaction mixture was heated at 100° C. with stirring for 24 hrs under argon atmosphere. After being cooled to rt, the mixture was concentrated under reduced pressure. The residue was partitioned between brine and DCM. The organic layer was separated, dried over anhydrous Na$_2$SO$_4$ and concentrated under reduced pressure. The residue was purified by column chromatography to give 3-[4-methoxy-3-(3-methoxypropoxy)phenyl]tetrahydropyran-4-one (200 mg).

70

Step 2: Preparation of 3-[4-methoxy-3-(3-methoxypropoxy)phenyl]tetrahydropyran-4-amine

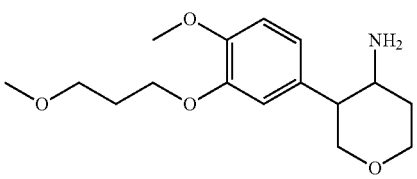 [SMILES: COCCCOc1cc(C2COCCC2N)ccc1OC]

To a solution of 3-[4-methoxy-3-(3-methoxypropoxy)phenyl]tetrahydropyran-4-one (200 mg, 0.68 mmol) in MeOH (30 mL) was added ammonium acetate (524.3 mg, 6.8 mmol) and sodium cyanoborohydride (128.1 mg, 2.04 mmol) at rt. The reaction mixture was stirred for 16 hours at rt, and then quenched with aqueous sodium hydroxide solution. The resulting mixture was stirred at rt for 4 hrs, then partitioned between brine and DCM. The organic layer was separated, dried over anhydrous Na$_2$SO$_4$ and concentrated under reduced pressure to give crude 3-[4-methoxy-3-(3-methoxypropoxy)phenyl]tetrahydropyran-4-amine (200 mg), which was used in the next step without further purification.

Step 3: Preparation of N-[3-[4-methoxy-3-(3-methoxypropoxy)phenyl]tetrahydropyran-4-yl]formamide

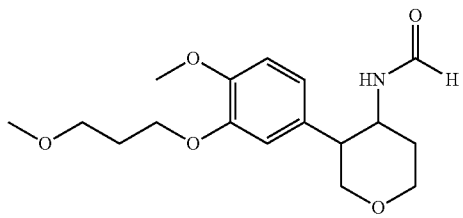 [SMILES: COCCCOc1cc(C2COCCC2NC=O)ccc1OC]

To a solution of 3-[4-methoxy-3-(3-methoxypropoxy)phenyl]tetrahydropyran-4-amine (200 mg, 0.68 mmol) in dioxane (10 mL) was added formic acid (76.9 μL, 2.04 mmol). The reaction mixture was heated at 100° C. with stirring for 18 hrs. After being cooled to rt, the mixture was concentrated under reduced pressure to give crude N-[3-[4-methoxy-3-(3-methoxypropoxy)phenyl]tetrahydropyran-4-yl]formamide (210 mg), which was used in the next step without further purification.

Step 4: Preparation of 8-methoxy-9-(3-methoxypropoxy)-3,4,4a,10b-tetrahydro-1H-pyrano[4,3-c]isoquinoline

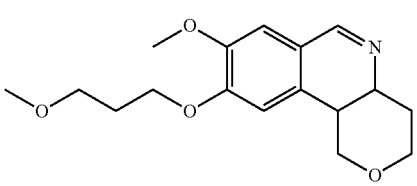

To a solution of N-[3-[4-methoxy-3-(3-methoxypropoxy)phenyl]tetrahydropyran-4-yl]formamide (210 mg, 0.65 mmol) in MeCN (10 mL) was added phosphorus oxychloride (0.12 mL, 1.3 mmol). The reaction mixture was heated at 50° C. with stirring for 3 hrs, and then concentrated under reduced pressure. The residue was partitioned between saturated aqueous NaHCO$_3$ solution and DCM. The organic layer was separated, dried over anhydrous Na$_2$SO$_4$ and concentrated under reduced pressure to give 8-methoxy-9-(3-methoxypropoxy)-3,4,4a,10b-tetrahydro-1H-pyrano[4,3-c]isoquinoline (198 mg), which was used in the next step without further purification.

Step 5: Preparation of ethyl 11-methoxy-12-(3-methoxypropoxy)-8-oxo-1,3,4,4a,8,9,9a,13b-octahydropyrano[4,3-c]pyrido[2,1-a]isoquinoline-7-carboxylate

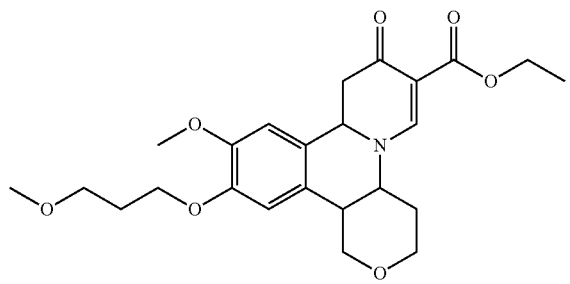 [SMILES: CCOC(=O)C1=CN2C(CC1=O)c1cc(OC)c(OCCCOC)cc1C1COCCC12]

To a solution of 8-methoxy-9-(3-methoxypropoxy)-3,4,4a,10b-tetrahydro-1H-pyrano[4,3-c]isoquinoline (198 mg, 0.65 mmol) in EtOH (10 mL) was added ethyl 2-(ethoxymethylene)-3-oxo-butanoate (363.1 mg, 1.95 mmol). The reaction mixture was heated at 110° C. with stirring for 20 hrs. After being cooled to rt, the mixture was concentrated under reduced pressure to give crude ethyl 11-methoxy-12-(3-methoxypropoxy)-8-oxo-1,3,4,4a,8,9,9a,13b-octahydropyrano[4,3-c]pyrido[2,1-a]isoquinoline-7-carboxylate, which was used in the next step without further purification.

Step 6: Preparation of ethyl 11-methoxy-12-(3-methoxypropoxy)-8-oxo-1,3,4,4a,8,13b-hexahydropyrano[4,3-c]pyrido[2,1-a]isoquinoline-7-carboxylate

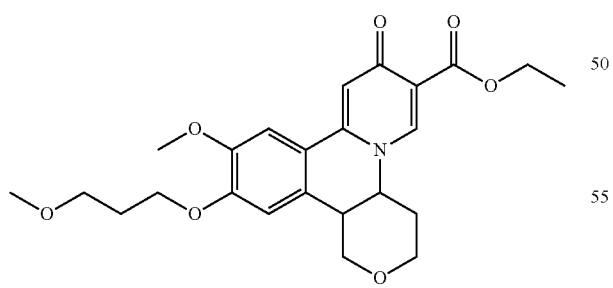

To a solution of crude ethyl 11-methoxy-12-(3-methoxypropoxy)-8-oxo-1,3,4,4a,8,9,9a,13b-octahydropyrano[4,3-c]pyrido[2,1-a]isoquinoline-7-carboxylate (all the crude product from the above step) in DME (10 mL) was added p-chloranil (113.1 mg, 0.46 mmol). The reaction mixture was heated at 70° C. with stirring for 3 hrs, and then concentrated under reduced pressure to give crude ethyl 11-methoxy-12-(3-methoxypropoxy)-8-oxo-1,3,4,4a,8,13b-hexahydropyrano[4,3-c]pyrido[2,1-a]isoquinoline-7-carboxylate, which was used in the next step without further purification.

Step 7: Preparation of trans-11-methoxy-12-(3-methoxypropoxy)-8-oxo-1,3,4,4a,8,13b-hexahydropyrano[4,3-c]pyrido[2,1-a]isoquinoline-7-carboxylic acid and cis-11-methoxy-12-(3-methoxypropoxy)-8-oxo-1,3,4,4a,8,13b-hexahydropyrano[4,3-c]pyrido[2,1-a]isoquinoline-7-carboxylic acid Example 33

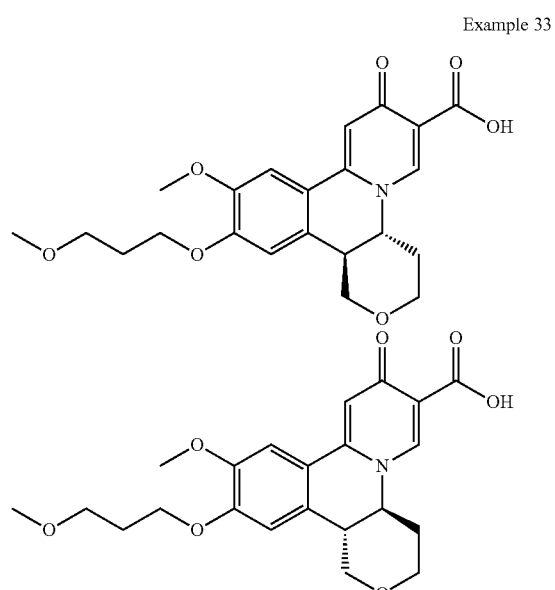

Example 34

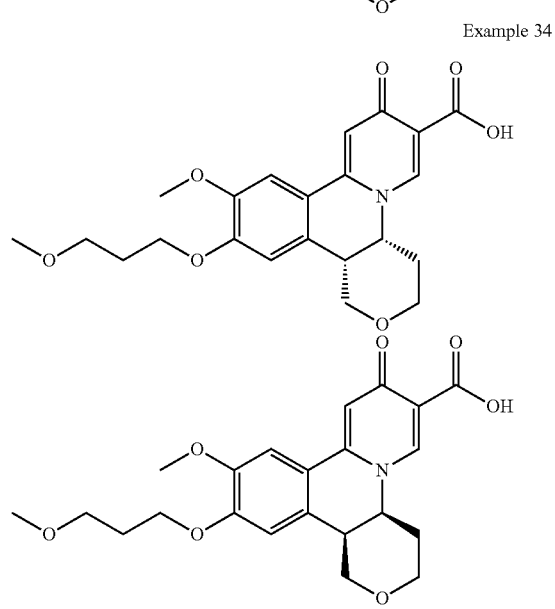

To a solution of crude ethyl 11-methoxy-12-(3-methoxypropoxy)-8-oxo-1,3,4,4a,8,13b-hexahydropyrano[4,3-c]pyrido[2,1-a]isoquinoline-7-carboxylate (all the crude product from the above step) in a mixture solvent of methanol (9 mL) and water (3 mL) was added LiOH H$_2$O (81.9 mg, 1.95 mmol). The reaction mixture was stirred at rt for 2 hrs, and then acidified with 6 M hydrochloric acid. The resulting mixture was partitioned between brine and DCM. The organic layer was separated and concentrated under reduced pressure. The residue was purified by preparative HPLC to give trans-11-methoxy-12-(3-methoxypropoxy)-8-oxo-1,3,4,4a,8,13b-hexahydropyrano[4,3-c]pyrido[2,1-a]isoquinoline-7-carboxylic acid (15 mg) and cis-11-methoxy-12-(3-methoxypropoxy)-8-oxo-1,3,4,4a,8,13b-hexahydropyrano[4,3-c]pyrido[2,1-a]isoquinoline-7-carboxylic acid (3 mg).

Example 33

$^1$H NMR (400 MHz, CDCl$_3$) δ ppm 8.69 (s, 1H), 7.25 (s, 1H), 7.12 (s, 1H), 6.68 (s, 1H), 4.80-4.69 (m, 1H), 4.44-4.34 (m, 1H), 4.25-4.15 (m, 2H), 3.96 (s, 3H), 3.93-3.84 (m, 1H), 3.64-3.55 (m, 4H), 3.39 (s, 3H), 3.13-2.98 (m, 1H), 2.64-2.54 (m, 1H), 2.20-2.13 (m, 3H). MS obsd. (ESI$^+$) [(M+H)$^+$]: 416.

Example 34

$^1$H NMR (400 MHz, CD$_3$CN) δ ppm 8.61 (s, 1H), 7.41 (s, 1H), 7.22 (s, 1H), 7.13 (s, 1H), 4.78-4.69 (m, 2H), 4.22-4.11 (m, 2H), 3.93 (s, 3H), 3.89-3.83 (m, 1H), 3.79-3.73 (m, 1H), 3.58-3.52 (m, 3H), 3.43-3.37 (m, 1H), 3.33 (s, 3H), 2.06-2.01 (m, 2H), 1.83-1.73 (m, 2H). MS obsd. (ESI$^+$) [(M+H)$^+$]: 416.

Example 35 and 36: Trans-11-methoxy-12-(3-methoxypropoxy)-8-oxo-1,3,4,4a,8,13b-hexahydropyrido[2,1-a]thiopyrano[4,3-c]isoquinoline-7-carboxylic acid and cis-11-methoxy-12-(3-methoxypropoxy)-8-oxo-1,3,4,4a,8,13b-hexahydropyrido[2,1-a]thiopyrano[4,3-c]isoquinoline-7-carboxylic acid Example 35

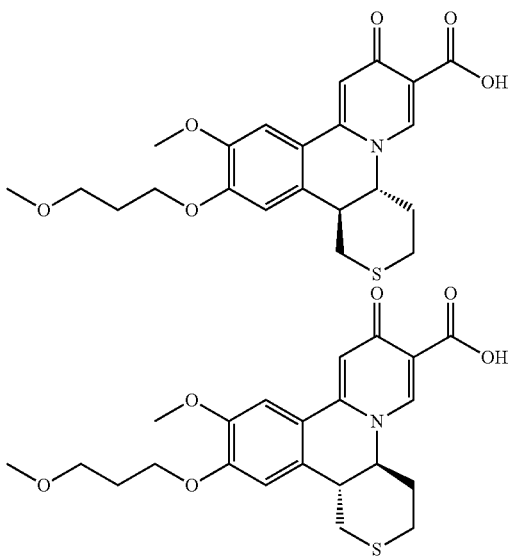

Example 36

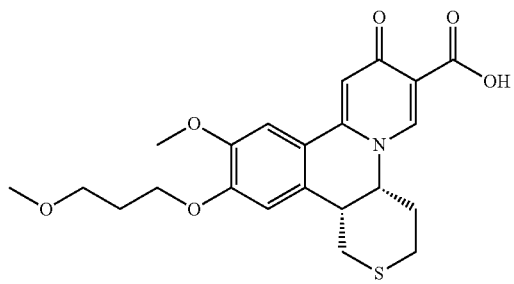

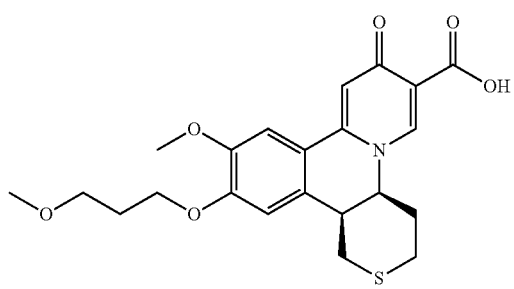

Step 1: Preparation of tert-butyl 3-[4-methoxy-3-(3-methoxypropoxy)phenyl]-4-oxo-piperidine-1-carboxylate

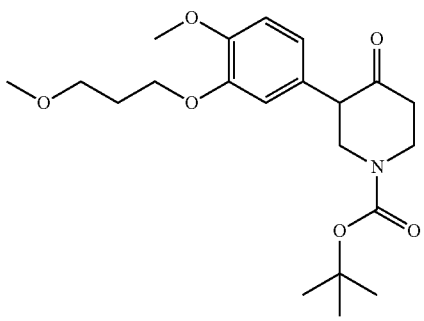 [SMILES: COCCCOc1cc(C2CN(C(=O)OC(C)(C)C)CCC2=O)ccc1OC]

To a solution of 4-bromo-1-methoxy-2-(3-methoxypropoxy)benzene (10.0 g, 36.4 mmol) in anhydrous THF (150 mL) was added tert-butyl 4-oxopiperidine-1-carboxylate (8.71 g, 43.7 mmol), tris(dibenzylideneacetone)dipalladium(0) (329.7 mg, 0.36 mmol), 2-(dicyclohexylphosphino)-2'-methylbiphenyl (266.1 mg, 0.73 mmol) and sodium tert-butoxide (5.25 g, 54.6 mmol). The reaction mixture was heated at 60° C. for 6 hrs under argon atmosphere. After being cooled to rt, the mixture was cooled to rt and concentrated under reduced pressure. The residue was partitioned between brine and DCM. The organic layer was separated, dried over anhydrous Na$_2$SO$_4$ and concentrated under reduced pressure. The residue was purified by column chromatography to give tert-butyl 3-[4-methoxy-3-(3-methoxypropoxy)phenyl]-4-oxo-piperidine-1-carboxylate (4.0 g).

Step 2: Preparation of 3-[4-methoxy-3-(3-methoxypropoxy)phenyl]piperidin-4-one

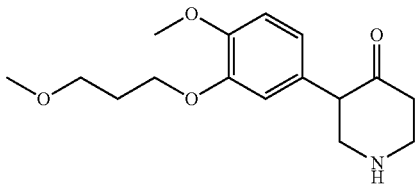 [SMILES: COCCCOc1cc(C2CNCCC2=O)ccc1OC]

To a solution of tert-butyl 3-[4-methoxy-3-(3-methoxypropoxy)phenyl]-4-oxo-piperidine-1-carboxylate (4.0 g) in MeCN (50 mL) was added 6 M hydrochloric acid (10 mL). The mixture was stirred at rt for 30 minutes, then basified with aqueous NaHCO₃ solution and extracted with EtOAc. The organic layer was separated, dried over anhydrous Na₂SO₄ and concentrated under reduced pressure to give 3-[4-methoxy-3-(3-methoxypropoxy)phenyl]piperidin-4-one (2.5 g), which was used in the next step without further purification.

Step 3: Preparation of 3-[4-methoxy-3-(3-methoxypropoxy)phenyl]-1-methyl-piperidin-4-one

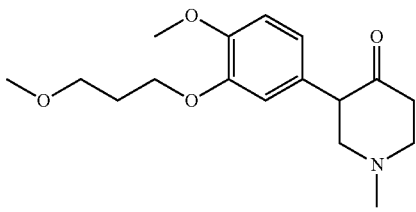 [SMILES: COCCCOc1cc(C2CN(C)CCC2=O)ccc1OC]

To a solution of 3-[4-methoxy-3-(3-methoxypropoxy)phenyl]piperidin-4-one (2.5 g, 12.9 mmol) in MeCN (40 mL) was added K₂CO₃ (3.56 g, 25.8 mmol) and iodomethane (1.2 mL, 19.4 mmol). The reaction was stirred at rt for 16 hrs, and then filtered. The filtrate was concentrated under reduced pressure. The residue was purified by column chromatography to give 3-[4-methoxy-3-(3-methoxypropoxy)phenyl]-1-methyl-piperidin-4-one (2.0 g).

Step 4: Preparation of 3-[4-methoxy-3-(3-methoxypropoxy)phenyl]tetrahydrothiopyran-4-one

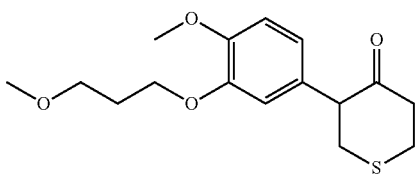 [SMILES: COCCCOc1cc(C2CSCCC2=O)ccc1OC]

To a solution of 3-[4-methoxy-3-(3-methoxypropoxy)phenyl]-1-methyl-piperidin-4-one (2.0 g, 6.5 mmol) in isobutyl methylketone (20 mL) was added methyl trifluoromethanesulfonate (0.69 mL, 6.5 mmol) slowly at ° C. The mixture was allowed to warm to rt and stirred for 30 minutes at rt. To the above mixture was added a solution of sodium hydrogen sulfide (1.82 g, 32.5 mmol) and sodium sulfide nonahydrate (1.56 g, 6.5 mmol) in water (10 mL). The resulting mixture was heated at 100° C. with stirring for 4 hrs. After being cooled to rt, the mixture was partitioned between brine and EtOAc. The organic layer was separated, dried over anhydrous Na₂SO₄ and concentrated under reduced pressure. The residue was purified by column chromatography to give 3-[4-methoxy-3-(3-methoxypropoxy)phenyl]tetrahydrothiopyran-4-one (600 mg).

Step 5: Preparation of 3-[4-methoxy-3-(3-methoxypropoxy)phenyl]tetrahydrothiopyran-4-amine

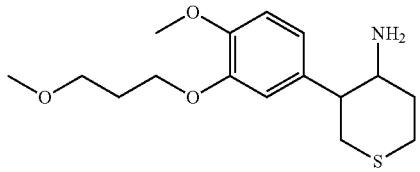 [SMILES: COCCCOc1cc(C2CSCCC2N)ccc1OC]

To a solution of 3-[4-methoxy-3-(3-methoxypropoxy)phenyl]tetrahydrothiopyran-4-one (0.6 g, 1.93 mmol) in MeOH (50 mL) was added ammonium acetate (2.2 g, 28.95 mmol) and sodium cyanoborohydride (0.36 g, 5.79 mmol). The reaction mixture was stirred at rt for 24 hrs, and then quenched with 4 M sodium hydroxide aqueous solution. The resulting mixture was stirred at rt for 4 hrs, and then partitioned between brine and DCM. The organic layer was separated, dried over anhydrous Na₂SO₄ and concentrated under reduced pressure to give 3-[4-methoxy-3-(3-methoxypropoxy)phenyl]tetrahydrothiopyran-4-amine, which was used in the next step without further purification.

Step 6: Preparation of N-[3-[4-methoxy-3-(3-methoxypropoxy)phenyl]tetrahydrothiopyran-4-yl]formamide

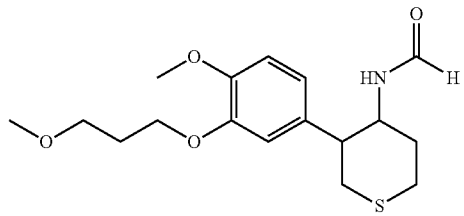 [SMILES: COCCCOc1cc(C2CSCCC2NC=O)ccc1OC]

To a solution of crude 3-[4-methoxy-3-(3-methoxypropoxy)phenyl]tetrahydropyran-4-amine (all the crude product from the above step) in dioxane (10 mL) was added formic acid (0.22 mL, 5.79 mmol). The reaction mixture was heated at 100° C. with stirring for 14 hrs. After being cooled to rt, the mixture was concentrated under reduced pressure. The residue was purified by column chromatography to give N-[3-[4-methoxy-3-(3-methoxypropoxy)phenyl]tetrahydro-thiopyran-4-yl]formamide (0.52 g).

Step 7: Preparation of 8-methoxy-9-(3-methoxy-propoxy)-3,4,4a,10b-tetrahydro-1H-thiopyrano[4,3-c]isoquinoline

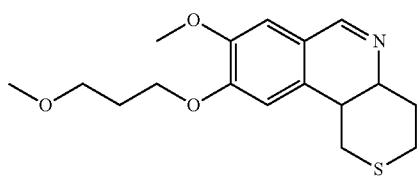

To a solution of N-[3-[4-methoxy-3-(3-methoxypropoxy)phenyl]tetrahydrothiopyran-4-yl]formamide (0.52 g, 1.53 mmol) in MeCN (10 mL) was added phosphorus oxychloride (0.21 mL, 2.3 mmol). The reaction mixture was heated at 50° C. for 3 hrs, and then concentrated under reduced pressure. The residue was partitioned between saturated aqueous NaHCO₃ solution and DCM. The organic layer was separated, dried over anhydrous Na₂SO₄ and concentrated under reduced pressure to give crude 8-methoxy-9-(3-methoxypropoxy)-3,4,4a,10b-tetrahydro-1H-thiopyrano[4,3-c]isoquinoline, which was used in the next step without further purification.

Step 8: Preparation of ethyl 11-methoxy-12-(3-methoxypropoxy)-8-oxo-1,3,4,4a,8,9,9a,13b-octahydropyrido[2,1-a]thiopyrano[4,3-c]isoquinoline-7-carboxylate

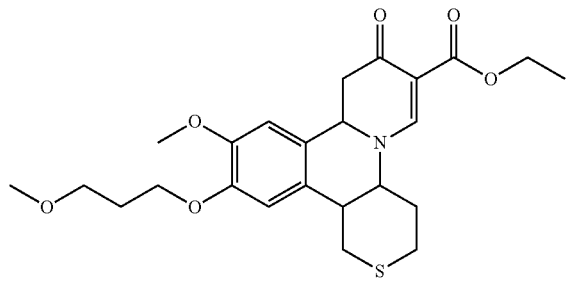 [SMILES: CCOC(=O)C1=CN2C(CC1=O)c1cc(OC)c(OCCCOC)cc1C1CSCCC12]

To a solution of crude 8-methoxy-9-(3-methoxypropoxy)-3,4,4a,10b-tetrahydro-1H-thiopyrano[4,3-c]isoquinoline (all the crude product from the above step) in EtOH (10 mL) was added ethyl 2-(ethoxymethylene)-3-oxo-butanoate (0.85 g, 4.59 mmol). The reaction mixture was heated at 100° C. for 18 hrs. After being cooled to rt, the mixture was concentrated under reduced pressure to give crude ethyl 11-methoxy-12-(3-methoxypropoxy)-8-oxo-1,3,4,4a,8,9,9a,13b-octahydropyrido[2,1-a]thiopyrano[4,3-c]isoquinoline-7-carboxylate, which was used in the next step without further purification.

Step 9: Preparation of ethyl 11-methoxy-12-(3-methoxypropoxy)-8-oxo-1,3,4,4a,8,13b-hexahydropyrido[2,1-a]thiopyrano[4,3-c]isoquinoline-7-carboxylate

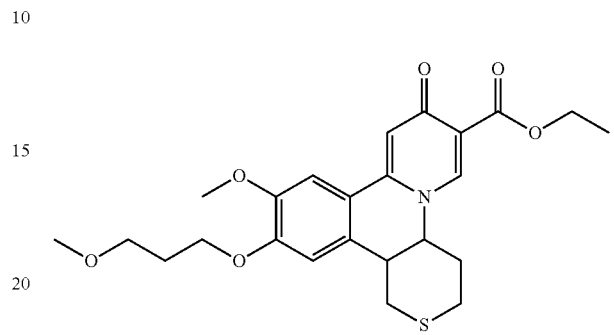

To a solution of crude ethyl 11-methoxy-12-(3-methoxypropoxy)-8-oxo-1,3,4,4a,8,9,9a,13b-octahydropyrido[2,1-a]thiopyrano[4,3-c]isoquinoline-7-carboxylate (all the crude product from the above step) in DME (10 mL) was added p-chloranil (0.26 g, 1.07 mmol). The reaction mixture was heated at 70° C. for 3 hrs, then concentrated under reduced pressure to give crude ethyl 11-methoxy-12-(3-methoxypropoxy)-8-oxo-1,3,4,4a,8,13b-hexahydropyrido[2,1-a]thiopyrano[4,3-c]isoquinoline-7-carboxylate, which was used in the next step without further purification.

Step 10: Preparation of trans-11-methoxy-12-(3-methoxypropoxy)-8-oxo-1,3,4,4a,8,13b-hexahydropyrido[2,1-a]thiopyrano[4,3-c]isoquinoline-7-carboxylic acid and cis-11-methoxy-12-(3-methoxypropoxy)-8-oxo-1,3,4,4a,8,13b-hexahydropyrido[2,1-a]thiopyrano[4,3-c]isoquinoline-7-carboxylic acid Example 35

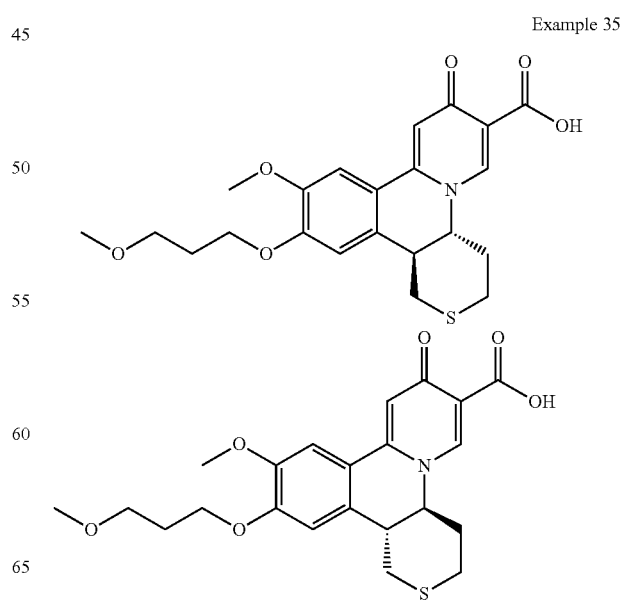

Example 36

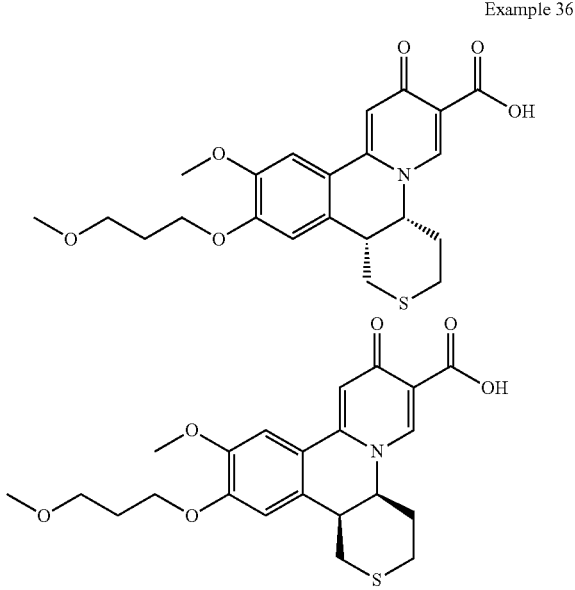

To a solution of crude ethyl 11-methoxy-12-(3-methoxypropoxy)-8-oxo-1,3,4,4a,8,13b-hexahydropyrido[2,1-a]thiopyrano[4,3-c]isoquinoline-7-carboxylate (all the crude product from the above step) in a mixture solvent of methanol (9 mL) and water (3 mL) was added LiOH H$_2$O (0.19 g, 4.59 mmol). The mixture was stirred at rt for 2 hrs, and then acidified with 6 M hydrochloric acid. The mixture was partitioned between brine and DCM. The organic layer was separated and concentrated under reduced pressure. The residue was purified by preparative HPLC to give trans-11-methoxy-12-(3-methoxypropoxy)-8-oxo-1,3,4,4a,8,13b-hexahydropyrido[2,1-a]thiopyrano[4,3-c]isoquinoline-7-carboxylic acid (26 mg) and cis-11-methoxy-12-(3-methoxypropoxy)-8-oxo-1,3,4,4a,8,13b-hexahydropyrido[2,1-a]thiopyrano[4,3-c]isoquinoline-7-carboxylic acid (4 mg).

Example 35

$^1$H NMR (400 MHz, DMSO-d$_6$) δ ppm 8.60 (s, 1H), 7.54 (s, 1H), 7.43 (s, 1H), 7.11 (s, 1H), 4.19-4.12 (m, 2H), 3.96-3.85 (m, 4H), 3.78-3.65 (m, 1H), 3.50-3.43 (m, 2H), 3.26 (s, 3H), 3.14-3.05 (m, 1H), 3.07-2.92 (m, 1H), 2.82-2.72 (m, 2H), 2.18-2.06 (m, 1H), 2.03-1.96 (m, 2H). MS obsd. (ESI$^+$) [(M+H)$^+$]: 432.

Example 36

$^1$H NMR (400 MHz, DMSO-d$_6$) δ ppm 8.80 (s, 1H), 7.54 (s, 1H), 7.46 (s, 1H), 7.09 (s, 1H), 4.77-4.68 (m, 1H), 4.20-4.07 (m, 2H), 3.90 (s, 3H), 3.80-3.75 (m, 1H), 3.65-3.57 (m, 1H), 3.51-3.46 (m, 2H), 3.26 (s, 3H), 3.17-3.09 (m, 1H), 2.85-2.76 (m, 1H), 2.04-1.90 (m, 4H), 1.65-1.52 (m, 1H). MS obsd. (ESI$^+$) [(M+H)$^+$]: 432.

Example 37: Trans-11-methoxy-12-(3-methoxypropoxy)-8-oxo-1,3,4,4a,8,13b-hexahydropyrido[2,1-a]thiopyrano[4,3-c]isoquinoline-7-carboxylic acid 2,2-dioxide

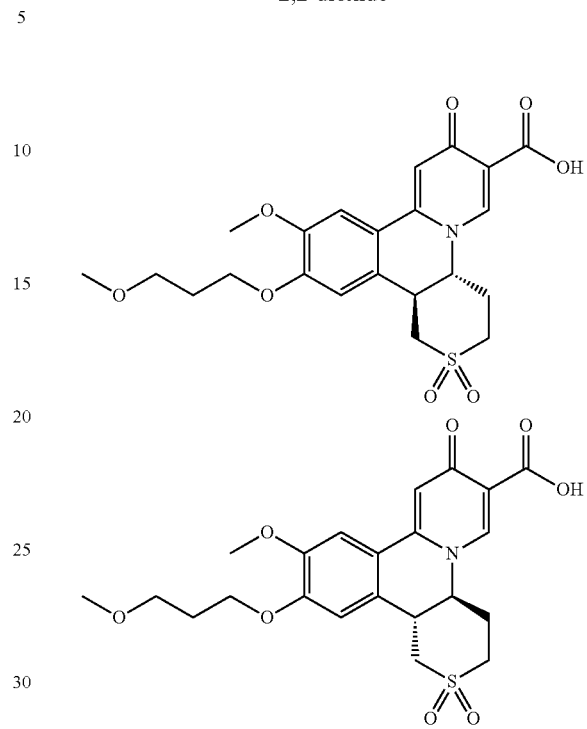

To a solution of trans-11-methoxy-12-(3-methoxypropoxy)-8-oxo-1,3,4,4a,8,13b-hexahydropyrido[2,1-a]thiopyrano[4,3-c]isoquinoline-7-carboxylic acid (20 mg, 0.05 mmol) in DCM (3 mL) was added 3-chloroperoxybenzoic acid (24.0 g, 0.1 mmol). The reaction mixture was stirred at rt for 30 hrs, and then concentrated under reduced pressure. The residue was purified by preparative HPLC to give trans-11-methoxy-12-(3-methoxypropoxy)-8-oxo-1,3,4a,8,13b-hexahydropyrido[2,1-a]thiopyrano[4,3-c]isoquinoline-7-carboxylic acid 2,2-dioxide (4 mg). $^1$H NMR (400 MHz, DMSO-d$_6$) δ ppm 8.69-8.59 (s, 1H), 7.57-7.51 (s, 1H), 7.46-7.40 (s, 1H), 7.10-7.04 (s, 1H), 4.39-4.31 (m, 1H), 4.20-4.08 (m, 3H), 3.91 (s, 3H), 3.72-3.61 (m, 1H), 3.54-3.43 (m, 3H), 3.26 (s, 3H), 3.19-3.16 (m, 4H), 2.05-1.92 (m, 2H). MS obsd. (ESI$^+$) [(M+H)$^+$]: 464.

Example 38: Cis-10-methoxy-3,3,11-trimethyl-7-oxo-1,2,3,3a,7,12b-hexahydrocyclopenta[c]pyrido[2,1-a]isoquinoline-6-carboxylic acid

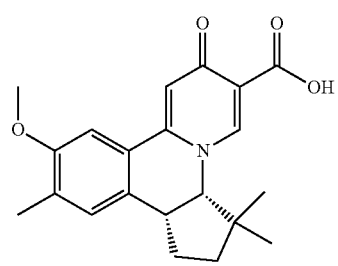

-continued

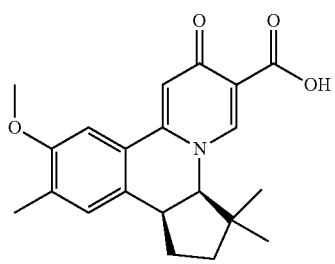

Step 1: Preparation of cis-ethyl 10-methoxy-3,3-dimethyl-7-oxo-11-(((trifluoromethyl)sulfonyl)oxy)-1,2,3,3a,7,12b-hexahydrocyclopenta[c]pyrido[2,1-a]isoquinoline-6-carboxylate

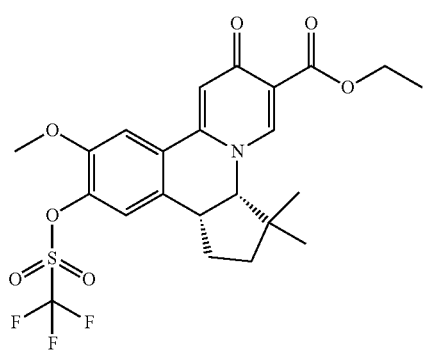

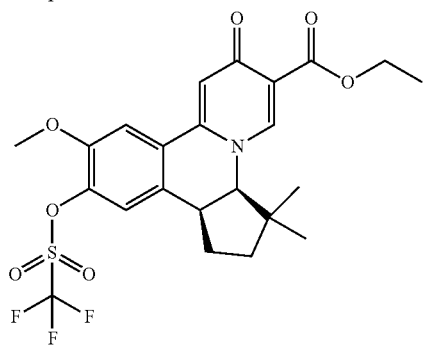

To a solution of cis-ethyl 11-hydroxy-10-methoxy-3,3-dimethyl-7-oxo-1,2,3,3a,7,12b-hexahydrocyclopenta[c]pyrido[2,1-a]isoquinoline-6-carboxylate (1.53 g, 4 mmol) and triethylamine (1.21 g, 12 mmol) in CH$_2$Cl$_2$ (15 mL) was added N-phenyl-bis(trifluoromethanesulfonimide) (2.14 g, 6 mmol) at 0° C. dropwise. The mixture was stirred at 0° C. to rt overnight, and then diluted with CH$_2$Cl$_2$. The resulting mixture was washed with 1 M hydrochloric acid and brine. The organic layer was dried over anhydrous Na$_2$SO$_4$ and concentrated under reduced pressure. The residue was purified by column chromatography to afford cis-ethyl 10-methoxy-3,3-dimethyl-7-oxo-11-(((trifluoromethyl)sulfonyl)oxy)-1,2,3,3a,7,12b-hexahydrocyclopenta[c]pyrido[2,1-a]isoquinoline-6-carboxylate (1.21 g) as a yellow solid.

Step 2: Preparation of cis-10-methoxy-3,3,11-trimethyl-7-oxo-1,2,3,3a,7,12b-hexahydrocyclopenta[c]pyrido[2,1-a]isoquinoline-6-carboxylic acid

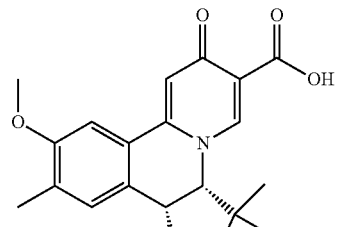

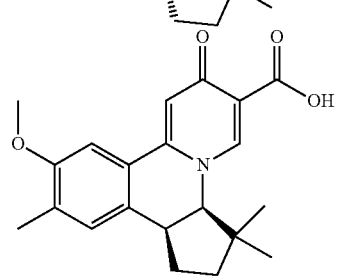

A mixture of cis-ethyl 10-methoxy-3,3-dimethyl-7-oxo-11-(((trifluoromethyl)sulfonyl)oxy)-1,2,3,3a,7,12b-hexahydrocyclopenta[c]pyrido[2,1-a]isoquinoline-6-carboxylate (103 mg, 0.2 mmol), methylboronic acid (24 mg, 0.4 mmol), K$_2$CO$_3$ (83 mg, 0.6 mmol) and Pd(dppf)Cl$_2$.CH$_2$Cl$_2$ (15 mg, 0.02 mmol) in THF (2.4 mL) and water (0.6 mL) was heated at 60° C. with stirring overnight under argon. After being cooled to rt, to the mixture was added 4 M sodium hydroxide solution (0.5 mL, 2 mmol). The resulting mixture was stirred at rt for 1 h, then diluted with water and acidified with 2 M hydrochloric acid to pH=2-3. The mixture was extracted with CH$_2$Cl$_2$ for three times. The combined organic layers were washed with brine, dried over anhydrous Na$_2$SO$_4$ and concentrated under reduced pressure. The residue was purified by prep-HPLC to afford cis-10-methoxy-3,3,11-trimethyl-7-oxo-1,2,3,3a,7,12b-hexahydrocyclopenta[c]pyrido[2,1-a]isoquinoline-6-carboxylic acid (17 mg) as a yellow solid. $^1$H NMR (400 MHz, CDCl$_3$) δ ppm 8.47 (s, 1H), 7.39 (s, 1H), 7.19 (s, 1H), 7.17 (s, 1H), 4.18 (d, 1H), 3.93 (s, 3H), 3.84-3.76 (m, 1H), 2.37-2.26 (m, 2H), 2.31 (s, 3H), 1.68 (ddd, 1H), 1.50 (td, 1H), 1.28 (s, 3H), 0.53 (s, 3H). MS obsd. (ESI$^+$) [(M+H)$^+$]: 354.

Example 39: Cis-10-methoxy-3,3,11-trimethyl-7-oxo-1,2,3,3a,7,12b-hexahydrocyclopenta[c]pyrido[2,1-a]isoquinoline-6-carboxylic acid

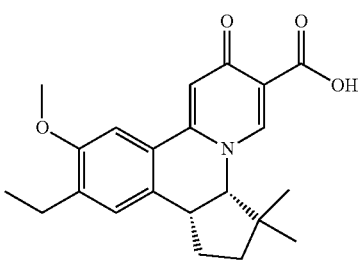

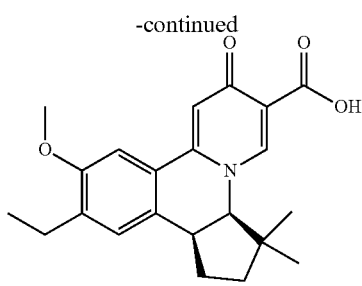

A mixture of cis-ethyl 10-methoxy-3,3-dimethyl-7-oxo-11-(((trifluoromethyl)sulfonyl)oxy)-1,2,3,3a,7,12b-hexahydrocyclopenta[c]pyrido[2,1-a]isoquinoline-6-carboxylate (155 mg, 0.3 mmol), ethylboronic acid (89 mg, 1.2 mmol), $K_2CO_3$ (249 mg, 1.8 mmol) and Pd(dppf)$Cl_2 \cdot CH_2Cl_2$ (44 mg, 0.06 mmol) in THF (3.6 mL) and water (0.9 mL) was heated at 65° C. with stirring overnight under argon. After being cooled to rt, to the mixture was added 4 M sodium hydroxide solution (1.5 mL, 6 mmol). The resulting mixture was stirred at rt for 1 h, then diluted with water and acidified with 2 M hydrochloric acid to pH=2-3. The mixture was extracted with $CH_2Cl_2$ for three times. The combined organic layers were washed with brine, dried over anhydrous $Na_2SO_4$ and concentrated under reduced pressure. The residue was purified by prep-HPLC to afford cis-10-methoxy-3,3,11-trimethyl-7-oxo-1,2,3,3a,7,12b-hexahydrocyclopenta[c]pyrido[2,1-a]isoquinoline-6-carboxylic acid (9 mg) as a yellow solid. $^1$H NMR (400 MHz, $CDCl_3$) δ ppm 8.47 (s, 1H), 7.42 (s, 1H), 7.19 (s, 1H), 7.18 (s, 1H), 4.18 (d, 1H), 3.93 (s, 3H), 3.85-3.78 (m, 1H), 2.81-2.63 (m, 2H), 2.39-2.26 (m, 2H), 1.68 (ddd, 1H), 1.50 (td, J=8.4, 12.9 Hz, 1H), 1.28 (s, 3H), 1.24 (t, 3H), 0.53 (s, 3H). MS obsd. (ESI$^+$) [(M+H)$^+$]: 368.

Example 40: Cis-10-methoxy-3,3-dimethyl-7-oxo-11-propyl-1,2,3,3a,7,12b-hexahydrocyclopenta[c]pyrido[2,1-a]isoquinoline-6-carboxylic acid

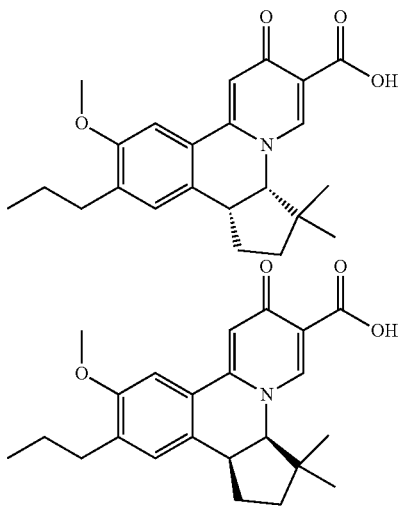

A mixture of cis-ethyl 10-methoxy-3,3-dimethyl-7-oxo-11-(((trifluoromethyl)sulfonyl)oxy)-1,2,3,3a,7,12b-hexahydrocyclopenta[c]pyrido[2,1-a]isoquinoline-6-carboxylate (155 mg, 0.3 mmol), propylboronic acid (105 mg, 1.2 mmol), $K_2CO_3$ (249 mg, 1.8 mmol) and Pd(dppf)$Cl_2 \cdot CH_2Cl_2$ (44 mg, 0.06 mmol) in THF (3.6 mL) and water (0.9 mL) was heated at 65° C. overnight under argon. After being cooled to rt, to the mixture was added 4 M sodium hydroxide solution (1.5 mL, 6 mmol). The mixture was stirred at rt for 1 h, then diluted with water and acidified with 2 M hydrochloric acid to pH=2-3. The resulting mixture was extracted with $CH_2Cl_2$ for three times. The combined organic layers were washed with brine, dried over anhydrous $Na_2SO_4$ and concentrated under reduced pressure. The residue was purified by prep-HPLC to afford cis-10-methoxy-3,3-dimethyl-7-oxo-11-propyl-1,2,3,3a,7,12b-hexahydrocyclopenta[c]pyrido[2,1-a]isoquinoline-6-carboxylic acid (12 mg) as a yellow solid. $^1$H NMR (400 MHz, $CDCl_3$) δ ppm 8.46 (s, 1H), 7.37 (s, 1H), 7.18 (s, 1H), 7.17 (s, 1H), 4.17 (d, 1H), 3.92 (s, 3H), 3.85-3.77 (m, 1H), 2.74-2.59 (m, 2H), 2.38-2.28 (m, 2H), 1.65 (m, 2H), 1.54-1.44 (m, 1H), 1.28 (s, 3H), 1.25 (s, 1H), 0.98 (t, 3H), 0.53 (s, 3H). MS obsd. (ESI$^+$) [(M+H)$^+$]: 382.

Example 41: Cis-10-methoxy-3,3-dimethyl-7-oxo-11-(pyrrolidin-1-yl)-1,2,3,3a,7,12b-hexahydrocyclopenta[c]pyrido[2,1-a]isoquinoline-6-carboxylic acid

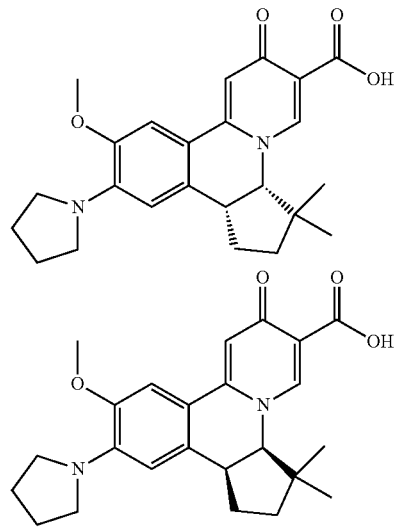

To a solution of cis-ethyl 10-methoxy-3,3-dimethyl-7-oxo-11-(((trifluoromethyl)sulfonyl)oxy)-1,2,3,3a,7,12b-hexahydrocyclopenta[c]pyrido[2,1-a]isoquinoline-6-carboxylate (155 mg, 0.3 mmol) in NMP (2 mL) was added pyrrolidine (107 mg, 1.5 mmol). The reaction vessel was sealed and heated to 150° C. under microwave irradiation for 3 hrs. After being cooled to rt, to the resulting mixture was added 4 M sodium hydroxide aqueous solution (1.5 mL, 6 mmol). The resulting mixture was stirred at rt for 1 h, and then purified by prep-HPLC to afford cis-10-methoxy-3,3-dimethyl-7-oxo-11-(pyrrolidin-1-yl)-1,2,3,3a,7,12b-hexahydrocyclopenta[c]pyrido[2,1-a]isoquinoline-6-carboxylic acid (18 mg) as a yellow powder. $^1$H NMR (400 MHz, $CDCl_3$) δ ppm 8.37 (s, 1H), 7.08 (s, 1H), 7.07 (s, 1H), 6.46 (s, 1H), 4.10 (d, 1H), 3.87 (s, 3H), 3.78-3.70 (m, 1H), 3.63-3.49 (m, 4H), 2.34-2.25 (m, 2H), 2.02-1.94 (m, 4H), 1.69-1.49 (m, 2H), 1.26 (s, 3H), 0.56 (s, 3H). MS obsd. (ESI$^+$) [(M+H)$^+$]: 409.

BIOLOGICAL EXAMPLES

Example 42 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at $1.5 \times 10^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the $IC_{50}$ value was extrapolated by using the E-WorkBook Suite (ID Business Solutions Ltd., Guildford, UK). The $IC_{50}$ was defined as the compound concentration (or conditioned media log dilution) at which HBsAg secretion was reduced by 50% compared to the no drug control.

The compounds of the present invention were tested for their activity to inhibit HBsAg as described herein. The Examples were tested in the above assay and found to have IC50 below 25.0 μM. Particular compounds of formula I were found to have IC50 below 0.100 μM. More Particular compounds of formula I were found to have IC50 below 0.010 μM. Results of HBsAg assay are given in Table 1.

TABLE 1

Activity data in HBsAg assay

| Example No. | $IC_{50}$ (μM) |
| --- | --- |
| 1 | 0.01 |
| 2 | 0.001 |
| 3 | 0.003 |
| 4 | 0.003 |
| 5 | 0.308 |
| 6 | 0.084 |
| 7 | 0.005 |
| 8 | 0.003 |
| 9 | 0.001 |
| 10 | 0.001 |
| 11 | 0.004 |
| 12 | 0.004 |
| 13 | 0.005 |
| 14 | 0.003 |
| 15 | 0.006 |
| 16 | 0.128 |
| 17 | 0.025 |
| 18 | 0.01 |
| 19 | 0.505 |
| 20 | 0.002 |
| 21 | 0.017 |
| 22 | 0.001 |
| 23 | 0.002 |
| 24 | 0.02 |
| 25 | 0.006 |
| 26 | 0.002 |
| 27 | 0.02 |
| 28 | 0.003 |
| 29 | 0.152 |
| 30 | 0.564 |
| 31 | 0.12 |
| 32 | 0.044 |
| 33 | 0.265 |
| 34 | 0.186 |
| 35 | 0.11 |
| 36 | 0.028 |
| 37 | 2.202 |
| 38 | 0.036 |
| 39 | 0.02 |
| 40 | 0.019 |
| 41 | <0.0016 |

HBV DNA Assay

The assay employs real-time qPCR (TaqMan) to directly measure extracellular HBV DNA copy number. HepG2.2.15 cells were plated in 96-well microtiter plates. Only the interior wells were utilized to reduce "edge effects" observed during cell culture, the exterior wells were filled with complete medium to help minimize sample evaporation. On the following day, the HepG2.2.15 cells were washed and the medium was replaced with complete medium containing various concentrations of a test compound in triplicate. 3TC was used as the positive control, while media alone was added to cells as a negative control (virus control, VC). Three days later, the culture medium was replaced with fresh medium containing the appropriately diluted drug. Six days following the initial administration of the test compound, the cell culture supernatant was collected, treated with pronase and then used in a real-time qPCR/TaqMan assay to determine HBV DNA copy numbers. Antiviral activity was calculated from the reduction in HBV DNA levels ($IC_{50}$).

The compounds of the present invention were tested for their activity to anti HBV DNA production as described herein. The Examples were tested in the above assay and found to have IC50 below 25.0 μM. Particular compounds of formula I were found to have IC50 below 0.10 μM. Results of HBV DNA assay are given in Table 2.

TABLE 2

Anti HBV DNA production activity in HepG2.2.15 cells

| Example No. | $IC_{50}$ (μM) |
| --- | --- |
| 3 | 0.04 |
| 28 | <0.032 |

We claim:
1. A compound of formula I,

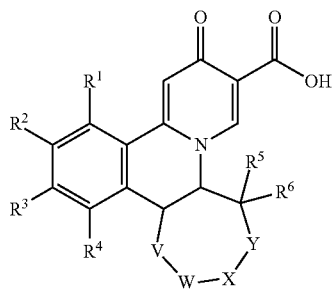

wherein
R$^1$, R$^2$, R$^3$ and R$^4$ are independently selected from hydrogen, C$_{1-6}$alkyl, haloC$_{1-6}$alkyl, halogen, cyano, amino, C$_{1-6}$alkylamino, diC$_{1-6}$alkylamino, pyrrolidinyl and OR$^7$;
R$^5$ is hydrogen or C$_{1-6}$alkyl;
R$^6$ is hydrogen or C$_{1-6}$alkyl;
R$^7$ is hydrogen; C$_{1-6}$alkyl; haloC$_{1-6}$alkyl; C$_{3-7}$cycloalkylC$_{1-6}$alkyl; phenylC$_{1-6}$alkyl; cyanoC$_{1-6}$alkyl; hydroxyC$_{1-6}$alkyl; C$_{1-6}$alkoxyC$_{1-6}$alkyl; carboxyC$_{1-6}$alkyl; C$_{1-6}$alkoxycarbonylC$_{1-6}$alkyl; C$_{1-6}$alkylsulfanylC$_{1-6}$alkyl; C$_{1-6}$alkylsulfonylC$_{1-6}$alkyl; aminoC$_{1-6}$alkyl; C$_{1-6}$alkylaminoC$_{1-6}$alkyl; diC$_{1-6}$alkylaminoC$_{1-6}$alkyl; C$_{1-6}$alkylcarbonylaminoC$_{1-6}$alkyl; C$_{1-6}$alkylsulfonylaminoC$_{1-6}$alkyl; C$_{1-6}$alkoxycarbonylaminoC$_{1-6}$alkyl; or heterocycloalkylC$_{1-6}$alkyl, wherein heterocycloalkyl is N-containing monocyclic heterocycloalkyl;
One of V, W, X and Y is selected from CR$^8$R$^9$, O, S, SO$_2$ and NR$^{10}$, the others of V, W, X and Y are independently selected from a bond and CR$^8$R$^9$, wherein
R$^8$ is hydrogen or C$_{1-6}$alkyl;
R$^9$ is hydrogen or C$_{1-6}$alkyl;
R$^{10}$ is phenylC$_{1-6}$alkoxycarbonyl, phenylC$_{1-6}$alkylcarbonyl, phenylC$_{1-6}$alkylsulfonyl, C$_{1-6}$alkoxycarbonyl, C$_{1-6}$alkylcarbonyl, or C$_{1-6}$alkylsulfonyl;
or a pharmaceutically acceptable salt, or an enantiomer, or a diastereomer thereof.

2. The compound of formula I according to claim 1, wherein
R$^1$ is hydrogen;
R$^2$ is halogen or C$_{1-6}$alkoxy;
R$^3$ is selected from C$_{1-6}$alkyl, pyrrolidinyl or OR$^7$, wherein
R$^7$ is hydrogen, C$_{1-6}$alkyl, haloC$_{1-6}$alkyl, C$_{3-7}$cycloalkylC$_{1-6}$alkyl, phenylC$_{1-6}$alkyl, cyanoC$_{1-6}$alkyl, hydroxyC$_{1-6}$alkyl, C$_{1-6}$alkoxyC$_{1-6}$alkyl, carboxyC$_{1-6}$alkyl, C$_{1-6}$alkoxycarbonylC$_{1-6}$alkyl, C$_{1-6}$alkylsulfanylC$_{1-6}$alkyl, C$_{1-6}$alkylsulfonylC$_{1-6}$alkyl, aminoC$_{1-6}$alkyl, C$_{1-6}$alkylcarbonylaminoC$_{1-6}$alkyl, C$_{1-6}$alkylsulfonylaminoC$_{1-6}$alkyl, C$_{1-6}$alkoxycarbonylaminoC$_{1-6}$alkyl, morpholinylC$_{1-6}$alkyl, pyrrolidinylC$_{1-6}$alkyl or (2-oxo-pyrrolidinyl)C$_{1-6}$alkyl;
R$^4$ is hydrogen;
R$^5$ is hydrogen or C$_{1-6}$alkyl;
R$^6$ is hydrogen or C$_{1-6}$alkyl;
V and Y are CH$_2$;
X is selected from a bond, CH$_2$, O, S, SO$_2$ and phenylC$_{1-6}$alkoxycarbonylamino when W is a bond; or
X is CH$_2$ when W is CH$_2$;
or a pharmaceutically acceptable salt, or an enantiomer, or a diastereomer thereof.

3. The compound of formula I according to claim 2, wherein
R$^1$ is hydrogen;
R$^2$ is chloro or methoxy;
R$^3$ is selected from methyl, ethyl, propyl, pyrrolidinyl, hydroxy, methoxy, difluoroethoxy, trifluoroethoxy, cyclopropylmethoxy, benzyloxy, cyanopropoxy, hydroxypropoxy, hydroxyhexyloxy, hydroxydimethylpropoxy, methoxyethoxy, methoxypropoxy, carboxypropoxy, ethoxycarbonylpropoxy, methylsulfanylpropoxy, methylsulfonylpropoxy, aminohexyloxy, methylcarbonylaminohexyloxy, methylsulfonylaminohexyloxy, tert-butoxycarbonylaminohexyloxy, morpholinylpropoxy, pyrrolidinylpropoxy and (2-oxo-pyrrolidinyl)propoxy;
R$^4$ is hydrogen;
R$^5$ is hydrogen or methyl;
R$^6$ is hydrogen or methyl;
V and Y are CH$_2$;
X is selected from a bond, CH$_2$, O, S, SO$_2$ and phenylmethoxycarbonylamino when W is a bond; or
X is CH$_2$ when W is CH$_2$;
or or a pharmaceutically acceptable salt, or an enantiomer, or a diastereomer thereof.

4. The compound of formula I according to claim 1, wherein
R$^1$ is hydrogen;
R$^2$ is C$_{1-6}$alkoxy;
R$^3$ is selected from C$_{1-6}$alkyl, pyrrolidinyl or OR$^7$, wherein R$^7$ is hydrogen, C$_{1-6}$alkyl, haloC$_{1-6}$alkyl, C$_{3-7}$cycloalkylC$_{1-6}$alkyl, phenylC$_{1-6}$alkyl, cyanoC$_{1-6}$alkyl, hydroxyC$_{1-6}$alkyl, C$_{1-6}$alkoxyC$_{1-6}$alkyl, carboxyC$_{1-6}$alkyl, C$_{1-6}$alkoxycarbonylC$_{1-6}$alkyl, C$_{1-6}$alkylsulfanylC$_{1-6}$alkyl, C$_{1-6}$alkylsulfonylC$_{1-6}$alkyl, aminoC$_{1-6}$alkyl, C$_{1-6}$alkylcarbonylaminoC$_{1-6}$alkyl, C$_{1-6}$alkylsulfonylaminoC$_{1-6}$alkyl, C$_{1-6}$alkoxycarbonylaminoC$_{1-6}$alkyl, morpholinylC$_{1-6}$alkyl, pyrrolidinylC$_{1-6}$alkyl or (2-oxo-pyrrolidinyl)C$_{1-6}$alkyl;
R$^4$ is hydrogen;
R$^5$ is C$_{1-6}$alkyl;
R$^6$ is C$_{1-6}$alkyl;
V and Y are CH$_2$;
W is a bond;
X is a bond;
or or a pharmaceutically acceptable salt, or an enantiomer, or a diastereomer thereof.

5. The compound of formula I according to claim 1 or a pharmaceutically acceptable salt, or an enantiomer, or a diastereomer thereof, wherein R$^2$ is methoxy.

6. The compound of formula I according to claim 1, or or a pharmaceutically acceptable salt, or an enantiomer, or a diastereomer thereof, wherein R$^3$ is OR$^7$, wherein R$^7$ is C$_{1-6}$alkyl, haloC$_{1-6}$alkyl, C$_{3-7}$cycloalkylC$_{1-6}$alkyl, hydroxyC$_{1-6}$alkyl, C$_{1-6}$alkoxyC$_{1-6}$alkyl, C$_{1-6}$alkylsulfanylC$_{1-6}$alkyl, C$_{1-6}$alkylsulfonylC$_{1-6}$alkyl, aminoC$_{1-6}$alkyl, C$_{1-6}$alkylcarbonylaminoC$_{1-6}$alkyl, C$_{1-6}$alkylsulfonylaminoC$_{1-6}$alkyl, C$_{1-6}$alkoxycarbonylaminoC$_{1-6}$alkyl or morpholinylC$_{1-6}$alkyl.

7. The compound of formula I according to claim 1, or a pharmaceutically acceptable salt, or an enantiomer, or a diastereomer, wherein R$^3$ is selected from methoxy, difluoroethoxy, trifluoroethoxy, cyclopropylmethoxy, hydroxypropoxy, hydroxyhexyloxy, hydroxydimethylpropoxy, methoxyethoxy, methoxypropoxy, methylsulfanylpropoxy, methylsulfonylpropoxy, aminohexyloxy, methylcarbonylaminohexyloxy, methylsulfonylaminohexyloxy, tert-butoxycarbonylaminohexyloxy or morpholinylpropoxy.

8. The compound of formula I according to claim 1 or a pharmaceutically acceptable salt, or an enantiomer, or a diastereomer thereof, wherein $R^5$ is methyl and $R^6$ is methyl.

9. The compound of formula I according to claim 1, wherein
$R^1$ is hydrogen;
$R^2$ is halogen or $C_{1-6}$alkoxy;
$R^3$ is $OR^7$; wherein $R^7$ is phenyl$C_{1-6}$alkyl or $C_{1-6}$alkoxy$C_{1-6}$alkyl;
$R^4$ is hydrogen;
$R^5$ is hydrogen;
$R^6$ is hydrogen;
V and Y are $CH_2$;
X is selected from $CH_2$, O, S, $SO_2$ and phenyl$C_{1-6}$alkoxycarbonylamino when W is a bond; or
X is $CH_2$ when W is $CH_2$;
or a pharmaceutically acceptable salt, or an enantiomer, or a diastereomer thereof.

10. The compound according to claim 1, or or a pharmaceutically acceptable salt, or an enantiomer, or a diastereomer thereof, wherein $R^2$ is chloro or methoxy.

11. The compound according to claim 1, or a pharmaceutically acceptable salt, or an enantiomer, or a diastereomer thereof, wherein $R^3$ is benzyloxy or methoxypropoxy.

12. The compound according to claim 1, or a pharmaceutically acceptable salt, or an enantiomer, or a diastereomer thereof, wherein X is $CH_2$ or S when W is a bond, or X is $CH_2$ when W is $CH_2$.

13. The compound according to claim 2, wherein
$R^1$ is hydrogen;
$R^2$ is halogen or $C_{1-6}$alkoxy;
$R^3$ is selected from $C_{1-6}$alkyl, pyrrolidinyl or $OR^7$, wherein $R^7$ is halo$C_{1-6}$alkyl, hydroxy$C_{1-6}$alkyl, $C_{1-6}$alkoxy$C_{1-6}$alkyl, $C_{1-6}$alkylsulfonyl$C_{1-6}$alkyl, $C_{1-6}$alkylcarbonylamino$C_{1-6}$alkyl, $C_{1-6}$alkylsulfonylamino$C_{1-6}$alkyl or morpholinyl$C_{1-6}$alkyl;
$R^4$ is hydrogen;
$R^5$ is hydrogen or $C_{1-6}$alkyl;
$R^6$ is hydrogen or $C_{1-6}$alkyl;
V and Y are $CH_2$;
X is a bond or S when W is a bond, or
X is $CH_2$ when W is $CH_2$;
or a pharmaceutically acceptable salt, or an enantiomer, or a diastereomer thereof.

14. The compound according to claim 13, wherein
$R^1$ is hydrogen;
$R^2$ is chloro or methoxy;
$R^3$ is selected from ethyl, pyrrolidinyl, difluoroethoxy, trifluoroethoxy, hydroxydimethylpropoxy, methoxypropoxy, methylsulfonylpropoxy, methylcarbonylaminohexyloxy, methylsulfonylaminohexyloxy and morpholinylpropoxy;
$R^4$ is hydrogen;
$R^5$ is hydrogen or methyl;
$R^6$ is hydrogen or methyl;
V and Y are $CH_2$;
X is a bond or S when W is a bond, or
X is $CH_2$ when W is $CH_2$;
or or a pharmaceutically acceptable salt, or an enantiomer, or a diastereomer thereof.

15. The compound according to claim 1, which compound is selected from the group consisting of:
Trans-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid;
Cis-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid;
Cis-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid;
(3aS,12bR)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid;
(3aR,12bS)-11-(benzyloxy)-10-methoxy-3,3-dimethyl-7-oxo-1,2,3,3a,7,12b-hexahydrocyclopenta[c]pyrido[2,1-a]isoquinoline-6-carboxylic acid;
Cis-11-hydroxy-10-methoxy-3,3-dimethyl-7-oxo-1,2,3,3a,7,12b-hexahydrocyclopenta[c]pyrido[2,1-a]isoquinoline-6-carboxylic acid;
Cis-10,11-dimethoxy-3,3-dimethyl-7-oxo-1,2,3,3a,7,12b-hexahydrocyclopenta[c]pyrido[2,1-a]isoquinoline-6-carboxylic acid;
Cis-10-methoxy-3,3-dimethyl-7-oxo-11-(2,2,2-trifluoroethoxy)-1,2,3,3a,7,12b-hexahydrocyclopenta[c]pyrido[2,1-a]isoquinoline-6-carboxylic acid;
Cis-11-isobutoxy-10-methoxy-3,3-dimethyl-7-oxo-1,2,3,3a,7,12b-hexahydrocyclopenta[c]pyrido[2,1-a]isoquinoline-6-carboxylic acid;
Cis-11-(cyclopropylmethoxy)-10-methoxy-3,3-dimethyl-7-oxo-1,2,3,3a,7,12b-hexahydrocyclopenta[c]pyrido[2,1-a]isoquinoline-6-carboxylic acid;
Cis-10-methoxy-11-(2-methoxyethoxy)-3,3-dimethyl-7-oxo-1,2,3,3a,7,12b-hexahydrocyclopenta[c]pyrido[2,1-a]isoquinoline-6-carboxylic acid;
Cis-11-(3-cyanopropoxy)-10-methoxy-3,3-dimethyl-7-oxo-1,2,3,3a,7,12b-hexahydrocyclopenta[c]pyrido[2,1-a]isoquinoline-6-carboxylic acid;
Cis-11-(3-hydroxypropoxy)-10-methoxy-3,3-dimethyl-7-oxo-1,2,3,3a,7,12b-hexahydrocyclopenta[c]pyrido[2,1-a]isoquinoline-6-carboxylic acid;
Cis-11-(3-hydroxy-2,2-dimethylpropoxy)-10-methoxy-3,3-dimethyl-7-oxo-1,2,3,3a,7,12b-hexahydrocyclopenta[c]pyrido[2,1-a]isoquinoline-6-carboxylic acid;
Cis-10-methoxy-3,3-dimethyl-11-(3-morpholinopropoxy)-7-oxo-1,2,3,3a,7,12b-hexahydrocyclopenta[c]pyrido[2,1-a]isoquinoline-6-carboxylic acid;
Cis-10-methoxy-3,3-dimethyl-7-oxo-11-(3-(pyrrolidin-1-yl)propoxy)-1,2,3,3a,7,12b-hexahydrocyclopenta[c]pyrido[2,1-a]isoquinoline-6-carboxylic acid;
Cis-10-methoxy-3,3-dimethyl-7-oxo-11-(3-(2-oxopyrrolidin-1-yl)propoxy)-1,2,3,3a,7,12b-hexahydrocyclopenta[c]pyrido[2,1-a]isoquinoline-6-carboxylic acid;
Cis-11-(4-ethoxy-4-oxobutoxy)-10-methoxy-3,3-dimethyl-7-oxo-1,2,3,3a,7,12b-hexahydrocyclopenta[c]pyrido[2,1-a]isoquinoline-6-carboxylic acid;
Cis-11-(3-carboxypropoxy)-10-methoxy-3,3-dimethyl-7-oxo-1,2,3,3a,7,12b-hexahydrocyclopenta[c]pyrido[2,1-a]isoquinoline-6-carboxylic acid;
Cis-10-methoxy-3,3-dimethyl-11-(3-(methylthio)propoxy)-7-oxo-1,2,3,3a,7,12b-hexahydrocyclopenta[c]pyrido[2,1-a]isoquinoline-6-carboxylic acid;
Cis-10-methoxy-3,3-dimethyl-11-(3-(methylsulfonyl)propoxy)-7-oxo-1,2,3,3a,7,12b-hexahydrocyclopenta[c]pyrido[2,1-a]isoquinoline-6-carboxylic acid;
Cis-11-((6-hydroxyhexyl)oxy)-10-methoxy-3,3-dimethyl-7-oxo-1,2,3,3a,7,12b-hexahydrocyclopenta[c]pyrido[2,1-a]isoquinoline-6-carboxylic acid;
Cis-11-((6-((tert-butoxycarbonyl)amino)hexyl)oxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-((6-aminohexyl)oxy)-10-methoxy-3,3-dimethyl-7-oxo-1,2,3,3a,7,12b-hexahydrocyclopenta[c]pyrido[2,1-a]isoquinoline-6-carboxylic acid;

Cis-11-((6-acetamidohexyl)oxy)-10-methoxy-3,3-dimethyl-7-oxo-1,2,3,3a,7,12b-hexahydrocyclopenta[c]pyrido[2,1-a]isoquinoline-6-carboxylic acid;

Cis-10-methoxy-3,3-dimethyl-11-((6-(methylsulfonamido)hexyl)oxy)-7-oxo-1,2,3,3a,7,12b-hexahydrocyclopenta[c]pyrido[2,1-a]isoquinoline-6-carboxylic acid;

Trans-13-chloro-12-(3-methoxypropoxy)-2-oxo-2,5a,6,7,8,9,10,10a-octahydrocyclohepta[c]pyrido[2,1-a]isoquinoline-3-carboxylic acid;

Cis-13-chloro-12-(3-methoxypropoxy)-2-oxo-2,5a,6,7,8,9,10,10a-octahydrocyclohepta[c]pyrido[2,1-a]isoquinoline-3-carboxylic acid;

Trans-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid;

Cis-2-((benzyloxy)carbonyl)-11-methoxy-12-(3-methoxypropoxy)-8-oxo-2,3,4,4a,8,13b-hexahydro-1H-benzo[c]pyrido[1,2-a][1,6]naphthyridine-7-carboxylic acid;

Trans-12-benzyloxy-11-methoxy-8-oxo-1,2,3,4,4a,13b-hexahydropyrido[1,2-f]phenanthridine-7-carboxylic acid;

Cis-12-benzyloxy-11-methoxy-8-oxo-1,2,3,4,4a,13b-hexahydropyrido[1,2-f]phenanthridine-7-carboxylic acid;

Trans-11-methoxy-12-(3-methoxypropoxy)-8-oxo-1,3,4,4a,8,13b-hexahydropyrano[4,3-c]pyrido[2,1-a]isoquinoline-7-carboxylic acid;

Cis-11-methoxy-12-(3-methoxypropoxy)-8-oxo-1,3,4,4a,8,13b-hexahydropyrano[4,3-c]pyrido[2,1-a]isoquinoline-7-carboxylic acid;

Trans-11-methoxy-12-(3-methoxypropoxy)-8-oxo-1,3,4,4a,8,13b-hexahydropyrido[2,1-a]thiopyrano[4,3-c]isoquinoline-7-carboxylic acid;

Cis-11-methoxy-12-(3-methoxypropoxy)-8-oxo-1,3,4,4a,8,13b-hexahydropyrido[2,1-a]thiopyrano[4,3-c]isoquinoline-7-carboxylic acid;

Trans-11-methoxy-12-(3-methoxypropoxy)-8-oxo-1,3,4,4a,8,13b-hexahydropyrido[2,1-a]thiopyrano[4,3-c]isoquinoline-7-carboxylic acid 2,2-dioxide;

Cis-10-methoxy-3,3,11-trimethyl-7-oxo-1,2,3,3a,7,12b-hexahydrocyclopenta[c]pyrido[2,1-a]isoquinoline-6-carboxylic acid;

Cis-10-methoxy-3,3,11-trimethyl-7-oxo-1,2,3,3a,7,12b-hexahydrocyclopenta[c]pyrido[2,1-a]isoquinoline-6-carboxylic acid;

Cis-10-methoxy-3,3-dimethyl-7-oxo-11-propyl-1,2,3,3a,7,12b-hexahydrocyclopenta[c]pyrido[2,1-a]isoquinoline-6-carboxylic acid; and, Cis-10-methoxy-3,3-dimethyl-7-oxo-11-(pyrrolidin-1-yl)-1,2,3,3a,7,12b-hexahydrocyclopenta[c]pyrido[2,1-a]isoquinoline-6-carboxylic acid;

or or a pharmaceutically acceptable salt, or an enantiomer, or a diastereomer thereof.

16. A compound according to claim 1, selected from
Trans-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid;

Cis-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid;

Cis-10-methoxy-3,3-dimethyl-7-oxo-11-(2,2,2-trifluoroethoxy)-1,2,3,3a,7,12b-hexahydrocyclopenta[c]pyrido[2,1-a]isoquinoline-6-carboxylic acid;

Cis-11-isobutoxy-10-methoxy-3,3-dimethyl-7-oxo-1,2,3,3a,7,12b-hexahydrocyclopenta[c]pyrido[2,1-a]isoquinoline-6-carboxylic acid;

Cis-11-(3-hydroxy-2,2-dimethylpropoxy)-10-methoxy-3,3-dimethyl-7-oxo-1,2,3,3a,7,12b-hexahydrocyclopenta[c]pyrido[2,1-a]isoquinoline-6-carboxylic acid;

Cis-10-methoxy-3,3-dimethyl-11-(3-morpholinopropoxy)-7-oxo-1,2,3,3a,7,12b-hexahydrocyclopenta[c]pyrido[2,1-a]isoquinoline-6-carboxylic acid;

Cis-10-methoxy-3,3-dimethyl-11-(3-(methylsulfonyl)propoxy)-7-oxo-1,2,3,3a,7,12b-hexahydrocyclopenta[c]pyrido[2,1-a]isoquinoline-6-carboxylic acid;

Cis-11-((6-acetamidohexyl)oxy)-10-methoxy-3,3-dimethyl-7-oxo-1,2,3,3a,7,12b-hexahydrocyclopenta[c]pyrido[2,1-a]isoquinoline-6-carboxylic acid;

Cis-10-methoxy-3,3-dimethyl-11-((6-(methylsulfonamido)hexyl)oxy)-7-oxo-1,2,3,3a,7,12b-hexahydrocyclopenta[c]pyrido[2,1-a]isoquinoline-6-carboxylic acid;

Cis-13-chloro-12-(3-methoxypropoxy)-2-oxo-2,5a,6,7,8,9,10,10a-octahydrocyclohepta[c]pyrido[2,1-a]isoquinoline-3-carboxylic acid;

Cis-11-methoxy-12-(3-methoxypropoxy)-8-oxo-1,3,4,4a,8,13b-hexahydropyrido[2,1-a]thiopyrano[4,3-c]isoquinoline-7-carboxylic acid;

Cis-10-methoxy-3,3,11-trimethyl-7-oxo-1,2,3,3a,7,12b-hexahydrocyclopenta[c]pyrido[2,1-a]isoquinoline-6-carboxylic acid;

Cis-10-methoxy-3,3-dimethyl-7-oxo-11-(pyrrolidin-1-yl)-1,2,3,3a,7,12b-hexahydrocyclopenta[c]pyrido[2,1-a]isoquinoline-6-carboxylic acid;

or a pharmaceutically acceptable salt, or an enantiomer, or a diastereomer thereof.

17. A process for the preparation of a compound according to claim 1 comprising hydrolysis of a compound of formula (A)

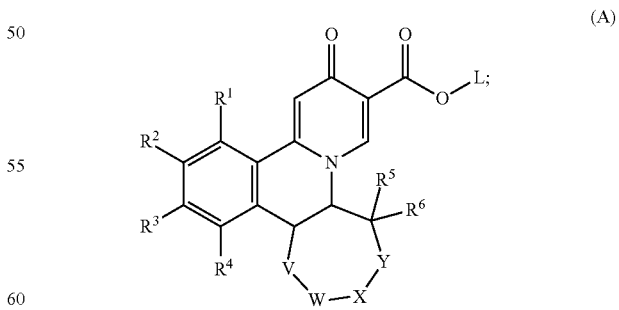

wherein $R^1$ to $R^7$, V, W, X and Y are defined in claim 1 and, L is $C_{1-6}$alkyl.

18. A process for the preparation of a compound according to claim 1 comprising hydrolysis of a compound of formula (B)

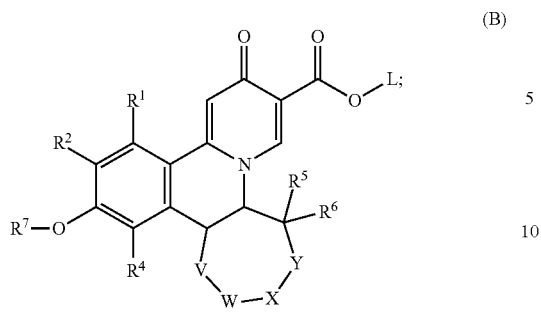

wherein $R^1$ to $R^7$, V, W, X and Y are defined as in claim 1 and L is $C_{1-6}$alkyl.

19. A pharmaceutical composition comprising a compound of claim 1 and a pharmaceutically acceptable carrier, diluent or excipient.

20. A method for inhibition of HBsAg production or secretion in a cell comprising treating the cell with a therapeutically effective amount of a compound of claim 1.

21. A method for the treatment or prophylaxis of HBV infection, which method comprises administering a therapeutically effective amount of a compound of claim 1 to a patient in need thereof.

* * * * *